US011359029B2

(12) United States Patent
Chiu et al.

(10) Patent No.: US 11,359,029 B2
(45) Date of Patent: Jun. 14, 2022

(54) FC ENGINEERED ANTI-TNFR SUPERFAMILY MEMBER ANTIBODIES HAVING ENHANCED AGONISTIC ACTIVITY AND METHODS OF USING THEM

(71) Applicant: Janssen Biotech, Inc., Horsham, PA (US)

(72) Inventors: Mark Chiu, Paoli, PA (US); Di Zhang, Hillsborough, NJ (US)

(73) Assignee: Janssen Biotech, Inc., Horsham, PA (US), PART INTEREST ( * ) Notice: Subject to any disclaimer, the term of this patent is extended or adjusted under 35 U.S.C. 154(b) by 0 days.

(21) Appl. No.: 16/840,830

(22) Filed: Apr. 6, 2020

(65) Prior Publication Data

US 2020/0231693 A1 Jul. 23, 2020

Related U.S. Application Data

(63) Continuation of application No. 15/668,895, filed on Aug. 4, 2017, now abandoned.

(60) Provisional application No. 62/374,347, filed on Aug. 12, 2016.

(51) Int. Cl.
*C07K 16/28* (2006.01)

(52) U.S. Cl.
CPC ...... *C07K 16/2878* (2013.01); *C07K 2317/52* (2013.01); *C07K 2317/72* (2013.01); *C07K 2317/732* (2013.01); *C07K 2317/734* (2013.01); *C07K 2317/75* (2013.01)

(58) Field of Classification Search
CPC ............ C07K 2317/75; C07K 2317/52; C07K 2317/732; C07K 2317/72; C07K 2317/734; C07K 16/2878
See application file for complete search history.

(56) References Cited

U.S. PATENT DOCUMENTS 4,683,195 A 7/1987 Mullis et al.
5,223,409 A 6/1993 Ladner et al.
5,225,539 A 7/1993 Winter
5,403,484 A 4/1995 Ladner et al.
5,427,908 A 6/1995 Dower et al.
5,571,698 A 11/1996 Ladner et al.
5,580,717 A 12/1996 Dower et al.
5,624,821 A 4/1997 Winter et al.
5,885,793 A 3/1999 Griffiths et al.
5,969,108 A 10/1999 McCafferty et al.
6,150,584 A 11/2000 Kucherlapati et al.
6,172,197 B1 1/2001 McCafferty et al.
6,521,404 B1 2/2003 Griffiths et al.
6,544,731 B1 4/2003 Griffiths et al.
6,555,313 B1 4/2003 Griffiths et al.
6,582,915 B1 6/2003 Griffiths et al.
6,593,081 B1 7/2003 Griffiths et al.
6,737,056 B1 5/2004 Presta
6,818,749 B1 11/2004 Kashmiri et al.
7,288,251 B2 10/2007 Bedian et al.
7,288,638 B2 10/2007 Jure-Kunkel et al.
7,618,632 B2 11/2009 Collins et al.
7,709,226 B2 5/2010 Foote
7,812,135 B2 10/2010 Smith et al.
7,960,515 B2 6/2011 Min et al.
8,133,983 B2 3/2012 Bakker et al.
8,242,247 B2 8/2012 Klein et al.
8,303,955 B2 11/2012 Presta et al.
8,591,886 B2 11/2013 Ponath et al.
8,716,452 B2 5/2014 Jure-Kunkel et al.
8,748,356 B2 6/2014 Raghunathan
8,821,867 B2 9/2014 Ahrens et al.
9,169,325 B2 10/2015 Keler et al.
2007/0287170 A1 12/2007 Davis et al.
2009/0182127 A1 7/2009 Kjaergaard et al.
2010/0015133 A1 1/2010 Igawa et al.
2010/0028637 A1 2/2010 Tavsanli et al.
2010/0261620 A1 10/2010 Almagro et al.
2011/0123532 A1 5/2011 Gurney et al.
2012/0149876 A1 6/2012 Von Kreudenstein et al.
2013/0183316 A1 7/2013 Van Eenennaam et al.
2013/0195849 A1 8/2013 Von Kreudenstein et al.
2013/0280275 A1 10/2013 Liu et al.
2014/0242075 A1 8/2014 Parren et al.
2014/0273092 A1 9/2014 Filikweert et al.
2014/0377284 A1 12/2014 Simons et al.
2015/0175707 A1 6/2015 De Jong et al.
2015/0259434 A1 9/2015 Johnson et al.
2015/0337053 A1 11/2015 McCarthy et al.
2018/0037634 A1* 2/2018 Viswanathan ......... C07K 16/10

FOREIGN PATENT DOCUMENTS

WO WO1988/01649 A1 3/1988
WO WO1990/04036 A1 4/1990
WO WO1990/007861 A1 7/1990

(Continued)

OTHER PUBLICATIONS

Alegre, et al., "a non-activating "humanized" anti-CD3 monoclonal antibody retains immunosuppressive properties in vivo," Transplantation, 57 (100): 1537-1543 (1994).
An, et al. "IgG2m4, an engineered antibody isotype with reduced Fc function." *MAbs* 1(6): 572-579 (2009).
Bedu-Addo, et al. "Use of biophysical characterization in preformulation development of a heavy-chain fragment of botulinum serotype B: evaluation of suitable purification process conditions." *Pharm. Res.* 21: 1353-1361 (2004).
Bolt, et al. "The generation of a humanized, non-mitogenic CD3 monoclonal antibody which retains in vitro immunosuppressive properties." *Eur J Immunol* 23(2): 403-411 (1993).
Bruggemann, et al. "Production of human antibody repertoires in transgenic mice." *Curr Opin Biotechnol* 8(4): 455-458 (1997).
Bruggemann, et al. "Human antibody production in transgenic mice: expression from 100 kb of the human IgH locus." *Eur J Immunol* 21(5): 1323-1326 (1991).

(Continued)

*Primary Examiner* — Ruixiang Li
(74) *Attorney, Agent, or Firm* — Kirk Baumeister

(57) ABSTRACT

The present invention relates to engineered anti-TNFR superfamily member antibodies having enhanced agonistic activity and methods of using them.

13 Claims, 22 Drawing Sheets

Specification includes a Sequence Listing.

(56) References Cited

FOREIGN PATENT DOCUMENTS

| | | | |
|---|---|---|---|
| WO | WO1992/01047 | A1 | 1/1992 |
| WO | WO1992/22653 | A1 | 12/1992 |
| WO | WO1994/13804 | A1 | 6/1994 |
| WO | WO1998/44001 | A1 | 10/1998 |
| WO | WO99/45962 | A1 | 9/1999 |
| WO | WO2001/056603 | A1 | 8/2001 |
| WO | WO2001/083755 | A2 | 11/2001 |
| WO | WO2002/43478 | A2 | 6/2002 |
| WO | WO2002/066630 | A1 | 8/2002 |
| WO | WO2005/007190 | A1 | 1/2005 |
| WO | WO 2006/028936 | | 3/2006 |
| WO | WO2007/133822 | A1 | 11/2007 |
| WO | WO2008/077546 | A1 | 7/2008 |
| WO | WO2009/018386 | A1 | 2/2009 |
| WO | WO2009/080251 | A1 | 7/2009 |
| WO | WO2009/080252 | A1 | 7/2009 |
| WO | WO2009/080254 | A1 | 7/2009 |
| WO | WO2009/085462 | A1 | 7/2009 |
| WO | WO2011/028683 | A1 | 3/2011 |
| WO | WO2011/066501 | A1 | 6/2011 |
| WO | WO2011/131746 | A2 | 10/2011 |
| WO | WO 2013/004842 | A2 | 1/2013 |
| WO | WO2013/028231 | A1 | 2/2013 |
| WO | WO2013/034904 | A1 | 3/2013 |
| WO | WO2013/039954 | A1 | 3/2013 |
| WO | WO2014/070934 | A1 | 5/2014 |
| WO | WO 2014/108198 | A1 | 7/2014 |
| WO | WO 2014/148895 | A1 | 9/2014 |
| WO | WO 2014/198817 | A1 | 12/2014 |
| WO | WO 2016/066708 | A1 | 5/2016 |
| WO | WO 2016/164480 | A1 | 10/2016 |
| WO | WO 2017/093448 | A1 | 6/2017 |

OTHER PUBLICATIONS

Bruhns, et al. "Specificity and affinity of human Fcgamma receptors and their polymorphic variants for human IgG subclasses." *Blood* 113(16): 3716-3725 (2009).

Bulliard, et al. "OX40 engagement depletes intratumoral Tregs via activating FcgammaRs, leading to antitumor efficacy." *Immunol Cell Biol* 92(6): 475-480 (2014).

Bulliard, et al. "Activating Fc gamma receptors contribute to the antitumor activities of immunoregulatory receptor-targeting antibodies." *J Exp Med* 210(9): 1685-1693 (2013).

Cai, et al. "C-terminal lysine processing of human immunoglobulin G2 heavy chain in vivo." *Biotechnol Bioeng* 108(2): 404-412 2011).

Chen, et al. "Molecular mechanisms of T cell co-stimulation and co-inhibition." *Nat Rev Immunol* 13(4): 227-242 (2013).

Chu, et al. "Inhibition of B cell receptor-mediated activation of primary human B cells by coengagement of CD19 and FcgammaRIIb with Fc-engineered antibodies." *Mol Immunol* 45(15): 3926-3933 (2008).

Clackson, et al. "Making antibody fragments using phage display libraries." *Nature* 352(6336): 624-628 (1991).

Chothia, et al. "Canonical structures for the hypervariable regions of immunoglobulins." *J Mol Biol* 196(4): 901-917 (1987).

Dall'Acqua, et al. "Properties of human IgG1s engineered for enhanced binding to the neonatal Fc receptor (FcRn)." *J Biol Chem* 281(33): 23514-23524 (2006).

Datta-Mannan, et al. "Humanized IgG1 variants with differential binding properties to the neonatal Fc receptor: relationship to pharmacokinetics in mice and primates." *Drug Metab Dispos* 35(1): 86-94 (2007).

De Jong, et al. "A Novel Platform for the Potentiation of Therapeutic Antibodies Based on Antigen-Dependent Formation of IgG Hexamers at the Cell Surface," PLOS Biology, 14 (1): E1002344 (2016).

Diebolder, et al. "Complement is activated by IgG hexamers assembled at the cell surface." *Science* 343(6176): 1260-1263 (2014).

Ferrara, et al. "The carbohydrate at FcgammaRIIIa Asn-162. An element required for high affinity binding to non-fucosylated IgG glycoforms." *J Biol Chem* 281(8): 5032-5036 (2006).

Ferrara, et al. "Modulation of therapeutic antibody effector functions by glycosylation engineering: influence of Golgi enzyme localization domain and co-expression of heterologous beta1, 4-N-acetylglucosaminyltransferase III and Golgi alpha-mannosidase II." *Biotechnol Bioeng* 93(5): 851-861 (2006).

Fishwild, et al. "High-avidity human IgG kappa monoclonal antibodies from a novel strain of minilocus transgenic mice." *Nat Biotechnol* 14(7): 845-851 (1996).

Ghevaert, et al. "Developing recombinant HPA-1a-specific antibodies with abrogated Fcgamma receptor binding for the treatment of fetomaternal alloimmune thrombocytopenia." *J Clin Invest* 118(8): 2929-2938 (2008).

Goding, Monoclonal Antibodies: Principles and Practice, pp. 59-103, Academic Press, 1986.

Gramaglia, et al. "Ox-40 ligand: a potent costimulatory molecule for sustaining primary CD4 T cell responses." J *Immunol* 161(12): 6510-6517 (1998).

Green, et al. "Regulation of B cell development by variable gene complexity in mice reconstituted with human immunoglobulin yeast artificial chromosomes." *J Exp Med* 188(3): 483-495 (1998).

Green, L. L. "Antibody engineering via genetic engineering of the mouse: XenoMouse strains are a vehicle for the facile generation of therapeutic human monoclonal antibodies." *J Immunol Methods* 231(1-2): 11-23 (1999).

Green, et al. (1994). "Antigen-specific human monoclonal antibodies from mice engineered with human Ig heavy and light chain YACs." *Nat Genet* 7(1): 13-21 (1994).

Guanbo, et al., "Molecular Basis of Assembly and Activation of Complement Component C1 in Complex with Immunoglobulin G1 and Antigen," Molecular Cell, 63 (1): 135-145 (2016). * From EP Search Report.

Guilliams, et al. "The function of Fcgamma receptors in dendritic cells and macrophages." *Nat Rev Immunol* 14(2): 94-108 (2014).

Gupta, et al. "Development of a multidose formulation for a humanized monoclonal antibody using experimental design techniques." *AAPS PharmSci.* 5E8: (2003).

He, et al. "Agonist anti-human CD27 monoclonal antibody induces T cell activation and tumor immunity in human CD27-transgenic mice." *J Immunol* 191(8): 4174-4183 (2013).

Hinton, et al. "Engineered human IgG antibodies with longer serum half-lives in primates." *J Biol Chem* 279(8): 6213-6216 (2004).

Hinton, et al. "An engineered human IgG1 antibody with longer serum half-life." *J Immunol* 176(1): 346-356 (2006).

Idusogie, et al. "Engineered antibodies with increased activity to recruit complement." *J Immunol* 166(4): 2571-5 (2001).

Indik, et al. "The molecular dissection of Fc gamma receptor mediated phagocytosis." *Blood* 86(12): 4389-4399 (1995).

Kanamaru, et al. "Costimulation via glucocorticoid-induced TNF receptor in both conventional and CD25+ regulatory CD4+ T cells." *J Immunol* 172(12): 7306-7314 (2004).

Kim, et al. "Mapping the site on human IgG for binding of the MHC class I-related receptor, FcRn." *Eur J Immunol* 29(9): 2819-2825 (1999).

Knappik, et al. "Fully synthetic human combinatorial antibody libraries (HuCAL) based on modular consensus frameworks and CDRs randomized with trinucleotides." *J Mol Biol* 296(1): 57-86 (2000).

Knight, et al. "Pharmacodynamic enhancement of the anti-platelet antibody fab abciximab by site-specific pegylation." *Platelets* 15(7): 409-418 (2004).

Kohler and Milstein, "Continuous cultures of fused cells secreting antibody of predefined specificity," *Nature* 256:495-497 (1975).

Konno, et al. "Fucose content of monoclonal antibodies can be controlled by culture medium osmolality for high antibody-dependent cellular cytotoxicity." *Cytotechnology* 64(3): 249-265 (2012).

Krebs, et al. "High-throughput generation and engineering of recombinant human antibodies." *J Immunol Methods* 254(1-2): 67-84 (2001).

(56) References Cited

OTHER PUBLICATIONS

Lazar, et al. "Engineered antibody Fc variants with enhanced effector function." *Proc Natl Acad Sci U S A* 103(11): 4005-4010 (2006).
Lefranc, et al. "IMGT unique numbering for immunoglobulin and T cell receptor variable domains and Ig superfamily V-like domains." *Dev Comp Immunol* 27(1): 55-77 (2003).
Leong, et al. "Adapting pharmacokinetic properties of a humanized anti-interleukin-8 antibody for therapeutic applications using site-specific pegylation." *Cytokine* 16(3): 106-119 (2001).
Li, et al. "A general requirement for FcgammaRIIB co-engagement of agonistic anti-TNFR antibodies." *Cell Cycle* 11(18): 3343-3344 (2012).
Li, et al. "Inhibitory Fcgamma receptor engagement drives adjuvant and anti-tumor activities of agonistic CD40 antibodies." *Science* 333(6045): 1030-1034 (2011).
Li, et al. "Apoptotic and antitumor activity of death receptor antibodies require inhibitory Fcgamma receptor engagement." *Proc Natl Acad Sci U S A* 109(27): 10966-10971 (2012).
Lonberg, et al. "Human antibodies from transgenic mice." *Int Rev Immunol* 13(1): 65-93 (1995).
Lonberg, et al. "Antigen-specific human antibodies from mice comprising four distinct genetic modifications." *Nature* 368(6474): 856-859 (1994).
Luo, et al. "Dimers and multimers of monoclonal IgG1 exhibit higher in vitro binding affinities to Fcgamma receptors." *MAbs* 1(5): 491-504 (2009).
Maa, et al. "Aggregation of recombinant human growth hormone induced by phenolic compounds." *Int. J. Pharm.* 140: 155-168 (1996).
MacLennan, et al. "Structure-function relationships in the Ca(2+)-binding and translocation domain of SERCA1: physiological correlates in Brody disease." *Acta Physiol Scand Suppl* 643: 55-67 (1998).
Mangsbo, et al. "The human agonistic CD40 antibody ADC-1013 eradicates bladder tumors and generates T-cell-dependent tumor immunity." *Clin Cancer Res* 21(5): 1115-1126 (2015).
Marks, et al. "By-passing immunization. Human antibodies from V-gene libraries displayed on phage." *J Mol Biol* 222(3): 581-597 (1991).
Mellman, et al. "Cancer immunotherapy comes of age." *Nature* 480(7378): 480-489 (2011).
Mendez, et al. "Functional transplant of megabase human immunoglobulin loci recapitulates human antibody response in mice." *Nat Genet* 15(2): 146-156 (1997).
Mimoto, et al. "Engineered antibody Fc variant with selectively enhanced FcgammaRIIb binding over both FcgammaRIIa(R131) and FcgammaRIIa(H131)." *Protein Eng Des Sel* 26(10): 589-598 (2013).
Moore, et al. "Engineered Fc variant antibodies with enhanced ability to recruit complement and mediate effector functions." *MAbs* 2(2): 181-189 (2010).
Mori, et al. "Engineering Chinese hamster ovary cells to maximize effector function of produced antibodies using FUT8 siRNA." *Biotechnol Bioeng* 88(7): 901-908 (2004).
Morris, et al. "Development and characterization of recombinant human Fc:OX40L fusion protein linked via a coiled-coil trimerization domain." *Mol Immunol* 44(12): 3112-3121 (2007).
Olivier, et al. "EB66 cell line, a duck embryonic stem cell-derived substrate for the industrial production of therapeutic monoclonal antibodies with enhanced ADCC activity." *MAbs* 2(4): 405-415 (2010).
Padlan, E. A. "A possible procedure for reducing the immunogenicity of antibody variable domains while preserving their ligand-binding properties." *Mol Immunol* 28(4-5): 489-498 (1991).
Petkova, et al. "Enhanced half-life of genetically engineered human IgG1 antibodies in a humanized FcRn mouse model: potential application in humorally mediated autoimmune disease." *Int Immunol* 18(12): 1759-1769 (2006).
Pollok, et al. "Inducible T cell antigen 4-1BB. Analysis of expression and function." *J Immunol* 150(3): 771-781 (1993).
Ramakrishna, et al. "Characterization of the human T cell response to in vitro CD27 costimulation with varlilumab." *J Immunother Cancer* 3: 37 (2015).
Rankin, et al. "CD32B, the human inhibitory Fc-gamma receptor IIB, as a target for monoclonal antibody therapy of B-cell lymphoma." *Blood* 108(7): 2384-2391 (2006).
Remmele, et al. "Differential scanning calorimetry: A practical tool for elucidating stability of liquid biopharmaceuticals." *Biopharm*, 13: 36-46 (2000).
Remmele, et al. "Interleukin-1 receptor (IL-1R) liquid formulation development using differential scanning calorimetry," *Pharm. Res.* 15: 200-208 1997).
Richards, et al. "Optimization of antibody binding to FcgammaRIIa enhances macrophage phagocytosis of tumor cells." *Mol Cancer Ther* 7(8): 2517-2527 (2008).
Rother, et al. "Discovery and development of the complement inhibitor eculizumab for the treatment of paroxysmal nocturnal hemoglobinuria." *Nat Biotechnol* 25(11): 1256-1264 (2007).
Sasaki, et al. "Structure-mutation analysis of the ATPase site of Dictyostelium discoideum myosin II." *Adv Biophys* 35: 1-24 (1998).
Schaer, et al. "Targeting tumor-necrosis factor receptor pathways for tumor immunotherapy." *J Immunother Cancer* 2: 7 (2014).
Sheets, et al. "Efficient construction of a large nonimmune phage antibody library: the production of high-affinity human single-chain antibodies to protein antigens." *Proc Natl Acad Sci U S A* 95(11): 6157-6162 (1998).
Shi, et al. "De novo selection of high-affinity antibodies from synthetic fab libraries displayed on phage as pIX fusion proteins." *J Mol Biol* 397(2): 385-396 (2010).
Shields, et al. "High resolution mapping of the binding site on human IgG1 for Fc gamma RI, Fc gamma RII, Fc gamma RIII, and FcRn and design of IgG1 variants with improved binding to the Fc gamma R." *J Biol Chem* 276(9): 6591-6604 (2001).
Shields, et al. "Lack of fucose on human IgG1 N-linked oligosaccharide improves binding to human Fcgamma RIII and antibody-dependent cellular toxicity." *J Biol Chem* 277(30): 26733-26740 (2002).
Shinkawa, et al. "The absence of fucose but not the presence of galactose or bisecting N-acetylglucosamine of human IgG1 complex-type oligosaccharides shows the critical role of enhancing antibody-dependent cellular cytotoxicity." *J Biol Chem* 278(5): 3466-3473 (2003).
Stavenhagen, et al. "Fc optimization of therapeutic antibodies enhances their ability to kill tumor cells in vitro and controls tumor expansion in vivo via low-affinity activating Fcgamma receptors." *Cancer Res* 67(18): 8882-8890 (2007).
Vaccaro, et al. "Engineering the Fc region of immunoglobulin G to modulate in vivo antibody levels." *Nat Biotechnol* 23(10): 1283-1288 (2005).
Vaughan, et al. "Human antibodies with sub-nanomolar affinities isolated from a large non-immunized phage display library." *Nat Biotechnol* 14(3): 309-314 (1996).
Veri, et al. "Monoclonal antibodies capable of discriminating the human inhibitory Fcgamma-receptor IIB (CD32B) from the activating Fcgamma-receptor IIA (CD32A): biochemical, biological and functional characterization." *Immunology* 121(3): 392-404 (2007).
White, et al. "Conformation of the human immunoglobulin g2 hinge imparts superagonistic properties to immunostimulatory anticancer antibodies." *Cancer Cell* 27(1): 138-148 (2015).
White, et al. "FcgammaRIotaIotaB controls the potency of agonistic anti-TNFR mAbs." *Cancer Immunol Immunother* 62(5): 941-948 (2013).
Wilson, et al. "An Fcgamma receptor-dependent mechanism drives antibody-mediated target-receptor signaling in cancer cells." *Cancer Cell* 19(1): 101-113 (2011).
Worn, et al. "Stability engineering of antibody single-chain Fv fragments." *J Mol Biol* 305(5): 989-1010 (2001).
Wranik, et al. "LUZ-Y, a novel platform for the mammalian cell production of full-length IgG-bispecific antibodies." *J Biol Chem* 287(52): 43331-43339 (2012).

(56) References Cited

OTHER PUBLICATIONS

Wu, et al. "An analysis of the sequences of the variable regions of Bence Jones proteins and myeloma light chains and their implications for antibody complementarity." *J Exp Med* 132(2): 211-250 (1970).

Xu, et al. "In vitro characterization of five humanized OKT3 effector function variant antibodies." *Cell Immunol* 200(1): 16-26 (2000).

Xu, et al. "Fc gamma Rs modulate cytotoxicity of anti-Fas antibodies: implications for agonistic antibody-based therapeutics." *J Immunol* 171(2): 562-568 (2003).

Yang, et al. "Eradication of established tumors by a fully human monoclonal antibody to the epidermal growth factor receptor without concomitant chemotherapy." *Cancer Res* 59(6): 1236-1243 (1999).

Yang, et al. "Tailoring structure-function and pharmacokinetic properties of single-chain Fv proteins by site-specific PEGylation." *Protein Eng* 16(10): 761-770 (2003).

Yeung, et al. "A therapeutic anti-VEGF antibody with increased potency independent of pharmacokinetic half-life." *Cancer Res* 70(8): 3269-3277 (2010).

Zalevsky, et al. "Enhanced antibody half-life improves in vivo activity." *Nat Biotechnol* 28(2): 157-159 (2010).

Zhang, et al., "Fc Engineering Approaches to Enhance the Agonism and Effector Functions of an Anti-OX40 Antibody," Journal of Biological Chemistry, 291 (53): 27134-27146 (2016). * From EP Search Report.

Zhang, et al. "Mechanism for benzyl alcohol-induced aggregation of recombinant human interleukin-1 receptor antagonist in aqueous solution." *J. Pharm. Sci.* 93: 3076-3089 (2004).

Zhang, et al., "Functional optimization of agonistic antibodies to OX40 receptor with novel Fc mutations to promote antibody multimerization," MABS, 9 (7): 1129-1142 (2017). * From EP Search Report.

Zhou, et al. "Development of a simple and rapid method for producing non-fucosylated oligomannose containing antibodies with increased effector function." *Biotechnol Bioeng* 99(3): 652-665 (2008).

Intellectual Property Office of Singapore Search Report dated Jun. 23, 2020.

H. Wajant, "Principles of antibody-mediated TNF receptor activation," Cell Death & Differentiation, 22(11): 1727-1741 (2015),.

* cited by examiner

SEQUENCE LISTING

```
<160> NUMBER OF SEQ ID NOS: 67

<210> SEQ ID NO 1
<211> LENGTH: 455
<212> TYPE: PRT
<213> ORGANISM: Homo sapiens

<400> SEQUENCE: 1

Met Gly Leu Ser Thr Val Pro Asp Leu Leu Leu Pro Leu Val Leu Leu
1               5                   10                  15

Glu Leu Leu Val Gly Ile Tyr Pro Ser Gly Val Ile Gly Leu Val Pro
            20                  25                  30

His Leu Gly Asp Arg Glu Lys Arg Asp Ser Val Cys Pro Gln Gly Lys
        35                  40                  45

Tyr Ile His Pro Gln Asn Asn Ser Ile Cys Cys Thr Lys Cys His Lys
    50                  55                  60

Gly Thr Tyr Leu Tyr Asn Asp Cys Pro Gly Pro Gly Gln Asp Thr Asp
```

```
65                  70                  75                  80

Cys Arg Glu Cys Glu Ser Gly Ser Phe Thr Ala Ser Glu Asn His Leu
                85                  90                  95

Arg His Cys Leu Ser Cys Ser Lys Cys Arg Lys Glu Met Gly Gln Val
            100                 105                 110

Glu Ile Ser Ser Cys Thr Val Asp Arg Asp Thr Val Cys Gly Cys Arg
        115                 120                 125

Lys Asn Gln Tyr Arg His Tyr Trp Ser Glu Asn Leu Phe Gln Cys Phe
    130                 135                 140

Asn Cys Ser Leu Cys Leu Asn Gly Thr Val His Leu Ser Cys Gln Glu
145                 150                 155                 160

Lys Gln Asn Thr Val Cys Thr Cys His Ala Gly Phe Phe Leu Arg Glu
                165                 170                 175

Asn Glu Cys Val Ser Cys Ser Asn Cys Lys Lys Ser Leu Glu Cys Thr
            180                 185                 190

Lys Leu Cys Leu Pro Gln Ile Glu Asn Val Lys Gly Thr Glu Asp Ser
        195                 200                 205

Gly Thr Thr Val Leu Leu Pro Leu Val Ile Phe Phe Gly Leu Cys Leu
    210                 215                 220

Leu Ser Leu Leu Phe Ile Gly Leu Met Tyr Arg Tyr Gln Arg Trp Lys
225                 230                 235                 240

Ser Lys Leu Tyr Ser Ile Val Cys Gly Lys Ser Thr Pro Glu Lys Glu
                245                 250                 255

Gly Glu Leu Glu Gly Thr Thr Thr Lys Pro Leu Ala Pro Asn Pro Ser
            260                 265                 270

Phe Ser Pro Thr Pro Gly Phe Thr Pro Thr Leu Gly Phe Ser Pro Val
        275                 280                 285

Pro Ser Ser Thr Phe Thr Ser Ser Ser Thr Tyr Thr Pro Gly Asp Cys
    290                 295                 300

Pro Asn Phe Ala Ala Pro Arg Arg Glu Val Ala Pro Pro Tyr Gln Gly
305                 310                 315                 320

Ala Asp Pro Ile Leu Ala Thr Ala Leu Ala Ser Asp Pro Ile Pro Asn
                325                 330                 335

Pro Leu Gln Lys Trp Glu Asp Ser Ala His Lys Pro Gln Ser Leu Asp
            340                 345                 350

Thr Asp Asp Pro Ala Thr Leu Tyr Ala Val Val Glu Asn Val Pro Pro
        355                 360                 365

Leu Arg Trp Lys Glu Phe Val Arg Arg Leu Gly Leu Ser Asp His Glu
    370                 375                 380

Ile Asp Arg Leu Glu Leu Gln Asn Gly Arg Cys Leu Arg Glu Ala Gln
385                 390                 395                 400

Tyr Ser Met Leu Ala Thr Trp Arg Arg Arg Thr Pro Arg Arg Glu Ala
                405                 410                 415

Thr Leu Glu Leu Leu Gly Arg Val Leu Arg Asp Met Asp Leu Leu Gly
            420                 425                 430

Cys Leu Glu Asp Ile Glu Glu Ala Leu Cys Gly Pro Ala Ala Leu Pro
        435                 440                 445

Pro Ala Pro Ser Leu Leu Arg
    450                 455
```

<210> SEQ ID NO 2
<211> LENGTH: 461
<212> TYPE: PRT
<213> ORGANISM: Homo sapiens

<400> SEQUENCE: 2

```
Met Ala Pro Val Ala Val Trp Ala Ala Leu Ala Val Gly Leu Glu Leu
1               5                   10                  15

Trp Ala Ala Ala His Ala Leu Pro Ala Gln Val Ala Phe Thr Pro Tyr
            20                  25                  30

Ala Pro Glu Pro Gly Ser Thr Cys Arg Leu Arg Glu Tyr Tyr Asp Gln
        35                  40                  45

Thr Ala Gln Met Cys Cys Ser Lys Cys Ser Pro Gly Gln His Ala Lys
    50                  55                  60

Val Phe Cys Thr Lys Thr Ser Asp Thr Val Cys Asp Ser Cys Glu Asp
65                  70                  75                  80

Ser Thr Tyr Thr Gln Leu Trp Asn Trp Val Pro Glu Cys Leu Ser Cys
                85                  90                  95

Gly Ser Arg Cys Ser Ser Asp Gln Val Glu Thr Gln Ala Cys Thr Arg
            100                 105                 110

Glu Gln Asn Arg Ile Cys Thr Cys Arg Pro Gly Trp Tyr Cys Ala Leu
        115                 120                 125

Ser Lys Gln Glu Gly Cys Arg Leu Cys Ala Pro Leu Arg Lys Cys Arg
    130                 135                 140

Pro Gly Phe Gly Val Ala Arg Pro Gly Thr Glu Thr Ser Asp Val Val
145                 150                 155                 160

Cys Lys Pro Cys Ala Pro Gly Thr Phe Ser Asn Thr Thr Ser Ser Thr
                165                 170                 175

Asp Ile Cys Arg Pro His Gln Ile Cys Asn Val Val Ala Ile Pro Gly
            180                 185                 190

Asn Ala Ser Met Asp Ala Val Cys Thr Ser Thr Ser Pro Thr Arg Ser
        195                 200                 205

Met Ala Pro Gly Ala Val His Leu Pro Gln Pro Val Ser Thr Arg Ser
    210                 215                 220

Gln His Thr Gln Pro Thr Pro Glu Pro Ser Thr Ala Pro Ser Thr Ser
225                 230                 235                 240

Phe Leu Leu Pro Met Gly Pro Ser Pro Pro Ala Glu Gly Ser Thr Gly
                245                 250                 255

Asp Phe Ala Leu Pro Val Gly Leu Ile Val Gly Val Thr Ala Leu Gly
            260                 265                 270

Leu Leu Ile Ile Gly Val Val Asn Cys Val Ile Met Thr Gln Val Lys
        275                 280                 285

Lys Lys Pro Leu Cys Leu Gln Arg Glu Ala Lys Val Pro His Leu Pro
    290                 295                 300

Ala Asp Lys Ala Arg Gly Thr Gln Gly Pro Glu Gln Gln His Leu Leu
305                 310                 315                 320

Ile Thr Ala Pro Ser Ser Ser Ser Ser Ser Leu Glu Ser Ser Ala Ser
                325                 330                 335

Ala Leu Asp Arg Arg Ala Pro Thr Arg Asn Gln Pro Gln Ala Pro Gly
            340                 345                 350

Val Glu Ala Ser Gly Ala Gly Glu Ala Arg Ala Ser Thr Gly Ser Ser
        355                 360                 365

Asp Ser Ser Pro Gly Gly His Gly Thr Gln Val Asn Val Thr Cys Ile
    370                 375                 380

Val Asn Val Cys Ser Ser Ser Asp His Ser Ser Gln Cys Ser Ser Gln
385                 390                 395                 400

Ala Ser Ser Thr Met Gly Asp Thr Asp Ser Ser Pro Ser Glu Ser Pro
```

```
                405                 410                 415

Lys Asp Glu Gln Val Pro Phe Ser Lys Glu Glu Cys Ala Phe Arg Ser
            420                 425                 430

Gln Leu Glu Thr Pro Glu Thr Leu Leu Gly Ser Thr Glu Glu Lys Pro
        435                 440                 445

Leu Pro Leu Gly Val Pro Asp Ala Gly Met Lys Pro Ser
    450                 455                 460


<210> SEQ ID NO 3
<211> LENGTH: 769
<212> TYPE: PRT
<213> ORGANISM: Homo sapiens

<400> SEQUENCE: 3

Met Leu Gly Leu Arg Pro Pro Leu Leu Ala Leu Val Gly Leu Leu Ser
1               5                   10                  15

Leu Gly Cys Val Leu Ser Gln Glu Cys Thr Lys Phe Lys Val Ser Ser
            20                  25                  30

Cys Arg Glu Cys Ile Glu Ser Gly Pro Gly Cys Thr Trp Cys Gln Lys
        35                  40                  45

Leu Asn Phe Thr Gly Pro Gly Asp Pro Asp Ser Ile Arg Cys Asp Thr
    50                  55                  60

Arg Pro Gln Leu Leu Met Arg Gly Cys Ala Ala Asp Asp Ile Met Asp
65                  70                  75                  80

Pro Thr Ser Leu Ala Glu Thr Gln Glu Asp His Asn Gly Gly Gln Lys
                85                  90                  95

Gln Leu Ser Pro Gln Lys Val Thr Leu Tyr Leu Arg Pro Gly Gln Ala
            100                 105                 110

Ala Ala Phe Asn Val Thr Phe Arg Arg Ala Lys Gly Tyr Pro Ile Asp
        115                 120                 125

Leu Tyr Tyr Leu Met Asp Leu Ser Tyr Ser Met Leu Asp Asp Leu Arg
    130                 135                 140

Asn Val Lys Lys Leu Gly Gly Asp Leu Leu Arg Ala Leu Asn Glu Ile
145                 150                 155                 160

Thr Glu Ser Gly Arg Ile Gly Phe Gly Ser Phe Val Asp Lys Thr Val
                165                 170                 175

Leu Pro Phe Val Asn Thr His Pro Asp Lys Leu Arg Asn Pro Cys Pro
            180                 185                 190

Asn Lys Glu Lys Glu Cys Gln Pro Pro Phe Ala Phe Arg His Val Leu
        195                 200                 205

Lys Leu Thr Asn Asn Ser Asn Gln Phe Gln Thr Glu Val Gly Lys Gln
    210                 215                 220

Leu Ile Ser Gly Asn Leu Asp Ala Pro Glu Gly Gly Leu Asp Ala Met
225                 230                 235                 240

Met Gln Val Ala Ala Cys Pro Glu Glu Ile Gly Trp Arg Asn Val Thr
                245                 250                 255

Arg Leu Leu Val Phe Ala Thr Asp Asp Gly Phe His Phe Ala Gly Asp
            260                 265                 270

Gly Lys Leu Gly Ala Ile Leu Thr Pro Asn Asp Gly Arg Cys His Leu
        275                 280                 285

Glu Asp Asn Leu Tyr Lys Arg Ser Asn Glu Phe Asp Tyr Pro Ser Val
    290                 295                 300

Gly Gln Leu Ala His Lys Leu Ala Glu Asn Asn Ile Gln Pro Ile Phe
305                 310                 315                 320
```

```
Ala Val Thr Ser Arg Met Val Lys Thr Tyr Glu Lys Leu Thr Glu Ile
                325                 330                 335

Ile Pro Lys Ser Ala Val Gly Glu Leu Ser Glu Asp Ser Ser Asn Val
            340                 345                 350

Val Gln Leu Ile Lys Asn Ala Tyr Asn Lys Leu Ser Ser Arg Val Phe
        355                 360                 365

Leu Asp His Asn Ala Leu Pro Asp Thr Leu Lys Val Thr Tyr Asp Ser
    370                 375                 380

Phe Cys Ser Asn Gly Val Thr His Arg Asn Gln Pro Arg Gly Asp Cys
385                 390                 395                 400

Asp Gly Val Gln Ile Asn Val Pro Ile Thr Phe Gln Val Lys Val Thr
                405                 410                 415

Ala Thr Glu Cys Ile Gln Glu Gln Ser Phe Val Ile Arg Ala Leu Gly
            420                 425                 430

Phe Thr Asp Ile Val Thr Val Gln Val Leu Pro Gln Cys Glu Cys Arg
        435                 440                 445

Cys Arg Asp Gln Ser Arg Asp Arg Ser Leu Cys His Gly Lys Gly Phe
    450                 455                 460

Leu Glu Cys Gly Ile Cys Arg Cys Asp Thr Gly Tyr Ile Gly Lys Asn
465                 470                 475                 480

Cys Glu Cys Gln Thr Gln Gly Arg Ser Ser Gln Glu Leu Glu Gly Ser
                485                 490                 495

Cys Arg Lys Asp Asn Asn Ser Ile Ile Cys Ser Gly Leu Gly Asp Cys
            500                 505                 510

Val Cys Gly Gln Cys Leu Cys His Thr Ser Asp Val Pro Gly Lys Leu
        515                 520                 525

Ile Tyr Gly Gln Tyr Cys Glu Cys Asp Thr Ile Asn Cys Glu Arg Tyr
    530                 535                 540

Asn Gly Gln Val Cys Gly Gly Pro Gly Arg Gly Leu Cys Phe Cys Gly
545                 550                 555                 560

Lys Cys Arg Cys His Pro Gly Phe Glu Gly Ser Ala Cys Gln Cys Glu
                565                 570                 575

Arg Thr Thr Glu Gly Cys Leu Asn Pro Arg Arg Val Glu Cys Ser Gly
            580                 585                 590

Arg Gly Arg Cys Arg Cys Asn Val Cys Glu Cys His Ser Gly Tyr Gln
        595                 600                 605

Leu Pro Leu Cys Gln Glu Cys Pro Gly Cys Pro Ser Pro Cys Gly Lys
    610                 615                 620

Tyr Ile Ser Cys Ala Glu Cys Leu Lys Phe Glu Lys Gly Pro Phe Gly
625                 630                 635                 640

Lys Asn Cys Ser Ala Ala Cys Pro Gly Leu Gln Leu Ser Asn Asn Pro
                645                 650                 655

Val Lys Gly Arg Thr Cys Lys Glu Arg Asp Ser Glu Gly Cys Trp Val
            660                 665                 670

Ala Tyr Thr Leu Glu Gln Gln Asp Gly Met Asp Arg Tyr Leu Ile Tyr
        675                 680                 685

Val Asp Glu Ser Arg Glu Cys Val Ala Gly Pro Asn Ile Ala Ala Ile
    690                 695                 700

Val Gly Gly Thr Val Ala Gly Ile Val Leu Ile Gly Ile Leu Leu Leu
705                 710                 715                 720

Val Ile Trp Lys Ala Leu Ile His Leu Ser Asp Leu Arg Glu Tyr Arg
                725                 730                 735

Arg Phe Glu Lys Glu Lys Leu Lys Ser Gln Trp Asn Asn Asp Asn Pro
```

```
            740                 745                 750

Leu Phe Lys Ser Ala Thr Thr Thr Val Met Asn Pro Lys Phe Ala Glu
        755                 760                 765

Ser


<210> SEQ ID NO 4
<211> LENGTH: 277
<212> TYPE: PRT
<213> ORGANISM: Homo sapiens

<400> SEQUENCE: 4

Met Cys Val Gly Ala Arg Arg Leu Gly Arg Gly Pro Cys Ala Ala Leu
1               5                   10                  15

Leu Leu Leu Gly Leu Gly Leu Ser Thr Val Thr Gly Leu His Cys Val
            20                  25                  30

Gly Asp Thr Tyr Pro Ser Asn Asp Arg Cys Cys His Glu Cys Arg Pro
        35                  40                  45

Gly Asn Gly Met Val Ser Arg Cys Ser Arg Ser Gln Asn Thr Val Cys
    50                  55                  60

Arg Pro Cys Gly Pro Gly Phe Tyr Asn Asp Val Val Ser Ser Lys Pro
65                  70                  75                  80

Cys Lys Pro Cys Thr Trp Cys Asn Leu Arg Ser Gly Ser Glu Arg Lys
                85                  90                  95

Gln Leu Cys Thr Ala Thr Gln Asp Thr Val Cys Arg Cys Arg Ala Gly
            100                 105                 110

Thr Gln Pro Leu Asp Ser Tyr Lys Pro Gly Val Asp Cys Ala Pro Cys
        115                 120                 125

Pro Pro Gly His Phe Ser Pro Gly Asp Asn Gln Ala Cys Lys Pro Trp
    130                 135                 140

Thr Asn Cys Thr Leu Ala Gly Lys His Thr Leu Gln Pro Ala Ser Asn
145                 150                 155                 160

Ser Ser Asp Ala Ile Cys Glu Asp Arg Asp Pro Pro Ala Thr Gln Pro
                165                 170                 175

Gln Glu Thr Gln Gly Pro Pro Ala Arg Pro Ile Thr Val Gln Pro Thr
            180                 185                 190

Glu Ala Trp Pro Arg Thr Ser Gln Gly Pro Ser Thr Arg Pro Val Glu
        195                 200                 205

Val Pro Gly Gly Arg Ala Val Ala Ala Ile Leu Gly Leu Gly Leu Val
    210                 215                 220

Leu Gly Leu Leu Gly Pro Leu Ala Ile Leu Leu Ala Leu Tyr Leu Leu
225                 230                 235                 240

Arg Arg Asp Gln Arg Leu Pro Pro Asp Ala His Lys Pro Pro Gly Gly
                245                 250                 255

Gly Ser Phe Arg Thr Pro Ile Gln Glu Glu Gln Ala Asp Ala His Ser
            260                 265                 270

Thr Leu Ala Lys Ile
        275


<210> SEQ ID NO 5
<211> LENGTH: 277
<212> TYPE: PRT
<213> ORGANISM: Homo sapiens

<400> SEQUENCE: 5

Met Val Arg Leu Pro Leu Gln Cys Val Leu Trp Gly Cys Leu Leu Thr
1               5                   10                  15
```

```
Ala Val His Pro Glu Pro Pro Thr Ala Cys Arg Glu Lys Gln Tyr Leu
            20                  25                  30

Ile Asn Ser Gln Cys Cys Ser Leu Cys Gln Pro Gly Gln Lys Leu Val
        35                  40                  45

Ser Asp Cys Thr Glu Phe Thr Glu Thr Glu Cys Leu Pro Cys Gly Glu
    50                  55                  60

Ser Glu Phe Leu Asp Thr Trp Asn Arg Glu Thr His Cys His Gln His
65                  70                  75                  80

Lys Tyr Cys Asp Pro Asn Leu Gly Leu Arg Val Gln Gln Lys Gly Thr
                85                  90                  95

Ser Glu Thr Asp Thr Ile Cys Thr Cys Glu Glu Gly Trp His Cys Thr
            100                 105                 110

Ser Glu Ala Cys Glu Ser Cys Val Leu His Arg Ser Cys Ser Pro Gly
        115                 120                 125

Phe Gly Val Lys Gln Ile Ala Thr Gly Val Ser Asp Thr Ile Cys Glu
    130                 135                 140

Pro Cys Pro Val Gly Phe Phe Ser Asn Val Ser Ser Ala Phe Glu Lys
145                 150                 155                 160

Cys His Pro Trp Thr Ser Cys Glu Thr Lys Asp Leu Val Val Gln Gln
                165                 170                 175

Ala Gly Thr Asn Lys Thr Asp Val Val Cys Gly Pro Gln Asp Arg Leu
            180                 185                 190

Arg Ala Leu Val Val Ile Pro Ile Ile Phe Gly Ile Leu Phe Ala Ile
        195                 200                 205

Leu Leu Val Leu Val Phe Ile Lys Lys Val Ala Lys Lys Pro Thr Asn
    210                 215                 220

Lys Ala Pro His Pro Lys Gln Glu Pro Gln Glu Ile Asn Phe Pro Asp
225                 230                 235                 240

Asp Leu Pro Gly Ser Asn Thr Ala Ala Pro Val Gln Glu Thr Leu His
                245                 250                 255

Gly Cys Gln Pro Val Thr Gln Glu Asp Gly Lys Glu Ser Arg Ile Ser
            260                 265                 270

Val Gln Glu Arg Gln
        275


<210> SEQ ID NO 6
<211> LENGTH: 335
<212> TYPE: PRT
<213> ORGANISM: Homo sapiens

<400> SEQUENCE: 6

Met Leu Gly Ile Trp Thr Leu Leu Pro Leu Val Leu Thr Ser Val Ala
1               5                   10                  15

Arg Leu Ser Ser Lys Ser Val Asn Ala Gln Val Thr Asp Ile Asn Ser
            20                  25                  30

Lys Gly Leu Glu Leu Arg Lys Thr Val Thr Thr Val Glu Thr Gln Asn
        35                  40                  45

Leu Glu Gly Leu His His Asp Gly Gln Phe Cys His Lys Pro Cys Pro
    50                  55                  60

Pro Gly Glu Arg Lys Ala Arg Asp Cys Thr Val Asn Gly Asp Glu Pro
65                  70                  75                  80

Asp Cys Val Pro Cys Gln Glu Gly Lys Glu Tyr Thr Asp Lys Ala His
                85                  90                  95

Phe Ser Ser Lys Cys Arg Arg Cys Arg Leu Cys Asp Glu Gly His Gly
```

```
            100                 105                 110

Leu Glu Val Glu Ile Asn Cys Thr Arg Thr Gln Asn Thr Lys Cys Arg
        115                 120                 125

Cys Lys Pro Asn Phe Phe Cys Asn Ser Thr Val Cys Glu His Cys Asp
    130                 135                 140

Pro Cys Thr Lys Cys Glu His Gly Ile Ile Lys Glu Cys Thr Leu Thr
145                 150                 155                 160

Ser Asn Thr Lys Cys Lys Glu Glu Gly Ser Arg Ser Asn Leu Gly Trp
                165                 170                 175

Leu Cys Leu Leu Leu Leu Pro Ile Pro Leu Ile Val Trp Val Lys Arg
            180                 185                 190

Lys Glu Val Gln Lys Thr Cys Arg Lys His Arg Lys Glu Asn Gln Gly
        195                 200                 205

Ser His Glu Ser Pro Thr Leu Asn Pro Glu Thr Val Ala Ile Asn Leu
    210                 215                 220

Ser Asp Val Asp Leu Ser Lys Tyr Ile Thr Thr Ile Ala Gly Val Met
225                 230                 235                 240

Thr Leu Ser Gln Val Lys Gly Phe Val Arg Lys Asn Gly Val Asn Glu
                245                 250                 255

Ala Lys Ile Asp Glu Ile Lys Asn Asp Asn Val Gln Asp Thr Ala Glu
            260                 265                 270

Gln Lys Val Gln Leu Leu Arg Asn Trp His Gln Leu His Gly Lys Lys
        275                 280                 285

Glu Ala Tyr Asp Thr Leu Ile Lys Asp Leu Lys Lys Ala Asn Leu Cys
    290                 295                 300

Thr Leu Ala Glu Lys Ile Gln Thr Ile Ile Leu Lys Asp Ile Thr Ser
305                 310                 315                 320

Asp Ser Glu Asn Ser Asn Phe Arg Asn Glu Ile Gln Ser Leu Val
                325                 330                 335


<210> SEQ ID NO 7
<211> LENGTH: 74
<212> TYPE: PRT
<213> ORGANISM: Homo sapiens

<400> SEQUENCE: 7

Met Arg Ala Leu Glu Gly Pro Gly Leu Ser Leu Leu Cys Leu Val Leu
1               5                   10                  15

Ala Leu Pro Ala Leu Leu Pro Val Pro Ala Val Arg Gly Val Ala Glu
            20                  25                  30

Thr Pro Thr Tyr Pro Trp Arg Asp Ala Glu Thr Gly Glu Arg Leu Val
        35                  40                  45

Arg Leu Leu Gln Ala Leu Arg Val Ala Arg Met Pro Gly Leu Glu Arg
    50                  55                  60

Ser Val Arg Glu Arg Phe Leu Pro Val His
65                  70


<210> SEQ ID NO 8
<211> LENGTH: 260
<212> TYPE: PRT
<213> ORGANISM: Homo sapiens

<400> SEQUENCE: 8

Met Ala Arg Pro His Pro Trp Trp Leu Cys Val Leu Gly Thr Leu Val
1               5                   10                  15

Gly Leu Ser Ala Thr Pro Ala Pro Lys Ser Cys Pro Glu Arg His Tyr
```

```
            20                  25                  30

Trp Ala Gln Gly Lys Leu Cys Cys Gln Met Cys Glu Pro Gly Thr Phe
        35                  40                  45

Leu Val Lys Asp Cys Asp Gln His Arg Lys Ala Ala Gln Cys Asp Pro
    50                  55                  60

Cys Ile Pro Gly Val Ser Phe Ser Pro Asp His His Thr Arg Pro His
65                  70                  75                  80

Cys Glu Ser Cys Arg His Cys Asn Ser Gly Leu Leu Val Arg Asn Cys
                85                  90                  95

Thr Ile Thr Ala Asn Ala Glu Cys Ala Cys Arg Asn Gly Trp Gln Cys
            100                 105                 110

Arg Asp Lys Glu Cys Thr Glu Cys Asp Pro Leu Pro Asn Pro Ser Leu
        115                 120                 125

Thr Ala Arg Ser Ser Gln Ala Leu Ser Pro His Pro Gln Pro Thr His
    130                 135                 140

Leu Pro Tyr Val Ser Glu Met Leu Glu Ala Arg Thr Ala Gly His Met
145                 150                 155                 160

Gln Thr Leu Ala Asp Phe Arg Gln Leu Pro Ala Arg Thr Leu Ser Thr
                165                 170                 175

His Trp Pro Pro Gln Arg Ser Leu Cys Ser Ser Asp Phe Ile Arg Ile
            180                 185                 190

Leu Val Ile Phe Ser Gly Met Phe Leu Val Phe Thr Leu Ala Gly Ala
        195                 200                 205

Leu Phe Leu His Gln Arg Arg Lys Tyr Arg Ser Asn Lys Gly Glu Ser
    210                 215                 220

Pro Val Glu Pro Ala Glu Pro Cys His Tyr Ser Cys Pro Arg Glu Glu
225                 230                 235                 240

Glu Gly Ser Thr Ile Pro Ile Gln Glu Asp Tyr Arg Lys Pro Glu Pro
                245                 250                 255

Ala Cys Ser Pro
            260


<210> SEQ ID NO 9
<211> LENGTH: 595
<212> TYPE: PRT
<213> ORGANISM: Homo sapiens

<400> SEQUENCE: 9

Met Arg Val Leu Leu Ala Ala Leu Gly Leu Leu Phe Leu Gly Ala Leu
1               5                   10                  15

Arg Ala Phe Pro Gln Asp Arg Pro Phe Glu Asp Thr Cys His Gly Asn
            20                  25                  30

Pro Ser His Tyr Tyr Asp Lys Ala Val Arg Arg Cys Cys Tyr Arg Cys
        35                  40                  45

Pro Met Gly Leu Phe Pro Thr Gln Gln Cys Pro Gln Arg Pro Thr Asp
    50                  55                  60

Cys Arg Lys Gln Cys Glu Pro Asp Tyr Tyr Leu Asp Glu Ala Asp Arg
65                  70                  75                  80

Cys Thr Ala Cys Val Thr Cys Ser Arg Asp Asp Leu Val Glu Lys Thr
                85                  90                  95

Pro Cys Ala Trp Asn Ser Ser Arg Val Cys Glu Cys Arg Pro Gly Met
            100                 105                 110

Phe Cys Ser Thr Ser Ala Val Asn Ser Cys Ala Arg Cys Phe Phe His
        115                 120                 125
```

```
Ser Val Cys Pro Ala Gly Met Ile Val Lys Phe Pro Gly Thr Ala Gln
    130                 135                 140

Lys Asn Thr Val Cys Glu Pro Ala Ser Pro Gly Val Ser Pro Ala Cys
145                 150                 155                 160

Ala Ser Pro Glu Asn Cys Lys Glu Pro Ser Ser Gly Thr Ile Pro Gln
                165                 170                 175

Ala Lys Pro Thr Pro Val Ser Pro Ala Thr Ser Ser Ala Ser Thr Met
            180                 185                 190

Pro Val Arg Gly Gly Thr Arg Leu Ala Gln Glu Ala Ala Ser Lys Leu
        195                 200                 205

Thr Arg Ala Pro Asp Ser Pro Ser Ser Val Gly Arg Pro Ser Ser Asp
    210                 215                 220

Pro Gly Leu Ser Pro Thr Gln Pro Cys Pro Glu Gly Ser Gly Asp Cys
225                 230                 235                 240

Arg Lys Gln Cys Glu Pro Asp Tyr Tyr Leu Asp Glu Ala Gly Arg Cys
                245                 250                 255

Thr Ala Cys Val Ser Cys Ser Arg Asp Asp Leu Val Glu Lys Thr Pro
            260                 265                 270

Cys Ala Trp Asn Ser Ser Arg Thr Cys Glu Cys Arg Pro Gly Met Ile
        275                 280                 285

Cys Ala Thr Ser Ala Thr Asn Ser Cys Ala Arg Cys Val Pro Tyr Pro
    290                 295                 300

Ile Cys Ala Ala Glu Thr Val Thr Lys Pro Gln Asp Met Ala Glu Lys
305                 310                 315                 320

Asp Thr Thr Phe Glu Ala Pro Pro Leu Gly Thr Gln Pro Asp Cys Asn
                325                 330                 335

Pro Thr Pro Glu Asn Gly Glu Ala Pro Ala Ser Thr Ser Pro Thr Gln
            340                 345                 350

Ser Leu Leu Val Asp Ser Gln Ala Ser Lys Thr Leu Pro Ile Pro Thr
        355                 360                 365

Ser Ala Pro Val Ala Leu Ser Ser Thr Gly Lys Pro Val Leu Asp Ala
    370                 375                 380

Gly Pro Val Leu Phe Trp Val Ile Leu Val Leu Val Val Val Val Gly
385                 390                 395                 400

Ser Ser Ala Phe Leu Leu Cys His Arg Arg Ala Cys Arg Lys Arg Ile
                405                 410                 415

Arg Gln Lys Leu His Leu Cys Tyr Pro Val Gln Thr Ser Gln Pro Lys
            420                 425                 430

Leu Glu Leu Val Asp Ser Arg Pro Arg Arg Ser Ser Thr Gln Leu Arg
        435                 440                 445

Ser Gly Ala Ser Val Thr Glu Pro Val Ala Glu Glu Arg Gly Leu Met
    450                 455                 460

Ser Gln Pro Leu Met Glu Thr Cys His Ser Val Gly Ala Ala Tyr Leu
465                 470                 475                 480

Glu Ser Leu Pro Leu Gln Asp Ala Ser Pro Ala Gly Gly Pro Ser Ser
                485                 490                 495

Pro Arg Asp Leu Pro Glu Pro Arg Val Ser Thr Glu His Thr Asn Asn
            500                 505                 510

Lys Ile Glu Lys Ile Tyr Ile Met Lys Ala Asp Thr Val Ile Val Gly
        515                 520                 525

Thr Val Lys Ala Glu Leu Pro Glu Gly Arg Gly Leu Ala Gly Pro Ala
    530                 535                 540

Glu Pro Glu Leu Glu Glu Glu Leu Glu Ala Asp His Thr Pro His Tyr
```

```
545                 550                 555                 560

Pro Glu Gln Glu Thr Glu Pro Pro Leu Gly Ser Cys Ser Asp Val Met
                565                 570                 575

Leu Ser Val Glu Glu Glu Gly Lys Glu Asp Pro Leu Pro Thr Ala Ala
            580                 585                 590

Ser Gly Lys
        595


<210> SEQ ID NO 10
<211> LENGTH: 255
<212> TYPE: PRT
<213> ORGANISM: Homo sapiens

<400> SEQUENCE: 10

Met Gly Asn Ser Cys Tyr Asn Ile Val Ala Thr Leu Leu Leu Val Leu
1               5                   10                  15

Asn Phe Glu Arg Thr Arg Ser Leu Gln Asp Pro Cys Ser Asn Cys Pro
            20                  25                  30

Ala Gly Thr Phe Cys Asp Asn Asn Arg Asn Gln Ile Cys Ser Pro Cys
        35                  40                  45

Pro Pro Asn Ser Phe Ser Ser Ala Gly Gly Gln Arg Thr Cys Asp Ile
    50                  55                  60

Cys Arg Gln Cys Lys Gly Val Phe Arg Thr Arg Lys Glu Cys Ser Ser
65                  70                  75                  80

Thr Ser Asn Ala Glu Cys Asp Cys Thr Pro Gly Phe His Cys Leu Gly
                85                  90                  95

Ala Gly Cys Ser Met Cys Glu Gln Asp Cys Lys Gln Gly Gln Glu Leu
            100                 105                 110

Thr Lys Lys Gly Cys Lys Asp Cys Cys Phe Gly Thr Phe Asn Asp Gln
        115                 120                 125

Lys Arg Gly Ile Cys Arg Pro Trp Thr Asn Cys Ser Leu Asp Gly Lys
    130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                165                 170                 175

Pro Ala Arg Glu Pro Gly His Ser Pro Gln Ile Ile Ser Phe Phe Leu
            180                 185                 190

Ala Leu Thr Ser Thr Ala Leu Leu Phe Leu Leu Phe Phe Leu Thr Leu
        195                 200                 205

Arg Phe Ser Val Val Lys Arg Gly Arg Lys Lys Leu Leu Tyr Ile Phe
    210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Glu Gly Gly Cys Glu Leu
                245                 250                 255


<210> SEQ ID NO 11
<211> LENGTH: 468
<212> TYPE: PRT
<213> ORGANISM: Homo sapiens

<400> SEQUENCE: 11

Met Ala Pro Pro Pro Ala Arg Val His Leu Gly Ala Phe Leu Ala Val
1               5                   10                  15

Thr Pro Asn Pro Gly Ser Ala Ala Ser Gly Thr Glu Ala Ala Ala Ala
```

```
            20                  25                  30

Thr Pro Ser Lys Val Trp Gly Ser Ser Ala Gly Arg Ile Glu Pro Arg
        35                  40                  45

Gly Gly Gly Arg Gly Ala Leu Pro Thr Ser Met Gly Gln His Gly Pro
    50                  55                  60

Ser Ala Arg Ala Arg Ala Gly Arg Ala Pro Gly Pro Arg Pro Ala Arg
65                  70                  75                  80

Glu Ala Ser Pro Arg Leu Arg Val His Lys Thr Phe Lys Phe Val Val
                85                  90                  95

Val Gly Val Leu Leu Gln Val Val Pro Ser Ser Ala Ala Thr Ile Lys
            100                 105                 110

Leu His Asp Gln Ser Ile Gly Thr Gln Gln Trp Glu His Ser Pro Leu
        115                 120                 125

Gly Glu Leu Cys Pro Pro Gly Ser His Arg Ser Glu His Pro Gly Ala
    130                 135                 140

Cys Asn Arg Cys Thr Glu Gly Val Gly Tyr Thr Asn Ala Ser Asn Asn
145                 150                 155                 160

Leu Phe Ala Cys Leu Pro Cys Thr Ala Cys Lys Ser Asp Glu Glu Glu
                165                 170                 175

Arg Ser Pro Cys Thr Thr Thr Arg Asn Thr Ala Cys Gln Cys Lys Pro
            180                 185                 190

Gly Thr Phe Arg Asn Asp Asn Ser Ala Glu Met Cys Arg Lys Cys Ser
        195                 200                 205

Arg Gly Cys Pro Arg Gly Met Val Lys Val Lys Asp Cys Thr Pro Trp
    210                 215                 220

Ser Asp Ile Glu Cys Val His Lys Glu Ser Gly Asn Gly His Asn Ile
225                 230                 235                 240

Trp Val Ile Leu Val Val Thr Leu Val Val Pro Leu Leu Leu Val Ala
                245                 250                 255

Val Leu Ile Val Cys Cys Cys Ile Gly Ser Gly Cys Gly Gly Asp Pro
            260                 265                 270

Lys Cys Met Asp Arg Val Cys Phe Trp Arg Leu Gly Leu Leu Arg Gly
        275                 280                 285

Pro Gly Ala Glu Asp Asn Ala His Asn Glu Ile Leu Ser Asn Ala Asp
    290                 295                 300

Ser Leu Ser Thr Phe Val Ser Glu Gln Gln Met Glu Ser Gln Glu Pro
305                 310                 315                 320

Ala Asp Leu Thr Gly Val Thr Val Gln Ser Pro Gly Glu Ala Gln Cys
                325                 330                 335

Leu Leu Gly Pro Ala Glu Ala Glu Gly Ser Gln Arg Arg Arg Leu Leu
            340                 345                 350

Val Pro Ala Asn Gly Ala Asp Pro Thr Glu Thr Leu Met Leu Phe Phe
        355                 360                 365

Asp Lys Phe Ala Asn Ile Val Pro Phe Asp Ser Trp Asp Gln Leu Met
    370                 375                 380

Arg Gln Leu Asp Leu Thr Lys Asn Glu Ile Asp Val Val Arg Ala Gly
385                 390                 395                 400

Thr Ala Gly Pro Gly Asp Ala Leu Tyr Ala Met Leu Met Lys Trp Val
                405                 410                 415

Asn Lys Thr Gly Arg Asn Ala Ser Ile His Thr Leu Leu Asp Ala Leu
            420                 425                 430

Glu Arg Met Glu Glu Arg His Ala Arg Glu Lys Ile Gln Asp Leu Leu
        435                 440                 445
```

```
Val Asp Ser Gly Lys Phe Ile Tyr Leu Glu Asp Gly Thr Gly Ser Ala
    450                 455                 460

Val Ser Leu Glu
465


<210> SEQ ID NO 12
<211> LENGTH: 440
<212> TYPE: PRT
<213> ORGANISM: Homo sapiens

<400> SEQUENCE: 12

Met Glu Gln Arg Gly Gln Asn Ala Pro Ala Ala Ser Gly Ala Arg Lys
1               5                   10                  15

Arg His Gly Pro Gly Pro Arg Glu Ala Arg Gly Ala Arg Pro Gly Pro
            20                  25                  30

Arg Val Pro Lys Thr Leu Val Leu Val Val Ala Ala Val Leu Leu Leu
        35                  40                  45

Val Ser Ala Glu Ser Ala Leu Ile Thr Gln Gln Asp Leu Ala Pro Gln
    50                  55                  60

Gln Arg Ala Ala Pro Gln Gln Lys Arg Ser Ser Pro Ser Glu Gly Leu
65                  70                  75                  80

Cys Pro Pro Gly His His Ile Ser Glu Asp Gly Arg Asp Cys Ile Ser
                85                  90                  95

Cys Lys Tyr Gly Gln Asp Tyr Ser Thr His Trp Asn Asp Leu Leu Phe
            100                 105                 110

Cys Leu Arg Cys Thr Arg Cys Asp Ser Gly Glu Val Glu Leu Ser Pro
        115                 120                 125

Cys Thr Thr Thr Arg Asn Thr Val Cys Gln Cys Glu Glu Gly Thr Phe
    130                 135                 140

Arg Glu Glu Asp Ser Pro Glu Met Cys Arg Lys Cys Arg Thr Gly Cys
145                 150                 155                 160

Pro Arg Gly Met Val Lys Val Gly Asp Cys Thr Pro Trp Ser Asp Ile
                165                 170                 175

Glu Cys Val His Lys Glu Ser Gly Thr Lys His Ser Gly Glu Val Pro
            180                 185                 190

Ala Val Glu Glu Thr Val Thr Ser Ser Pro Gly Thr Pro Ala Ser Pro
        195                 200                 205

Cys Ser Leu Ser Gly Ile Ile Ile Gly Val Thr Val Ala Ala Val Val
    210                 215                 220

Leu Ile Val Ala Val Phe Val Cys Lys Ser Leu Leu Trp Lys Lys Val
225                 230                 235                 240

Leu Pro Tyr Leu Lys Gly Ile Cys Ser Gly Gly Gly Gly Asp Pro Glu
                245                 250                 255

Arg Val Asp Arg Ser Ser Gln Arg Pro Gly Ala Glu Asp Asn Val Leu
            260                 265                 270

Asn Glu Ile Val Ser Ile Leu Gln Pro Thr Gln Val Pro Glu Gln Glu
        275                 280                 285

Met Glu Val Gln Glu Pro Ala Glu Pro Thr Gly Val Asn Met Leu Ser
    290                 295                 300

Pro Gly Glu Ser Glu His Leu Leu Glu Pro Ala Glu Ala Glu Arg Ser
305                 310                 315                 320

Gln Arg Arg Arg Leu Leu Val Pro Ala Asn Glu Gly Asp Pro Thr Glu
                325                 330                 335

Thr Leu Arg Gln Cys Phe Asp Asp Phe Ala Asp Leu Val Pro Phe Asp
```

```
            340                 345                 350

Ser Trp Glu Pro Leu Met Arg Lys Leu Gly Leu Met Asp Asn Glu Ile
        355                 360                 365

Lys Val Ala Lys Ala Glu Ala Ala Gly His Arg Asp Thr Leu Tyr Thr
    370                 375                 380

Met Leu Ile Lys Trp Val Asn Lys Thr Gly Arg Asp Ala Ser Val His
385                 390                 395                 400

Thr Leu Leu Asp Ala Leu Glu Thr Leu Gly Glu Arg Leu Ala Lys Gln
                405                 410                 415

Lys Ile Glu Asp His Leu Leu Ser Ser Gly Lys Phe Met Tyr Leu Glu
            420                 425                 430

Gly Asn Ala Asp Ser Ala Met Ser
        435                 440


<210> SEQ ID NO 13
<211> LENGTH: 259
<212> TYPE: PRT
<213> ORGANISM: Homo sapiens

<400> SEQUENCE: 13

Met Ala Arg Ile Pro Lys Thr Leu Lys Phe Val Val Val Ile Val Ala
1               5                   10                  15

Val Leu Leu Pro Val Leu Ala Tyr Ser Ala Thr Thr Ala Arg Gln Glu
            20                  25                  30

Glu Val Pro Gln Gln Thr Val Ala Pro Gln Gln Gln Arg His Ser Phe
        35                  40                  45

Lys Gly Glu Glu Cys Pro Ala Gly Ser His Arg Ser Glu His Thr Gly
    50                  55                  60

Ala Cys Asn Pro Cys Thr Glu Gly Val Asp Tyr Thr Asn Ala Ser Asn
65                  70                  75                  80

Asn Glu Pro Ser Cys Phe Pro Cys Thr Val Cys Lys Ser Asp Gln Lys
                85                  90                  95

His Lys Ser Ser Cys Thr Met Thr Arg Asp Thr Val Cys Gln Cys Lys
            100                 105                 110

Glu Gly Thr Phe Arg Asn Glu Asn Ser Pro Glu Met Cys Arg Lys Cys
        115                 120                 125

Ser Arg Cys Pro Ser Gly Glu Val Gln Val Ser Asn Cys Thr Ser Trp
    130                 135                 140

Asp Asp Ile Gln Cys Val Glu Glu Phe Gly Ala Asn Ala Thr Val Glu
145                 150                 155                 160

Thr Pro Ala Ala Glu Glu Thr Met Asn Thr Ser Pro Gly Thr Pro Ala
                165                 170                 175

Pro Ala Ala Glu Glu Thr Met Asn Thr Ser Pro Gly Thr Pro Ala Pro
            180                 185                 190

Ala Ala Glu Glu Thr Met Thr Thr Ser Pro Gly Thr Pro Ala Pro Ala
        195                 200                 205

Ala Glu Glu Thr Met Thr Thr Ser Pro Gly Thr Pro Ala Pro Ala Ala
    210                 215                 220

Glu Glu Thr Met Ile Thr Ser Pro Gly Thr Pro Ala Ser Ser His Tyr
225                 230                 235                 240

Leu Ser Cys Thr Ile Val Gly Ile Ile Val Leu Ile Val Leu Leu Ile
                245                 250                 255

Val Phe Val
```

```
<210> SEQ ID NO 14
<211> LENGTH: 386
<212> TYPE: PRT
<213> ORGANISM: Homo sapiens

<400> SEQUENCE: 14

Met Gly Leu Trp Gly Gln Ser Val Pro Thr Ala Ser Ser Ala Arg Ala
1               5                   10                  15

Gly Arg Tyr Pro Gly Ala Arg Thr Ala Ser Gly Thr Arg Pro Trp Leu
            20                  25                  30

Leu Asp Pro Lys Ile Leu Lys Phe Val Val Phe Ile Val Ala Val Leu
        35                  40                  45

Leu Pro Val Arg Val Asp Ser Ala Thr Ile Pro Arg Gln Asp Glu Val
    50                  55                  60

Pro Gln Gln Thr Val Ala Pro Gln Gln Gln Arg Arg Ser Leu Lys Glu
65                  70                  75                  80

Glu Glu Cys Pro Ala Gly Ser His Arg Ser Glu Tyr Thr Gly Ala Cys
                85                  90                  95

Asn Pro Cys Thr Glu Gly Val Asp Tyr Thr Ile Ala Ser Asn Asn Leu
            100                 105                 110

Pro Ser Cys Leu Leu Cys Thr Val Cys Lys Ser Gly Gln Thr Asn Lys
        115                 120                 125

Ser Ser Cys Thr Thr Thr Arg Asp Thr Val Cys Gln Cys Glu Lys Gly
    130                 135                 140

Ser Phe Gln Asp Lys Asn Ser Pro Glu Met Cys Arg Thr Cys Arg Thr
145                 150                 155                 160

Gly Cys Pro Arg Gly Met Val Lys Val Ser Asn Cys Thr Pro Arg Ser
                165                 170                 175

Asp Ile Lys Cys Lys Asn Glu Ser Ala Ala Ser Ser Thr Gly Lys Thr
            180                 185                 190

Pro Ala Ala Glu Glu Thr Val Thr Thr Ile Leu Gly Met Leu Ala Ser
        195                 200                 205

Pro Tyr His Tyr Leu Ile Ile Ile Val Val Leu Val Ile Ile Leu Ala
    210                 215                 220

Val Val Val Val Gly Phe Ser Cys Arg Lys Lys Phe Ile Ser Tyr Leu
225                 230                 235                 240

Lys Gly Ile Cys Ser Gly Gly Gly Gly Gly Pro Glu Arg Val His Arg
                245                 250                 255

Val Leu Phe Arg Arg Arg Ser Cys Pro Ser Arg Val Pro Gly Ala Glu
            260                 265                 270

Asp Asn Ala Arg Asn Glu Thr Leu Ser Asn Arg Tyr Leu Gln Pro Thr
        275                 280                 285

Gln Val Ser Glu Gln Glu Ile Gln Gly Gln Glu Leu Ala Glu Leu Thr
    290                 295                 300

Gly Val Thr Val Glu Ser Pro Glu Glu Pro Gln Arg Leu Leu Glu Gln
305                 310                 315                 320

Ala Glu Ala Glu Gly Cys Gln Arg Arg Arg Leu Leu Val Pro Val Asn
                325                 330                 335

Asp Ala Asp Ser Ala Asp Ile Ser Thr Leu Leu Asp Ala Ser Ala Thr
            340                 345                 350

Leu Glu Glu Gly His Ala Lys Glu Thr Ile Gln Asp Gln Leu Val Gly
        355                 360                 365

Ser Glu Lys Leu Phe Tyr Glu Glu Asp Glu Ala Gly Ser Ala Thr Ser
    370                 375                 380
```

```
Cys Leu
385


<210> SEQ ID NO 15
<211> LENGTH: 616
<212> TYPE: PRT
<213> ORGANISM: Homo sapiens

<400> SEQUENCE: 15

Met Ala Pro Arg Ala Arg Arg Arg Arg Pro Leu Phe Ala Leu Leu Leu
1               5                   10                  15

Leu Cys Ala Leu Leu Ala Arg Leu Gln Val Ala Leu Gln Ile Ala Pro
            20                  25                  30

Pro Cys Thr Ser Glu Lys His Tyr Glu His Leu Gly Arg Cys Cys Asn
        35                  40                  45

Lys Cys Glu Pro Gly Lys Tyr Met Ser Ser Lys Cys Thr Thr Thr Ser
    50                  55                  60

Asp Ser Val Cys Leu Pro Cys Gly Pro Asp Glu Tyr Leu Asp Ser Trp
65                  70                  75                  80

Asn Glu Glu Asp Lys Cys Leu Leu His Lys Val Cys Asp Thr Gly Lys
                85                  90                  95

Ala Leu Val Ala Val Val Ala Gly Asn Ser Thr Thr Pro Arg Arg Cys
            100                 105                 110

Ala Cys Thr Ala Gly Tyr His Trp Ser Gln Asp Cys Glu Cys Cys Arg
        115                 120                 125

Arg Asn Thr Glu Cys Ala Pro Gly Leu Gly Ala Gln His Pro Leu Gln
    130                 135                 140

Leu Asn Lys Asp Thr Val Cys Lys Pro Cys Leu Ala Gly Tyr Phe Ser
145                 150                 155                 160

Asp Ala Phe Ser Ser Thr Asp Lys Cys Arg Pro Trp Thr Asn Cys Thr
                165                 170                 175

Phe Leu Gly Lys Arg Val Glu His His Gly Thr Glu Lys Ser Asp Ala
            180                 185                 190

Val Cys Ser Ser Ser Leu Pro Ala Arg Lys Pro Pro Asn Glu Pro His
        195                 200                 205

Val Tyr Leu Pro Gly Leu Ile Ile Leu Leu Leu Phe Ala Ser Val Ala
    210                 215                 220

Leu Val Ala Ala Ile Ile Phe Gly Val Cys Tyr Arg Lys Lys Gly Lys
225                 230                 235                 240

Ala Leu Thr Ala Asn Leu Trp His Trp Ile Asn Glu Ala Cys Gly Arg
                245                 250                 255

Leu Ser Gly Asp Lys Glu Ser Ser Gly Asp Ser Cys Val Ser Thr His
            260                 265                 270

Thr Ala Asn Phe Gly Gln Gln Gly Ala Cys Glu Gly Val Leu Leu Leu
        275                 280                 285

Thr Leu Glu Glu Lys Thr Phe Pro Glu Asp Met Cys Tyr Pro Asp Gln
    290                 295                 300

Gly Gly Val Cys Gln Gly Thr Cys Val Gly Gly Gly Pro Tyr Ala Gln
305                 310                 315                 320

Gly Glu Asp Ala Arg Met Leu Ser Leu Val Ser Lys Thr Glu Ile Glu
                325                 330                 335

Glu Asp Ser Phe Arg Gln Met Pro Thr Glu Asp Glu Tyr Met Asp Arg
            340                 345                 350

Pro Ser Gln Pro Thr Asp Gln Leu Leu Phe Leu Thr Glu Pro Gly Ser
        355                 360                 365
```

```
Lys Ser Thr Pro Pro Phe Ser Glu Pro Leu Glu Val Gly Glu Asn Asp
    370                 375                 380

Ser Leu Ser Gln Cys Phe Thr Gly Thr Gln Ser Thr Val Gly Ser Glu
385                 390                 395                 400

Ser Cys Asn Cys Thr Glu Pro Leu Cys Arg Thr Asp Trp Thr Pro Met
                405                 410                 415

Ser Ser Glu Asn Tyr Leu Gln Lys Glu Val Asp Ser Gly His Cys Pro
            420                 425                 430

His Trp Ala Ala Ser Pro Ser Pro Asn Trp Ala Asp Val Cys Thr Gly
        435                 440                 445

Cys Arg Asn Pro Pro Gly Glu Asp Cys Glu Pro Leu Val Gly Ser Pro
    450                 455                 460

Lys Arg Gly Pro Leu Pro Gln Cys Ala Tyr Gly Met Gly Leu Pro Pro
465                 470                 475                 480

Glu Glu Glu Ala Ser Arg Thr Glu Ala Arg Asp Gln Pro Glu Asp Gly
                485                 490                 495

Ala Asp Gly Arg Leu Pro Ser Ser Ala Arg Ala Gly Ala Gly Ser Gly
            500                 505                 510

Ser Ser Pro Gly Gly Gln Ser Pro Ala Ser Gly Asn Val Thr Gly Asn
        515                 520                 525

Ser Asn Ser Thr Phe Ile Ser Ser Gly Gln Val Met Asn Phe Lys Gly
    530                 535                 540

Asp Ile Ile Val Val Tyr Val Ser Gln Thr Ser Gln Glu Gly Ala Ala
545                 550                 555                 560

Ala Ala Ala Glu Pro Met Gly Arg Pro Val Gln Glu Glu Thr Leu Ala
                565                 570                 575

Arg Arg Asp Ser Phe Ala Gly Asn Gly Pro Arg Phe Pro Asp Pro Cys
            580                 585                 590

Gly Gly Pro Glu Gly Leu Arg Glu Pro Glu Lys Ala Ser Arg Pro Val
        595                 600                 605

Gln Glu Gln Gly Gly Ala Lys Ala
    610                 615
```

<210> SEQ ID NO 16
<211> LENGTH: 401
<212> TYPE: PRT
<213> ORGANISM: Homo sapiens

<400> SEQUENCE: 16

```
Met Asn Asn Leu Leu Cys Cys Ala Leu Val Phe Leu Asp Ile Ser Ile
1               5                   10                  15

Lys Trp Thr Thr Gln Glu Thr Phe Pro Pro Lys Tyr Leu His Tyr Asp
            20                  25                  30

Glu Glu Thr Ser His Gln Leu Leu Cys Asp Lys Cys Pro Pro Gly Thr
        35                  40                  45

Tyr Leu Lys Gln His Cys Thr Ala Lys Trp Lys Thr Val Cys Ala Pro
    50                  55                  60

Cys Pro Asp His Tyr Tyr Thr Asp Ser Trp His Thr Ser Asp Glu Cys
65                  70                  75                  80

Leu Tyr Cys Ser Pro Val Cys Lys Glu Leu Gln Tyr Val Lys Gln Glu
                85                  90                  95

Cys Asn Arg Thr His Asn Arg Val Cys Glu Cys Lys Glu Gly Arg Tyr
            100                 105                 110

Leu Glu Ile Glu Phe Cys Leu Lys His Arg Ser Cys Pro Pro Gly Phe
```

```
        115                 120                 125

Gly Val Val Gln Ala Gly Thr Pro Glu Arg Asn Thr Val Cys Lys Arg
    130                 135                 140

Cys Pro Asp Gly Phe Phe Ser Asn Glu Thr Ser Ser Lys Ala Pro Cys
145                 150                 155                 160

Arg Lys His Thr Asn Cys Ser Val Phe Gly Leu Leu Leu Thr Gln Lys
                165                 170                 175

Gly Asn Ala Thr His Asp Asn Ile Cys Ser Gly Asn Ser Glu Ser Thr
            180                 185                 190

Gln Lys Cys Gly Ile Asp Val Thr Leu Cys Glu Glu Ala Phe Phe Arg
        195                 200                 205

Phe Ala Val Pro Thr Lys Phe Thr Pro Asn Trp Leu Ser Val Leu Val
    210                 215                 220

Asp Asn Leu Pro Gly Thr Lys Val Asn Ala Glu Ser Val Glu Arg Ile
225                 230                 235                 240

Lys Arg Gln His Ser Ser Gln Glu Gln Thr Phe Gln Leu Leu Lys Leu
                245                 250                 255

Trp Lys His Gln Asn Lys Asp Gln Asp Ile Val Lys Lys Ile Ile Gln
            260                 265                 270

Asp Ile Asp Leu Cys Glu Asn Ser Val Gln Arg His Ile Gly His Ala
        275                 280                 285

Asn Leu Thr Phe Glu Gln Leu Arg Ser Leu Met Glu Ser Leu Pro Gly
    290                 295                 300

Lys Lys Val Gly Ala Glu Asp Ile Glu Lys Thr Ile Lys Ala Cys Lys
305                 310                 315                 320

Pro Ser Asp Gln Ile Leu Lys Leu Leu Ser Leu Trp Arg Ile Lys Asn
                325                 330                 335

Gly Asp Gln Asp Thr Leu Lys Gly Leu Met His Ala Leu Lys His Ser
            340                 345                 350

Lys Thr Tyr His Phe Pro Lys Thr Val Thr Gln Ser Leu Lys Lys Thr
        355                 360                 365

Ile Arg Phe Leu His Ser Phe Thr Met Tyr Lys Leu Tyr Gln Lys Leu
    370                 375                 380

Phe Leu Glu Met Ile Gly Asn Gln Val Gln Ser Val Lys Ile Ser Cys
385                 390                 395                 400

Leu


<210> SEQ ID NO 17
<211> LENGTH: 129
<212> TYPE: PRT
<213> ORGANISM: Homo sapiens

<400> SEQUENCE: 17

Met Ala Arg Gly Ser Leu Arg Arg Leu Leu Arg Leu Leu Val Leu Gly
1               5                   10                  15

Leu Trp Leu Ala Leu Leu Arg Ser Val Ala Gly Glu Gln Ala Pro Gly
            20                  25                  30

Thr Ala Pro Cys Ser Arg Gly Ser Ser Trp Ser Ala Asp Leu Asp Lys
        35                  40                  45

Cys Met Asp Cys Ala Ser Cys Arg Ala Arg Pro His Ser Asp Phe Cys
    50                  55                  60

Leu Gly Cys Ala Ala Ala Pro Pro Ala Pro Phe Arg Leu Leu Trp Pro
65                  70                  75                  80

Ile Leu Gly Gly Ala Leu Ser Leu Thr Phe Val Leu Gly Leu Leu Ser
```

```
                85                  90                  95

Gly Phe Leu Val Trp Arg Arg Cys Arg Arg Arg Glu Lys Phe Thr Thr
            100                 105                 110

Pro Ile Glu Glu Thr Gly Gly Glu Gly Cys Pro Ala Val Ala Leu Ile
        115                 120                 125

Gln


<210> SEQ ID NO 18
<211> LENGTH: 293
<212> TYPE: PRT
<213> ORGANISM: Homo sapiens

<400> SEQUENCE: 18

Met Ser Gly Leu Gly Arg Ser Arg Arg Gly Gly Arg Ser Arg Val Asp
1               5                   10                  15

Gln Glu Glu Arg Phe Pro Gln Gly Leu Trp Thr Gly Val Ala Met Arg
            20                  25                  30

Ser Cys Pro Glu Glu Gln Tyr Trp Asp Pro Leu Leu Gly Thr Cys Met
        35                  40                  45

Ser Cys Lys Thr Ile Cys Asn His Gln Ser Gln Arg Thr Cys Ala Ala
    50                  55                  60

Phe Cys Arg Ser Leu Ser Cys Arg Lys Glu Gln Gly Lys Phe Tyr Asp
65                  70                  75                  80

His Leu Leu Arg Asp Cys Ile Ser Cys Ala Ser Ile Cys Gly Gln His
                85                  90                  95

Pro Lys Gln Cys Ala Tyr Phe Cys Glu Asn Lys Leu Arg Ser Pro Val
            100                 105                 110

Asn Leu Pro Pro Glu Leu Arg Arg Gln Arg Ser Gly Glu Val Glu Asn
        115                 120                 125

Asn Ser Asp Asn Ser Gly Arg Tyr Gln Gly Leu Glu His Arg Gly Ser
    130                 135                 140

Glu Ala Ser Pro Ala Leu Pro Gly Leu Lys Leu Ser Ala Asp Gln Val
145                 150                 155                 160

Ala Leu Val Tyr Ser Thr Leu Gly Leu Cys Leu Cys Ala Val Leu Cys
                165                 170                 175

Cys Phe Leu Val Ala Val Ala Cys Phe Leu Lys Lys Arg Gly Asp Pro
            180                 185                 190

Cys Ser Cys Gln Pro Arg Ser Arg Pro Arg Gln Ser Pro Ala Lys Ser
        195                 200                 205

Ser Gln Asp His Ala Met Glu Ala Gly Ser Pro Val Ser Thr Ser Pro
    210                 215                 220

Glu Pro Val Glu Thr Cys Ser Phe Cys Phe Pro Glu Cys Arg Ala Pro
225                 230                 235                 240

Thr Gln Glu Ser Ala Val Thr Pro Gly Thr Pro Asp Pro Thr Cys Ala
                245                 250                 255

Gly Arg Trp Gly Cys His Thr Arg Thr Thr Val Leu Gln Pro Cys Pro
            260                 265                 270

His Ile Pro Asp Ser Gly Leu Gly Ile Val Cys Val Pro Ala Gln Glu
        275                 280                 285

Gly Gly Pro Gly Ala
    290


<210> SEQ ID NO 19
<211> LENGTH: 184
<212> TYPE: PRT
```

<213> ORGANISM: Homo sapiens

<400> SEQUENCE: 19

```
Met Arg Arg Gly Pro Arg Ser Leu Arg Gly Arg Asp Ala Pro Ala Pro
1               5                   10                  15

Thr Pro Cys Val Pro Ala Glu Cys Phe Asp Leu Leu Val Arg His Cys
            20                  25                  30

Val Ala Cys Gly Leu Leu Arg Thr Pro Arg Pro Lys Pro Ala Gly Ala
        35                  40                  45

Ser Ser Pro Ala Pro Arg Thr Ala Leu Gln Pro Gln Glu Ser Val Gly
    50                  55                  60

Ala Gly Ala Gly Glu Ala Ala Leu Pro Leu Pro Gly Leu Leu Phe Gly
65                  70                  75                  80

Ala Pro Ala Leu Leu Gly Leu Ala Leu Val Leu Ala Leu Val Leu Val
                85                  90                  95

Gly Leu Val Ser Trp Arg Arg Arg Gln Arg Arg Leu Arg Gly Ala Ser
            100                 105                 110

Ser Ala Glu Ala Pro Asp Gly Asp Lys Asp Ala Pro Glu Pro Leu Asp
        115                 120                 125

Lys Val Ile Ile Leu Ser Pro Gly Ile Ser Asp Ala Thr Ala Pro Ala
    130                 135                 140

Trp Pro Pro Pro Gly Glu Asp Pro Gly Thr Thr Pro Pro Gly His Ser
145                 150                 155                 160

Val Pro Val Pro Ala Thr Glu Leu Gly Ser Thr Glu Leu Val Thr Thr
                165                 170                 175

Lys Thr Ala Gly Pro Glu Gln Gln
            180
```

<210> SEQ ID NO 20
<211> LENGTH: 283
<212> TYPE: PRT
<213> ORGANISM: Homo sapiens

<400> SEQUENCE: 20

```
Met Glu Pro Pro Gly Asp Trp Gly Pro Pro Pro Trp Arg Ser Thr Pro
1               5                   10                  15

Lys Thr Asp Val Leu Arg Leu Val Leu Tyr Leu Thr Phe Leu Gly Ala
            20                  25                  30

Pro Cys Tyr Ala Pro Ala Leu Pro Ser Cys Lys Glu Asp Glu Tyr Pro
        35                  40                  45

Val Gly Ser Glu Cys Cys Pro Lys Cys Ser Pro Gly Tyr Arg Val Lys
    50                  55                  60

Glu Ala Cys Gly Glu Leu Thr Gly Thr Val Cys Glu Pro Cys Pro Pro
65                  70                  75                  80

Gly Thr Tyr Ile Ala His Leu Asn Gly Leu Ser Lys Cys Leu Gln Cys
                85                  90                  95

Gln Met Cys Asp Pro Ala Met Gly Leu Arg Ala Ser Arg Asn Cys Ser
            100                 105                 110

Arg Thr Glu Asn Ala Val Cys Gly Cys Ser Pro Gly His Phe Cys Ile
        115                 120                 125

Val Gln Asp Gly Asp His Cys Ala Ala Cys Arg Ala Tyr Ala Thr Ser
    130                 135                 140

Ser Pro Gly Gln Arg Val Gln Lys Gly Gly Thr Glu Ser Gln Asp Thr
145                 150                 155                 160

Leu Cys Gln Asn Cys Pro Pro Gly Thr Phe Ser Pro Asn Gly Thr Leu
```

```
                165                 170                 175

Glu Glu Cys Gln His Gln Thr Lys Cys Ser Trp Leu Val Thr Lys Ala
            180                 185                 190

Gly Ala Gly Thr Ser Ser Ser His Trp Val Trp Trp Phe Leu Ser Gly
        195                 200                 205

Ser Leu Val Ile Val Ile Val Cys Ser Thr Val Gly Leu Ile Ile Cys
    210                 215                 220

Val Lys Arg Arg Lys Pro Arg Gly Asp Val Val Lys Val Ile Val Ser
225                 230                 235                 240

Val Gln Arg Lys Arg Gln Glu Ala Glu Gly Glu Ala Thr Val Ile Glu
                245                 250                 255

Ala Leu Gln Ala Pro Pro Asp Val Thr Thr Val Ala Val Glu Glu Thr
            260                 265                 270

Ile Pro Ser Phe Thr Gly Arg Ser Pro Asn His
        275                 280


<210> SEQ ID NO 21
<211> LENGTH: 427
<212> TYPE: PRT
<213> ORGANISM: Homo sapiens

<400> SEQUENCE: 21

Met Gly Ala Gly Ala Thr Gly Arg Ala Met Asp Gly Pro Arg Leu Leu
1               5                   10                  15

Leu Leu Leu Leu Leu Gly Val Ser Leu Gly Gly Ala Lys Glu Ala Cys
            20                  25                  30

Pro Thr Gly Leu Tyr Thr His Ser Gly Glu Cys Cys Lys Ala Cys Asn
        35                  40                  45

Leu Gly Glu Gly Val Ala Gln Pro Cys Gly Ala Asn Gln Thr Val Cys
    50                  55                  60

Glu Pro Cys Leu Asp Ser Val Thr Phe Ser Asp Val Val Ser Ala Thr
65                  70                  75                  80

Glu Pro Cys Lys Pro Cys Thr Glu Cys Val Gly Leu Gln Ser Met Ser
                85                  90                  95

Ala Pro Cys Val Glu Ala Asp Asp Ala Val Cys Arg Cys Ala Tyr Gly
            100                 105                 110

Tyr Tyr Gln Asp Glu Thr Thr Gly Arg Cys Glu Ala Cys Arg Val Cys
        115                 120                 125

Glu Ala Gly Ser Gly Leu Val Phe Ser Cys Gln Asp Lys Gln Asn Thr
    130                 135                 140

Val Cys Glu Glu Cys Pro Asp Gly Thr Tyr Ser Asp Glu Ala Asn His
145                 150                 155                 160

Val Asp Pro Cys Leu Pro Cys Thr Val Cys Glu Asp Thr Glu Arg Gln
                165                 170                 175

Leu Arg Glu Cys Thr Arg Trp Ala Asp Ala Glu Cys Glu Glu Ile Pro
            180                 185                 190

Gly Arg Trp Ile Thr Arg Ser Thr Pro Pro Glu Gly Ser Asp Ser Thr
        195                 200                 205

Ala Pro Ser Thr Gln Glu Pro Glu Ala Pro Pro Glu Gln Asp Leu Ile
    210                 215                 220

Ala Ser Thr Val Ala Gly Val Val Thr Thr Val Met Gly Ser Ser Gln
225                 230                 235                 240

Pro Val Val Thr Arg Gly Thr Thr Asp Asn Leu Ile Pro Val Tyr Cys
                245                 250                 255
```

```
Ser Ile Leu Ala Ala Val Val Val Gly Leu Val Ala Tyr Ile Ala Phe
            260                 265                 270

Lys Arg Trp Asn Ser Cys Lys Gln Asn Lys Gln Gly Ala Asn Ser Arg
        275                 280                 285

Pro Val Asn Gln Thr Pro Pro Pro Glu Gly Glu Lys Leu His Ser Asp
    290                 295                 300

Ser Gly Ile Ser Val Asp Ser Gln Ser Leu His Asp Gln Gln Pro His
305                 310                 315                 320

Thr Gln Thr Ala Ser Gly Gln Ala Leu Lys Gly Asp Gly Gly Leu Tyr
                325                 330                 335

Ser Ser Leu Pro Pro Ala Lys Arg Glu Glu Val Glu Lys Leu Leu Asn
            340                 345                 350

Gly Ser Ala Gly Asp Thr Trp Arg His Leu Ala Gly Glu Leu Gly Tyr
        355                 360                 365

Gln Pro Glu His Ile Asp Ser Phe Thr His Glu Ala Cys Pro Val Arg
    370                 375                 380

Ala Leu Leu Ala Ser Trp Ala Thr Gln Asp Ser Ala Thr Leu Asp Ala
385                 390                 395                 400

Leu Leu Ala Ala Leu Arg Arg Ile Gln Arg Ala Asp Leu Val Glu Ser
                405                 410                 415

Leu Cys Ser Glu Ser Thr Ala Thr Ser Pro Val
            420                 425


<210> SEQ ID NO 22
<211> LENGTH: 184
<212> TYPE: PRT
<213> ORGANISM: Homo sapiens

<400> SEQUENCE: 22

Met Leu Gln Met Ala Gly Gln Cys Ser Gln Asn Glu Tyr Phe Asp Ser
1               5                   10                  15

Leu Leu His Ala Cys Ile Pro Cys Gln Leu Arg Cys Ser Ser Asn Thr
            20                  25                  30

Pro Pro Leu Thr Cys Gln Arg Tyr Cys Asn Ala Ser Val Thr Asn Ser
        35                  40                  45

Val Lys Gly Thr Asn Ala Ile Leu Trp Thr Cys Leu Gly Leu Ser Leu
    50                  55                  60

Ile Ile Ser Leu Ala Val Phe Val Leu Met Phe Leu Leu Arg Lys Ile
65                  70                  75                  80

Asn Ser Glu Pro Leu Lys Asp Glu Phe Lys Asn Thr Gly Ser Gly Leu
                85                  90                  95

Leu Gly Met Ala Asn Ile Asp Leu Glu Lys Ser Arg Thr Gly Asp Glu
            100                 105                 110

Ile Ile Leu Pro Arg Gly Leu Glu Tyr Thr Val Glu Glu Cys Thr Cys
        115                 120                 125

Glu Asp Cys Ile Lys Ser Lys Pro Lys Val Asp Ser Asp His Cys Phe
    130                 135                 140

Pro Leu Pro Ala Met Glu Glu Gly Ala Thr Ile Leu Val Thr Thr Lys
145                 150                 155                 160

Thr Asn Asp Tyr Cys Lys Ser Leu Pro Ala Ala Leu Ser Ala Thr Glu
                165                 170                 175

Ile Glu Lys Ser Ile Ser Ala Arg
            180


<210> SEQ ID NO 23
```

<211> LENGTH: 241
<212> TYPE: PRT
<213> ORGANISM: Homo sapiens

<400> SEQUENCE: 23

```
Met Ala Gln His Gly Ala Met Gly Ala Phe Arg Ala Leu Cys Gly Leu
1               5                   10                  15

Ala Leu Leu Cys Ala Leu Ser Leu Gly Gln Arg Pro Thr Gly Gly Pro
            20                  25                  30

Gly Cys Gly Pro Gly Arg Leu Leu Leu Gly Thr Gly Thr Asp Ala Arg
        35                  40                  45

Cys Cys Arg Val His Thr Thr Arg Cys Cys Arg Asp Tyr Pro Gly Glu
    50                  55                  60

Glu Cys Cys Ser Glu Trp Asp Cys Met Cys Val Gln Pro Glu Phe His
65                  70                  75                  80

Cys Gly Asp Pro Cys Cys Thr Thr Cys Arg His His Pro Cys Pro Pro
                85                  90                  95

Gly Gln Gly Val Gln Ser Gln Gly Lys Phe Ser Phe Gly Phe Gln Cys
            100                 105                 110

Ile Asp Cys Ala Ser Gly Thr Phe Ser Gly Gly His Glu Gly His Cys
        115                 120                 125

Lys Pro Trp Thr Asp Cys Thr Gln Phe Gly Phe Leu Thr Val Phe Pro
    130                 135                 140

Gly Asn Lys Thr His Asn Ala Val Cys Val Pro Gly Ser Pro Pro Ala
145                 150                 155                 160

Glu Pro Leu Gly Trp Leu Thr Val Val Leu Leu Ala Val Ala Ala Cys
                165                 170                 175

Val Leu Leu Leu Thr Ser Ala Gln Leu Gly Leu His Ile Trp Gln Leu
            180                 185                 190

Arg Ser Gln Cys Met Trp Pro Arg Glu Thr Gln Leu Leu Leu Glu Val
        195                 200                 205

Pro Pro Ser Thr Glu Asp Ala Arg Ser Cys Gln Phe Pro Glu Glu Glu
    210                 215                 220

Arg Gly Glu Arg Ser Ala Glu Glu Lys Gly Arg Leu Gly Asp Leu Trp
225                 230                 235                 240

Val
```

<210> SEQ ID NO 24
<211> LENGTH: 423
<212> TYPE: PRT
<213> ORGANISM: Homo sapiens

<400> SEQUENCE: 24

```
Met Ala Leu Lys Val Leu Leu Glu Gln Glu Lys Thr Phe Phe Thr Leu
1               5                   10                  15

Leu Val Leu Leu Gly Tyr Leu Ser Cys Lys Val Thr Cys Glu Ser Gly
            20                  25                  30

Asp Cys Arg Gln Gln Glu Phe Arg Asp Arg Ser Gly Asn Cys Val Pro
        35                  40                  45

Cys Asn Gln Cys Gly Pro Gly Met Glu Leu Ser Lys Glu Cys Gly Phe
    50                  55                  60

Gly Tyr Gly Glu Asp Ala Gln Cys Val Thr Cys Arg Leu His Arg Phe
65                  70                  75                  80

Lys Glu Asp Trp Gly Phe Gln Lys Cys Lys Pro Cys Leu Asp Cys Ala
                85                  90                  95
```

```
Val Val Asn Arg Phe Gln Lys Ala Asn Cys Ser Ala Thr Ser Asp Ala
            100                 105                 110

Ile Cys Gly Asp Cys Leu Pro Gly Phe Tyr Arg Lys Thr Lys Leu Val
        115                 120                 125

Gly Phe Gln Asp Met Glu Cys Val Pro Cys Gly Asp Pro Pro Pro Pro
    130                 135                 140

Tyr Glu Pro His Cys Ala Ser Lys Val Asn Leu Val Lys Ile Ala Ser
145                 150                 155                 160

Thr Ala Ser Ser Pro Arg Asp Thr Ala Leu Ala Ala Val Ile Cys Ser
                165                 170                 175

Ala Leu Ala Thr Val Leu Leu Ala Leu Leu Ile Leu Cys Val Ile Tyr
            180                 185                 190

Cys Lys Arg Gln Phe Met Glu Lys Lys Pro Ser Trp Ser Leu Arg Ser
        195                 200                 205

Gln Asp Ile Gln Tyr Asn Gly Ser Glu Leu Ser Cys Phe Asp Arg Pro
    210                 215                 220

Gln Leu His Glu Tyr Ala His Arg Ala Cys Cys Gln Cys Arg Arg Asp
225                 230                 235                 240

Ser Val Gln Thr Cys Gly Pro Val Arg Leu Leu Pro Ser Met Cys Cys
                245                 250                 255

Glu Glu Ala Cys Ser Pro Asn Pro Ala Thr Leu Gly Cys Gly Val His
            260                 265                 270

Ser Ala Ala Ser Leu Gln Ala Arg Asn Ala Gly Pro Ala Gly Glu Met
        275                 280                 285

Val Pro Thr Phe Phe Gly Ser Leu Thr Gln Ser Ile Cys Gly Glu Phe
    290                 295                 300

Ser Asp Ala Trp Pro Leu Met Gln Asn Pro Met Gly Gly Asp Asn Ile
305                 310                 315                 320

Ser Phe Cys Asp Ser Tyr Pro Glu Leu Thr Gly Glu Asp Ile His Ser
                325                 330                 335

Leu Asn Pro Glu Leu Glu Ser Ser Thr Ser Leu Asp Ser Asn Ser Ser
            340                 345                 350

Gln Asp Leu Val Gly Gly Ala Val Pro Val Gln Ser His Ser Glu Asn
        355                 360                 365

Phe Thr Ala Ala Thr Asp Leu Ser Arg Tyr Asn Asn Thr Leu Val Glu
    370                 375                 380

Ser Ala Ser Thr Gln Asp Ala Leu Thr Met Arg Ser Gln Leu Asp Gln
385                 390                 395                 400

Glu Ser Gly Ala Val Ile His Pro Ala Thr Gln Thr Ser Leu Gln Val
                405                 410                 415

Arg Gln Arg Leu Gly Ser Leu
            420
```

<210> SEQ ID NO 25
<211> LENGTH: 655
<212> TYPE: PRT
<213> ORGANISM: Homo sapiens

<400> SEQUENCE: 25

```
Met Gly Thr Ser Pro Ser Ser Ser Thr Ala Leu Ala Ser Cys Ser Arg
1               5                   10                  15

Ile Ala Arg Arg Ala Thr Ala Thr Met Ile Ala Gly Ser Leu Leu Leu
            20                  25                  30

Leu Gly Phe Leu Ser Thr Thr Thr Ala Gln Pro Glu Gln Lys Ala Ser
        35                  40                  45
```

```
Asn Leu Ile Gly Thr Tyr Arg His Val Asp Arg Ala Thr Gly Gln Val
    50                  55                  60

Leu Thr Cys Asp Lys Cys Pro Ala Gly Thr Tyr Val Ser Glu His Cys
65                  70                  75                  80

Thr Asn Thr Ser Leu Arg Val Cys Ser Ser Cys Pro Val Gly Thr Phe
                85                  90                  95

Thr Arg His Glu Asn Gly Ile Glu Lys Cys His Asp Cys Ser Gln Pro
            100                 105                 110

Cys Pro Trp Pro Met Ile Glu Lys Leu Pro Cys Ala Ala Leu Thr Asp
        115                 120                 125

Arg Glu Cys Thr Cys Pro Pro Gly Met Phe Gln Ser Asn Ala Thr Cys
    130                 135                 140

Ala Pro His Thr Val Cys Pro Val Gly Trp Gly Val Arg Lys Lys Gly
145                 150                 155                 160

Thr Glu Thr Glu Asp Val Arg Cys Lys Gln Cys Ala Arg Gly Thr Phe
                165                 170                 175

Ser Asp Val Pro Ser Ser Val Met Lys Cys Lys Ala Tyr Thr Asp Cys
            180                 185                 190

Leu Ser Gln Asn Leu Val Val Ile Lys Pro Gly Thr Lys Glu Thr Asp
        195                 200                 205

Asn Val Cys Gly Thr Leu Pro Ser Phe Ser Ser Ser Thr Ser Pro Ser
    210                 215                 220

Pro Gly Thr Ala Ile Phe Pro Arg Pro Glu His Met Glu Thr His Glu
225                 230                 235                 240

Val Pro Ser Ser Thr Tyr Val Pro Lys Gly Met Asn Ser Thr Glu Ser
                245                 250                 255

Asn Ser Ser Ala Ser Val Arg Pro Lys Val Leu Ser Ser Ile Gln Glu
            260                 265                 270

Gly Thr Val Pro Asp Asn Thr Ser Ser Ala Arg Gly Lys Glu Asp Val
        275                 280                 285

Asn Lys Thr Leu Pro Asn Leu Gln Val Val Asn His Gln Gln Gly Pro
    290                 295                 300

His His Arg His Ile Leu Lys Leu Leu Pro Ser Met Glu Ala Thr Gly
305                 310                 315                 320

Gly Glu Lys Ser Ser Thr Pro Ile Lys Gly Pro Lys Arg Gly His Pro
                325                 330                 335

Arg Gln Asn Leu His Lys His Phe Asp Ile Asn Glu His Leu Pro Trp
            340                 345                 350

Met Ile Val Leu Phe Leu Leu Leu Val Leu Val Val Ile Val Val Cys
        355                 360                 365

Ser Ile Arg Lys Ser Ser Arg Thr Leu Lys Lys Gly Pro Arg Gln Asp
    370                 375                 380

Pro Ser Ala Ile Val Glu Lys Ala Gly Leu Lys Lys Ser Met Thr Pro
385                 390                 395                 400

Thr Gln Asn Arg Glu Lys Trp Ile Tyr Tyr Cys Asn Gly His Gly Ile
                405                 410                 415

Asp Ile Leu Lys Leu Val Ala Ala Gln Val Gly Ser Gln Trp Lys Asp
            420                 425                 430

Ile Tyr Gln Phe Leu Cys Asn Ala Ser Glu Arg Glu Val Ala Ala Phe
        435                 440                 445

Ser Asn Gly Tyr Thr Ala Asp His Glu Arg Ala Tyr Ala Ala Leu Gln
    450                 455                 460
```

```
His Trp Thr Ile Arg Gly Pro Glu Ala Ser Leu Ala Gln Leu Ile Ser
465                 470                 475                 480

Ala Leu Arg Gln His Arg Arg Asn Asp Val Val Glu Lys Ile Arg Gly
                485                 490                 495

Leu Met Glu Asp Thr Thr Gln Leu Glu Thr Asp Lys Leu Ala Leu Pro
            500                 505                 510

Met Ser Pro Ser Pro Leu Ser Pro Ser Pro Ile Pro Ser Pro Asn Ala
        515                 520                 525

Lys Leu Glu Asn Ser Ala Leu Leu Thr Val Glu Pro Ser Pro Gln Asp
    530                 535                 540

Lys Asn Lys Gly Phe Phe Val Asp Glu Ser Glu Pro Leu Leu Arg Cys
545                 550                 555                 560

Asp Ser Thr Ser Ser Gly Ser Ser Ala Leu Ser Arg Asn Gly Ser Phe
                565                 570                 575

Ile Thr Lys Glu Lys Lys Asp Thr Val Leu Arg Gln Val Arg Leu Asp
            580                 585                 590

Pro Cys Asp Leu Gln Pro Ile Phe Asp Asp Met Leu His Phe Leu Asn
        595                 600                 605

Pro Glu Glu Leu Arg Val Ile Glu Glu Ile Pro Gln Ala Glu Asp Lys
    610                 615                 620

Leu Asp Arg Leu Phe Glu Ile Ile Gly Val Lys Ser Gln Glu Ala Ser
625                 630                 635                 640

Gln Thr Leu Leu Asp Ser Val Tyr Ser His Leu Pro Asp Leu Leu
                645                 650                 655


<210> SEQ ID NO 26
<211> LENGTH: 417
<212> TYPE: PRT
<213> ORGANISM: Homo sapiens

<400> SEQUENCE: 26

Met Glu Gln Arg Pro Arg Gly Cys Ala Ala Val Ala Ala Ala Leu Leu
1               5                   10                  15

Leu Val Leu Leu Gly Ala Arg Ala Gln Gly Gly Thr Arg Ser Pro Arg
            20                  25                  30

Cys Asp Cys Ala Gly Asp Phe His Lys Lys Ile Gly Leu Phe Cys Cys
        35                  40                  45

Arg Gly Cys Pro Ala Gly His Tyr Leu Lys Ala Pro Cys Thr Glu Pro
    50                  55                  60

Cys Gly Asn Ser Thr Cys Leu Val Cys Pro Gln Asp Thr Phe Leu Ala
65                  70                  75                  80

Trp Glu Asn His His Asn Ser Glu Cys Ala Arg Cys Gln Ala Cys Asp
                85                  90                  95

Glu Gln Ala Ser Gln Val Ala Leu Glu Asn Cys Ser Ala Val Ala Asp
            100                 105                 110

Thr Arg Cys Gly Cys Lys Pro Gly Trp Phe Val Glu Cys Gln Val Ser
        115                 120                 125

Gln Cys Val Ser Ser Ser Pro Phe Tyr Cys Gln Pro Cys Leu Asp Cys
    130                 135                 140

Gly Ala Leu His Arg His Thr Arg Leu Leu Cys Ser Arg Arg Asp Thr
145                 150                 155                 160

Asp Cys Gly Thr Cys Leu Pro Gly Phe Tyr Glu His Gly Asp Gly Cys
                165                 170                 175

Val Ser Cys Pro Thr Ser Thr Leu Gly Ser Cys Pro Glu Arg Cys Ala
            180                 185                 190
```

```
Ala Val Cys Gly Trp Arg Gln Met Phe Trp Val Gln Val Leu Leu Ala
        195                 200                 205

Gly Leu Val Val Pro Leu Leu Leu Gly Ala Thr Leu Thr Tyr Thr Tyr
    210                 215                 220

Arg His Cys Trp Pro His Lys Pro Leu Val Thr Ala Asp Glu Ala Gly
225                 230                 235                 240

Met Glu Ala Leu Thr Pro Pro Pro Ala Thr His Leu Ser Pro Leu Asp
                245                 250                 255

Ser Ala His Thr Leu Leu Ala Pro Pro Asp Ser Ser Glu Lys Ile Cys
            260                 265                 270

Thr Val Gln Leu Val Gly Asn Ser Trp Thr Pro Gly Tyr Pro Glu Thr
        275                 280                 285

Gln Glu Ala Leu Cys Pro Gln Val Thr Trp Ser Trp Asp Gln Leu Pro
    290                 295                 300

Ser Arg Ala Leu Gly Pro Ala Ala Ala Pro Thr Leu Ser Pro Glu Ser
305                 310                 315                 320

Pro Ala Gly Ser Pro Ala Met Met Leu Gln Pro Gly Pro Gln Leu Tyr
                325                 330                 335

Asp Val Met Asp Ala Val Pro Ala Arg Arg Trp Lys Glu Phe Val Arg
            340                 345                 350

Thr Leu Gly Leu Arg Glu Ala Glu Ile Glu Ala Val Glu Val Glu Ile
        355                 360                 365

Gly Arg Phe Arg Asp Gln Gln Tyr Glu Met Leu Lys Arg Trp Arg Gln
    370                 375                 380

Gln Gln Pro Ala Gly Leu Gly Ala Val Tyr Ala Ala Leu Glu Arg Met
385                 390                 395                 400

Gly Leu Asp Gly Cys Val Glu Asp Leu Arg Ser Arg Leu Gln Arg Gly
                405                 410                 415

Pro


<210> SEQ ID NO 27
<211> LENGTH: 297
<212> TYPE: PRT
<213> ORGANISM: Homo sapiens

<400> SEQUENCE: 27

Met Asp Cys Gln Glu Asn Glu Tyr Trp Asp Gln Trp Gly Arg Cys Val
1               5                   10                  15

Thr Cys Gln Arg Cys Gly Pro Gly Gln Glu Leu Ser Lys Asp Cys Gly
            20                  25                  30

Tyr Gly Glu Gly Gly Asp Ala Tyr Cys Thr Ala Cys Pro Pro Arg Arg
        35                  40                  45

Tyr Lys Ser Ser Trp Gly His His Arg Cys Gln Ser Cys Ile Thr Cys
    50                  55                  60

Ala Val Ile Asn Arg Val Gln Lys Val Asn Cys Thr Ala Thr Ser Asn
65                  70                  75                  80

Ala Val Cys Gly Asp Cys Leu Pro Arg Phe Tyr Arg Lys Thr Arg Ile
                85                  90                  95

Gly Gly Leu Gln Asp Gln Glu Cys Ile Pro Cys Thr Lys Gln Thr Pro
            100                 105                 110

Thr Ser Glu Val Gln Cys Ala Phe Gln Leu Ser Leu Val Glu Ala Asp
        115                 120                 125

Thr Pro Thr Val Pro Pro Gln Glu Ala Thr Leu Val Ala Leu Val Ser
    130                 135                 140
```

```
Ser Leu Leu Val Val Phe Thr Leu Ala Phe Leu Gly Leu Phe Phe Leu
145                 150                 155                 160

Tyr Cys Lys Gln Phe Phe Asn Arg His Cys Gln Arg Gly Gly Leu Leu
                165                 170                 175

Gln Phe Glu Ala Asp Lys Thr Ala Lys Glu Glu Ser Leu Phe Pro Val
            180                 185                 190

Pro Pro Ser Lys Glu Thr Ser Ala Glu Ser Gln Val Ser Glu Asn Ile
        195                 200                 205

Phe Gln Thr Gln Pro Leu Asn Pro Ile Leu Glu Asp Asp Cys Ser Ser
    210                 215                 220

Thr Ser Gly Phe Pro Thr Gln Glu Ser Phe Thr Met Ala Ser Cys Thr
225                 230                 235                 240

Ser Glu Ser His Ser His Trp Val His Ser Pro Ile Glu Cys Thr Glu
                245                 250                 255

Leu Asp Leu Gln Lys Phe Ser Ser Ser Ala Ser Tyr Thr Gly Ala Glu
            260                 265                 270

Thr Leu Gly Gly Asn Thr Val Glu Ser Thr Gly Asp Arg Leu Glu Leu
        275                 280                 285

Asn Val Pro Phe Glu Val Pro Ser Pro
    290                 295


<210> SEQ ID NO 28
<211> LENGTH: 233
<212> TYPE: PRT
<213> ORGANISM: Homo sapiens

<400> SEQUENCE: 28

Met Ser Thr Glu Ser Met Ile Arg Asp Val Glu Leu Ala Glu Glu Ala
1               5                   10                  15

Leu Pro Lys Lys Thr Gly Gly Pro Gln Gly Ser Arg Arg Cys Leu Phe
            20                  25                  30

Leu Ser Leu Phe Ser Phe Leu Ile Val Ala Gly Ala Thr Thr Leu Phe
        35                  40                  45

Cys Leu Leu His Phe Gly Val Ile Gly Pro Gln Arg Glu Glu Phe Pro
    50                  55                  60

Arg Asp Leu Ser Leu Ile Ser Pro Leu Ala Gln Ala Val Arg Ser Ser
65                  70                  75                  80

Ser Arg Thr Pro Ser Asp Lys Pro Val Ala His Val Val Ala Asn Pro
                85                  90                  95

Gln Ala Glu Gly Gln Leu Gln Trp Leu Asn Arg Arg Ala Asn Ala Leu
            100                 105                 110

Leu Ala Asn Gly Val Glu Leu Arg Asp Asn Gln Leu Val Val Pro Ser
        115                 120                 125

Glu Gly Leu Tyr Leu Ile Tyr Ser Gln Val Leu Phe Lys Gly Gln Gly
    130                 135                 140

Cys Pro Ser Thr His Val Leu Leu Thr His Thr Ile Ser Arg Ile Ala
145                 150                 155                 160

Val Ser Tyr Gln Thr Lys Val Asn Leu Leu Ser Ala Ile Lys Ser Pro
                165                 170                 175

Cys Gln Arg Glu Thr Pro Glu Gly Ala Glu Ala Lys Pro Trp Tyr Glu
            180                 185                 190

Pro Ile Tyr Leu Gly Gly Val Phe Gln Leu Glu Lys Gly Asp Arg Leu
        195                 200                 205

Ser Ala Glu Ile Asn Arg Pro Asp Tyr Leu Asp Phe Ala Glu Ser Gly
```

```
    210                 215                 220

Gln Val Tyr Phe Gly Ile Ile Ala Leu
225                 230


<210> SEQ ID NO 29
<211> LENGTH: 244
<212> TYPE: PRT
<213> ORGANISM: Homo sapiens

<400> SEQUENCE: 29

Met Gly Ala Leu Gly Leu Glu Gly Arg Gly Gly Arg Leu Gln Gly Arg
1               5                   10                  15

Gly Ser Leu Leu Leu Ala Val Ala Gly Ala Thr Ser Leu Val Thr Leu
            20                  25                  30

Leu Leu Ala Val Pro Ile Thr Val Leu Ala Val Leu Ala Leu Val Pro
        35                  40                  45

Gln Asp Gln Gly Gly Leu Val Thr Glu Thr Ala Asp Pro Gly Ala Gln
    50                  55                  60

Ala Gln Gln Gly Leu Gly Phe Gln Lys Leu Pro Glu Glu Glu Pro Glu
65                  70                  75                  80

Thr Asp Leu Ser Pro Gly Leu Pro Ala Ala His Leu Ile Gly Ala Pro
                85                  90                  95

Leu Lys Gly Gln Gly Leu Gly Trp Glu Thr Thr Lys Glu Gln Ala Phe
            100                 105                 110

Leu Thr Ser Gly Thr Gln Phe Ser Asp Ala Glu Gly Leu Ala Leu Pro
        115                 120                 125

Gln Asp Gly Leu Tyr Tyr Leu Tyr Cys Leu Val Gly Tyr Arg Gly Arg
    130                 135                 140

Ala Pro Pro Gly Gly Gly Asp Pro Gln Gly Arg Ser Val Thr Leu Arg
145                 150                 155                 160

Ser Ser Leu Tyr Arg Ala Gly Gly Ala Tyr Gly Pro Gly Thr Pro Glu
                165                 170                 175

Leu Leu Leu Glu Gly Ala Glu Thr Val Thr Pro Val Leu Asp Pro Ala
            180                 185                 190

Arg Arg Gln Gly Tyr Gly Pro Leu Trp Tyr Thr Ser Val Gly Phe Gly
        195                 200                 205

Gly Leu Val Gln Leu Arg Arg Gly Glu Arg Val Tyr Val Asn Ile Ser
    210                 215                 220

His Pro Asp Met Val Asp Phe Ala Arg Gly Lys Thr Phe Phe Gly Ala
225                 230                 235                 240

Val Met Val Gly


<210> SEQ ID NO 30
<211> LENGTH: 183
<212> TYPE: PRT
<213> ORGANISM: Homo sapiens

<400> SEQUENCE: 30

Met Glu Arg Val Gln Pro Leu Glu Glu Asn Val Gly Asn Ala Ala Arg
1               5                   10                  15

Pro Arg Phe Glu Arg Asn Lys Leu Leu Leu Val Ala Ser Val Ile Gln
            20                  25                  30

Gly Leu Gly Leu Leu Leu Cys Phe Thr Tyr Ile Cys Leu His Phe Ser
        35                  40                  45

Ala Leu Gln Val Ser His Arg Tyr Pro Arg Ile Gln Ser Ile Lys Val
    50                  55                  60
```

```
Gln Phe Thr Glu Tyr Lys Lys Glu Lys Gly Phe Ile Leu Thr Ser Gln
65                  70                  75                  80

Lys Glu Asp Glu Ile Met Lys Val Gln Asn Asn Ser Val Ile Ile Asn
                85                  90                  95

Cys Asp Gly Phe Tyr Leu Ile Ser Leu Lys Gly Tyr Phe Ser Gln Glu
            100                 105                 110

Val Asn Ile Ser Leu His Tyr Gln Lys Asp Glu Glu Pro Leu Phe Gln
        115                 120                 125

Leu Lys Lys Val Arg Ser Val Asn Ser Leu Met Val Ala Ser Leu Thr
    130                 135                 140

Tyr Lys Asp Lys Val Tyr Leu Asn Val Thr Thr Asp Asn Thr Ser Leu
145                 150                 155                 160

Asp Asp Phe His Val Asn Gly Gly Glu Leu Ile Leu Ile His Gln Asn
                165                 170                 175

Pro Gly Glu Phe Cys Val Leu
            180


<210> SEQ ID NO 31
<211> LENGTH: 240
<212> TYPE: PRT
<213> ORGANISM: Homo sapiens

<400> SEQUENCE: 31

Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
            20                  25                  30

Ile Thr Gln Met Ile Gly Ser Ala Leu Phe Ala Val Tyr Leu His Arg
        35                  40                  45

Arg Leu Asp Lys Ile Glu Asp Glu Arg Asn Leu His Glu Asp Phe Val
    50                  55                  60

Phe Met Lys Thr Ile Gln Arg Cys Asn Thr Gly Glu Arg Ser Leu Ser
65                  70                  75                  80

Leu Leu Asn Cys Glu Glu Ile Lys Ser Gln Phe Glu Gly Phe Val Lys
                85                  90                  95

Asp Ile Met Leu Asn Lys Glu Glu Thr Lys Lys Glu Asn Ser Phe Glu
            100                 105                 110

Met Gln Lys Val Leu Gln Trp Ala Glu Lys Gly Tyr Tyr Thr Met Ser
        115                 120                 125

Asn Asn Leu Val Thr Leu Glu Asn Gly Lys Gln Leu Thr Val Lys Arg
    130                 135                 140

Gln Gly Leu Tyr Tyr Ile Tyr Ala Gln Val Thr Phe Cys Ser Asn Arg
145                 150                 155                 160

Glu Ala Ser Ser Gln Ala Pro Phe Ile Ala Ser Leu Cys Leu Lys Ser
                165                 170                 175

Pro Gly Arg Phe Glu Arg Ile Leu Leu Arg Ala Ala Asn Thr His Ser
            180                 185                 190

Ser Ala Lys Pro Cys Gly Gln Gln Ser Ile His Leu Gly Gly Val Phe
        195                 200                 205

Glu Leu Gln Pro Gly Ala Ser Val Phe Val Asn Val Thr Asp Pro Ser
    210                 215                 220

Gln Val Ser His Gly Thr Gly Phe Thr Ser Phe Gly Leu Leu Lys Leu
225                 230                 235                 240
```

<210> SEQ ID NO 32
<211> LENGTH: 281
<212> TYPE: PRT
<213> ORGANISM: Homo sapiens

<400> SEQUENCE: 32

```
Met Gln Gln Pro Phe Asn Tyr Pro Tyr Pro Gln Ile Tyr Trp Val Asp
1               5                   10                  15

Ser Ser Ala Ser Ser Pro Trp Ala Pro Pro Gly Thr Val Leu Pro Cys
            20                  25                  30

Pro Thr Ser Val Pro Arg Arg Pro Gly Gln Arg Arg Pro Pro Pro Pro
        35                  40                  45

Pro Pro Pro Pro Pro Leu Pro Pro Pro Pro Pro Pro Pro Pro Leu Pro
    50                  55                  60

Pro Leu Pro Leu Pro Pro Leu Lys Lys Arg Gly Asn His Ser Thr Gly
65                  70                  75                  80

Leu Cys Leu Leu Val Met Phe Phe Met Val Leu Val Ala Leu Val Gly
                85                  90                  95

Leu Gly Leu Gly Met Phe Gln Leu Phe His Leu Gln Lys Glu Leu Ala
            100                 105                 110

Glu Leu Arg Glu Ser Thr Ser Gln Met His Thr Ala Ser Ser Leu Glu
        115                 120                 125

Lys Gln Ile Gly His Pro Ser Pro Pro Pro Glu Lys Lys Glu Leu Arg
    130                 135                 140

Lys Val Ala His Leu Thr Gly Lys Ser Asn Ser Arg Ser Met Pro Leu
145                 150                 155                 160

Glu Trp Glu Asp Thr Tyr Gly Ile Val Leu Leu Ser Gly Val Lys Tyr
                165                 170                 175

Lys Lys Gly Gly Leu Val Ile Asn Glu Thr Gly Leu Tyr Phe Val Tyr
            180                 185                 190

Ser Lys Val Tyr Phe Arg Gly Gln Ser Cys Asn Asn Leu Pro Leu Ser
        195                 200                 205

His Lys Val Tyr Met Arg Asn Ser Lys Tyr Pro Gln Asp Leu Val Met
    210                 215                 220

Met Glu Gly Lys Met Met Ser Tyr Cys Thr Thr Gly Gln Met Trp Ala
225                 230                 235                 240

Arg Ser Ser Tyr Leu Gly Ala Val Phe Asn Leu Thr Ser Ala Asp His
                245                 250                 255

Leu Tyr Val Asn Val Ser Glu Leu Ser Leu Val Asn Phe Glu Glu Ser
            260                 265                 270

Gln Thr Phe Phe Gly Leu Tyr Lys Leu
        275                 280
```

<210> SEQ ID NO 33
<211> LENGTH: 240
<212> TYPE: PRT
<213> ORGANISM: Homo sapiens

<400> SEQUENCE: 33

```
Met Glu Glu Ser Val Val Arg Pro Ser Val Phe Val Val Asp Gly Gln
1               5                   10                  15

Thr Asp Ile Pro Phe Thr Arg Leu Gly Arg Ser His Arg Arg Gln Ser
            20                  25                  30

Cys Ser Val Ala Arg Val Gly Leu Gly Leu Leu Leu Leu Leu Met Gly
        35                  40                  45

Ala Gly Leu Ala Val Gln Gly Trp Phe Leu Leu Gln Leu His Trp Arg
```

```
    50                  55                  60

Leu Gly Glu Met Val Thr Arg Leu Pro Asp Gly Pro Ala Gly Ser Trp
65                  70                  75                  80

Glu Gln Leu Ile Gln Glu Arg Arg Ser His Glu Val Asn Pro Ala Ala
                85                  90                  95

His Leu Thr Gly Ala Asn Ser Ser Leu Thr Gly Ser Gly Gly Pro Leu
            100                 105                 110

Leu Trp Glu Thr Gln Leu Gly Leu Ala Phe Leu Arg Gly Leu Ser Tyr
        115                 120                 125

His Asp Gly Ala Leu Val Val Thr Lys Ala Gly Tyr Tyr Tyr Ile Tyr
    130                 135                 140

Ser Lys Val Gln Leu Gly Gly Val Gly Cys Pro Leu Gly Leu Ala Ser
145                 150                 155                 160

Thr Ile Thr His Gly Leu Tyr Lys Arg Thr Pro Arg Tyr Pro Glu Glu
                165                 170                 175

Leu Glu Leu Leu Val Ser Gln Gln Ser Pro Cys Gly Arg Ala Thr Ser
            180                 185                 190

Ser Ser Arg Val Trp Trp Asp Ser Ser Phe Leu Gly Gly Val Val His
        195                 200                 205

Leu Glu Ala Gly Glu Lys Val Val Val Arg Val Leu Asp Glu Arg Leu
    210                 215                 220

Val Arg Leu Arg Asp Gly Thr Arg Ser Tyr Phe Gly Ala Phe Met Val
225                 230                 235                 240


<210> SEQ ID NO 34
<211> LENGTH: 251
<212> TYPE: PRT
<213> ORGANISM: Homo sapiens

<400> SEQUENCE: 34

Met Ala Glu Asp Leu Gly Leu Ser Phe Gly Glu Thr Ala Ser Val Glu
1               5                   10                  15

Met Leu Pro Glu His Gly Ser Cys Arg Pro Lys Ala Arg Ser Ser Ser
            20                  25                  30

Ala Arg Trp Ala Leu Thr Cys Cys Leu Val Leu Leu Pro Phe Leu Ala
        35                  40                  45

Gly Leu Thr Thr Tyr Leu Leu Val Ser Gln Leu Arg Ala Gln Gly Glu
    50                  55                  60

Ala Cys Val Gln Phe Gln Ala Leu Lys Gly Gln Glu Phe Ala Pro Ser
65                  70                  75                  80

His Gln Gln Val Tyr Ala Pro Leu Arg Ala Asp Gly Asp Lys Pro Arg
                85                  90                  95

Ala His Leu Thr Val Val Arg Gln Thr Pro Thr Gln His Phe Lys Asn
            100                 105                 110

Gln Phe Pro Ala Leu His Trp Glu His Glu Leu Gly Leu Ala Phe Thr
        115                 120                 125

Lys Asn Arg Met Asn Tyr Thr Asn Lys Phe Leu Leu Ile Pro Glu Ser
    130                 135                 140

Gly Asp Tyr Phe Ile Tyr Ser Gln Val Thr Phe Arg Gly Met Thr Ser
145                 150                 155                 160

Glu Cys Ser Glu Ile Arg Gln Ala Gly Arg Pro Asn Lys Pro Asp Ser
                165                 170                 175

Ile Thr Val Val Ile Thr Lys Val Thr Asp Ser Tyr Pro Glu Pro Thr
            180                 185                 190
```

```
Gln Leu Leu Met Gly Thr Lys Ser Val Cys Glu Val Gly Ser Asn Trp
        195                 200                 205

Phe Gln Pro Ile Tyr Leu Gly Ala Met Phe Ser Leu Gln Glu Gly Asp
    210                 215                 220

Lys Leu Met Val Asn Val Ser Asp Ile Ser Leu Val Asp Tyr Thr Lys
225                 230                 235                 240

Glu Asp Lys Thr Phe Phe Gly Ala Phe Leu Leu
                245                 250


<210> SEQ ID NO 35
<211> LENGTH: 193
<212> TYPE: PRT
<213> ORGANISM: Homo sapiens

<400> SEQUENCE: 35

Met Pro Glu Glu Gly Ser Gly Cys Ser Val Arg Arg Arg Pro Tyr Gly
1               5                   10                  15

Cys Val Leu Arg Ala Ala Leu Val Pro Leu Val Ala Gly Leu Val Ile
            20                  25                  30

Cys Leu Val Val Cys Ile Gln Arg Phe Ala Gln Ala Gln Gln Gln Leu
        35                  40                  45

Pro Leu Glu Ser Leu Gly Trp Asp Val Ala Glu Leu Gln Leu Asn His
    50                  55                  60

Thr Gly Pro Gln Gln Asp Pro Arg Leu Tyr Trp Gln Gly Gly Pro Ala
65                  70                  75                  80

Leu Gly Arg Ser Phe Leu His Gly Pro Glu Leu Asp Lys Gly Gln Leu
                85                  90                  95

Arg Ile His Arg Asp Gly Ile Tyr Met Val His Ile Gln Val Thr Leu
            100                 105                 110

Ala Ile Cys Ser Ser Thr Thr Ala Ser Arg His His Pro Thr Thr Leu
        115                 120                 125

Ala Val Gly Ile Cys Ser Pro Ala Ser Arg Ser Ile Ser Leu Leu Arg
    130                 135                 140

Leu Ser Phe His Gln Gly Cys Thr Ile Ala Ser Gln Arg Leu Thr Pro
145                 150                 155                 160

Leu Ala Arg Gly Asp Thr Leu Cys Thr Asn Leu Thr Gly Thr Leu Leu
                165                 170                 175

Pro Ser Arg Asn Thr Asp Glu Thr Phe Phe Gly Val Gln Trp Val Arg
            180                 185                 190

Pro


<210> SEQ ID NO 36
<211> LENGTH: 175
<212> TYPE: PRT
<213> ORGANISM: Homo sapiens

<400> SEQUENCE: 36

Met Pro Lys Arg Ser Cys Pro Phe Ala Asp Val Ala Pro Leu Gln Leu
1               5                   10                  15

Lys Val Arg Val Ser Gln Arg Glu Leu Ser Arg Gly Val Cys Ala Glu
            20                  25                  30

Arg Tyr Ser Gln Glu Val Phe Glu Lys Thr Lys Arg Leu Leu Phe Leu
        35                  40                  45

Gly Ala Gln Ala Tyr Leu Asp His Val Trp Asp Glu Gly Cys Ala Val
    50                  55                  60

Val His Leu Pro Glu Ser Pro Lys Pro Gly Pro Thr Gly Ala Pro Arg
```

```
65                  70                  75                  80

Ala Ala Arg Gly Gln Met Leu Ile Gly Pro Asp Gly Arg Leu Ile Arg
                85                  90                  95

Ser Leu Gly Gln Ala Ser Glu Ala Asp Pro Ser Gly Val Ala Ser Ile
            100                 105                 110

Ala Cys Ser Ser Cys Val Arg Ala Val Asp Gly Lys Ala Val Cys Gly
        115                 120                 125

Gln Cys Glu Arg Ala Leu Cys Gly Gln Cys Val Arg Thr Cys Trp Gly
    130                 135                 140

Cys Gly Ser Val Ala Cys Thr Leu Cys Gly Leu Val Asp Cys Ser Asp
145                 150                 155                 160

Met Tyr Glu Lys Val Leu Cys Thr Ser Cys Ala Met Phe Glu Thr
                165                 170                 175


<210> SEQ ID NO 37
<211> LENGTH: 234
<212> TYPE: PRT
<213> ORGANISM: Homo sapiens

<400> SEQUENCE: 37

Met Asp Pro Gly Leu Gln Gln Ala Leu Asn Gly Met Ala Pro Pro Gly
1               5                   10                  15

Asp Thr Ala Met His Val Pro Ala Gly Ser Val Ala Ser His Leu Gly
            20                  25                  30

Thr Thr Ser Arg Ser Tyr Phe Tyr Leu Thr Thr Ala Thr Leu Ala Leu
        35                  40                  45

Cys Leu Val Phe Thr Val Ala Thr Ile Met Val Leu Val Val Gln Arg
    50                  55                  60

Thr Asp Ser Ile Pro Asn Ser Pro Asp Asn Val Pro Leu Lys Gly Gly
65                  70                  75                  80

Asn Cys Ser Glu Asp Leu Leu Cys Ile Leu Lys Arg Ala Pro Phe Lys
                85                  90                  95

Lys Ser Trp Ala Tyr Leu Gln Val Ala Lys His Leu Asn Lys Thr Lys
            100                 105                 110

Leu Ser Trp Asn Lys Asp Gly Ile Leu His Gly Val Arg Tyr Gln Asp
        115                 120                 125

Gly Asn Leu Val Ile Gln Phe Pro Gly Leu Tyr Phe Ile Ile Cys Gln
    130                 135                 140

Leu Gln Phe Leu Val Gln Cys Pro Asn Asn Ser Val Asp Leu Lys Leu
145                 150                 155                 160

Glu Leu Leu Ile Asn Lys His Ile Lys Lys Gln Ala Leu Val Thr Val
                165                 170                 175

Cys Glu Ser Gly Met Gln Thr Lys His Val Tyr Gln Asn Leu Ser Gln
            180                 185                 190

Phe Leu Leu Asp Tyr Leu Gln Val Asn Thr Thr Ile Ser Val Asn Val
        195                 200                 205

Asp Thr Phe Gln Tyr Ile Asp Thr Ser Thr Phe Pro Leu Glu Asn Val
    210                 215                 220

Leu Ser Ile Phe Leu Tyr Ser Asn Ser Asp
225                 230


<210> SEQ ID NO 38
<211> LENGTH: 254
<212> TYPE: PRT
<213> ORGANISM: Homo sapiens
```

<400> SEQUENCE: 38

```
Met Glu Tyr Ala Ser Asp Ala Ser Leu Asp Pro Glu Ala Pro Trp Pro
1               5                   10                  15

Pro Ala Pro Arg Ala Arg Ala Cys Arg Val Leu Pro Trp Ala Leu Val
            20                  25                  30

Ala Gly Leu Leu Leu Leu Leu Leu Leu Ala Ala Ala Cys Ala Val Phe
        35                  40                  45

Leu Ala Cys Pro Trp Ala Val Ser Gly Ala Arg Ala Ser Pro Gly Ser
    50                  55                  60

Ala Ala Ser Pro Arg Leu Arg Glu Gly Pro Glu Leu Ser Pro Asp Asp
65                  70                  75                  80

Pro Ala Gly Leu Leu Asp Leu Arg Gln Gly Met Phe Ala Gln Leu Val
                85                  90                  95

Ala Gln Asn Val Leu Leu Ile Asp Gly Pro Leu Ser Trp Tyr Ser Asp
            100                 105                 110

Pro Gly Leu Ala Gly Val Ser Leu Thr Gly Gly Leu Ser Tyr Lys Glu
        115                 120                 125

Asp Thr Lys Glu Leu Val Val Ala Lys Ala Gly Val Tyr Tyr Val Phe
    130                 135                 140

Phe Gln Leu Glu Leu Arg Arg Val Val Ala Gly Glu Gly Ser Gly Ser
145                 150                 155                 160

Val Ser Leu Ala Leu His Leu Gln Pro Leu Arg Ser Ala Ala Gly Ala
                165                 170                 175

Ala Ala Leu Ala Leu Thr Val Asp Leu Pro Pro Ala Ser Ser Glu Ala
            180                 185                 190

Arg Asn Ser Ala Phe Gly Phe Gln Gly Arg Leu Leu His Leu Ser Ala
        195                 200                 205

Gly Gln Arg Leu Gly Val His Leu His Thr Glu Ala Arg Ala Arg His
    210                 215                 220

Ala Trp Gln Leu Thr Gln Gly Ala Thr Val Leu Gly Leu Phe Arg Val
225                 230                 235                 240

Thr Pro Glu Ile Pro Ala Gly Leu Pro Ser Pro Arg Ser Glu
                245                 250
```

<210> SEQ ID NO 39
<211> LENGTH: 281
<212> TYPE: PRT
<213> ORGANISM: Homo sapiens

<400> SEQUENCE: 39

```
Met Ala Met Met Glu Val Gln Gly Gly Pro Ser Leu Gly Gln Thr Cys
1               5                   10                  15

Val Leu Ile Val Ile Phe Thr Val Leu Leu Gln Ser Leu Cys Val Ala
            20                  25                  30

Val Thr Tyr Val Tyr Phe Thr Asn Glu Leu Lys Gln Met Gln Asp Lys
        35                  40                  45

Tyr Ser Lys Ser Gly Ile Ala Cys Phe Leu Lys Glu Asp Asp Ser Tyr
    50                  55                  60

Trp Asp Pro Asn Asp Glu Glu Ser Met Asn Ser Pro Cys Trp Gln Val
65                  70                  75                  80

Lys Trp Gln Leu Arg Gln Leu Val Arg Lys Met Ile Leu Arg Thr Ser
                85                  90                  95

Glu Glu Thr Ile Ser Thr Val Gln Glu Lys Gln Gln Asn Ile Ser Pro
            100                 105                 110
```

```
Leu Val Arg Glu Arg Gly Pro Gln Arg Val Ala Ala His Ile Thr Gly
        115                 120                 125

Thr Arg Gly Arg Ser Asn Thr Leu Ser Ser Pro Asn Ser Lys Asn Glu
    130                 135                 140

Lys Ala Leu Gly Arg Lys Ile Asn Ser Trp Glu Ser Ser Arg Ser Gly
145                 150                 155                 160

His Ser Phe Leu Ser Asn Leu His Leu Arg Asn Gly Glu Leu Val Ile
                165                 170                 175

His Glu Lys Gly Phe Tyr Tyr Ile Tyr Ser Gln Thr Tyr Phe Arg Phe
            180                 185                 190

Gln Glu Glu Ile Lys Glu Asn Thr Lys Asn Asp Lys Gln Met Val Gln
        195                 200                 205

Tyr Ile Tyr Lys Tyr Thr Ser Tyr Pro Asp Pro Ile Leu Leu Met Lys
    210                 215                 220

Ser Ala Arg Asn Ser Cys Trp Ser Lys Asp Ala Glu Tyr Gly Leu Tyr
225                 230                 235                 240

Ser Ile Tyr Gln Gly Gly Ile Phe Glu Leu Lys Glu Asn Asp Arg Ile
                245                 250                 255

Phe Val Ser Val Thr Asn Glu His Leu Ile Asp Met Asp His Glu Ala
            260                 265                 270

Ser Phe Phe Gly Ala Phe Leu Val Gly
        275                 280


<210> SEQ ID NO 40
<211> LENGTH: 317
<212> TYPE: PRT
<213> ORGANISM: Homo sapiens

<400> SEQUENCE: 40

Met Arg Arg Ala Ser Arg Asp Tyr Thr Lys Tyr Leu Arg Gly Ser Glu
1               5                   10                  15

Glu Met Gly Gly Gly Pro Gly Ala Pro His Glu Gly Pro Leu His Ala
            20                  25                  30

Pro Pro Pro Pro Ala Pro His Gln Pro Pro Ala Ala Ser Arg Ser Met
        35                  40                  45

Phe Val Ala Leu Leu Gly Leu Gly Leu Gly Gln Val Val Cys Ser Val
    50                  55                  60

Ala Leu Phe Phe Tyr Phe Arg Ala Gln Met Asp Pro Asn Arg Ile Ser
65                  70                  75                  80

Glu Asp Gly Thr His Cys Ile Tyr Arg Ile Leu Arg Leu His Glu Asn
                85                  90                  95

Ala Asp Phe Gln Asp Thr Thr Leu Glu Ser Gln Asp Thr Lys Leu Ile
            100                 105                 110

Pro Asp Ser Cys Arg Arg Ile Lys Gln Ala Phe Gln Gly Ala Val Gln
        115                 120                 125

Lys Glu Leu Gln His Ile Val Gly Ser Gln His Ile Arg Ala Glu Lys
    130                 135                 140

Ala Met Val Asp Gly Ser Trp Leu Asp Leu Ala Lys Arg Ser Lys Leu
145                 150                 155                 160

Glu Ala Gln Pro Phe Ala His Leu Thr Ile Asn Ala Thr Asp Ile Pro
                165                 170                 175

Ser Gly Ser His Lys Val Ser Leu Ser Ser Trp Tyr His Asp Arg Gly
            180                 185                 190

Trp Ala Lys Ile Ser Asn Met Thr Phe Ser Asn Gly Lys Leu Ile Val
        195                 200                 205
```

```
Asn Gln Asp Gly Phe Tyr Tyr Leu Tyr Ala Asn Ile Cys Phe Arg His
    210                 215                 220

His Glu Thr Ser Gly Asp Leu Ala Thr Glu Tyr Leu Gln Leu Met Val
225                 230                 235                 240

Tyr Val Thr Lys Thr Ser Ile Lys Ile Pro Ser Ser His Thr Leu Met
                245                 250                 255

Lys Gly Gly Ser Thr Lys Tyr Trp Ser Gly Asn Ser Glu Phe His Phe
            260                 265                 270

Tyr Ser Ile Asn Val Gly Gly Phe Phe Lys Leu Arg Ser Gly Glu Glu
        275                 280                 285

Ile Ser Ile Glu Val Ser Asn Pro Ser Leu Leu Asp Pro Asp Gln Asp
    290                 295                 300

Ala Thr Tyr Phe Gly Ala Phe Lys Val Arg Asp Ile Asp
305                 310                 315


<210> SEQ ID NO 41
<211> LENGTH: 249
<212> TYPE: PRT
<213> ORGANISM: Homo sapiens

<400> SEQUENCE: 41

Met Ala Ala Arg Arg Ser Gln Arg Arg Arg Gly Arg Arg Gly Glu Pro
1               5                   10                  15

Gly Thr Ala Leu Leu Val Pro Leu Ala Leu Gly Leu Gly Leu Ala Leu
            20                  25                  30

Ala Cys Leu Gly Leu Leu Leu Ala Val Val Ser Leu Gly Ser Arg Ala
        35                  40                  45

Ser Leu Ser Ala Gln Glu Pro Ala Gln Glu Glu Leu Val Ala Glu Glu
    50                  55                  60

Asp Gln Asp Pro Ser Glu Leu Asn Pro Gln Thr Glu Glu Ser Gln Asp
65                  70                  75                  80

Pro Ala Pro Phe Leu Asn Arg Leu Val Arg Pro Arg Arg Ser Ala Pro
                85                  90                  95

Lys Gly Arg Lys Thr Arg Ala Arg Arg Ala Ile Ala Ala His Tyr Glu
            100                 105                 110

Val His Pro Arg Pro Gly Gln Asp Gly Ala Gln Ala Gly Val Asp Gly
        115                 120                 125

Thr Val Ser Gly Trp Glu Glu Ala Arg Ile Asn Ser Ser Ser Pro Leu
    130                 135                 140

Arg Tyr Asn Arg Gln Ile Gly Glu Phe Ile Val Thr Arg Ala Gly Leu
145                 150                 155                 160

Tyr Tyr Leu Tyr Cys Gln Val His Phe Asp Glu Gly Lys Ala Val Tyr
                165                 170                 175

Leu Lys Leu Asp Leu Leu Val Asp Gly Val Leu Ala Leu Arg Cys Leu
            180                 185                 190

Glu Glu Phe Ser Ala Thr Ala Ala Ser Ser Leu Gly Pro Gln Leu Arg
        195                 200                 205

Leu Cys Gln Val Ser Gly Leu Leu Ala Leu Arg Pro Gly Ser Ser Leu
    210                 215                 220

Arg Ile Arg Thr Leu Pro Trp Ala His Leu Lys Ala Ala Pro Phe Leu
225                 230                 235                 240

Thr Tyr Phe Gly Leu Phe Gln Val His
                245
```

<210> SEQ ID NO 42
<211> LENGTH: 250
<212> TYPE: PRT
<213> ORGANISM: Homo sapiens

<400> SEQUENCE: 42

```
Met Pro Ala Ser Ser Pro Phe Leu Leu Ala Pro Lys Gly Pro Pro Gly
1               5                   10                  15

Asn Met Gly Gly Pro Val Arg Glu Pro Ala Leu Ser Val Ala Leu Trp
            20                  25                  30

Leu Ser Trp Gly Ala Ala Leu Gly Ala Val Ala Cys Ala Met Ala Leu
        35                  40                  45

Leu Thr Gln Gln Thr Glu Leu Gln Ser Leu Arg Arg Glu Val Ser Arg
    50                  55                  60

Leu Gln Gly Thr Gly Gly Pro Ser Gln Asn Gly Glu Gly Tyr Pro Trp
65                  70                  75                  80

Gln Ser Leu Pro Glu Gln Ser Ser Asp Ala Leu Glu Ala Trp Glu Asn
                85                  90                  95

Gly Glu Arg Ser Arg Lys Arg Arg Ala Val Leu Thr Gln Lys Gln Lys
            100                 105                 110

Lys Gln His Ser Val Leu His Leu Val Pro Ile Asn Ala Thr Ser Lys
        115                 120                 125

Asp Asp Ser Asp Val Thr Glu Val Met Trp Gln Pro Ala Leu Arg Arg
    130                 135                 140

Gly Arg Gly Leu Gln Ala Gln Gly Tyr Gly Val Arg Ile Gln Asp Ala
145                 150                 155                 160

Gly Val Tyr Leu Leu Tyr Ser Gln Val Leu Phe Gln Asp Val Thr Phe
                165                 170                 175

Thr Met Gly Gln Val Val Ser Arg Glu Gly Gln Gly Arg Gln Glu Thr
            180                 185                 190

Leu Phe Arg Cys Ile Arg Ser Met Pro Ser His Pro Asp Arg Ala Tyr
        195                 200                 205

Asn Ser Cys Tyr Ser Ala Gly Val Phe His Leu His Gln Gly Asp Ile
    210                 215                 220

Leu Ser Val Ile Ile Pro Arg Ala Arg Ala Lys Leu Asn Leu Ser Pro
225                 230                 235                 240

His Gly Thr Phe Leu Gly Phe Val Lys Leu
                245                 250
```

<210> SEQ ID NO 43
<211> LENGTH: 285
<212> TYPE: PRT
<213> ORGANISM: Homo sapiens

<400> SEQUENCE: 43

```
Met Asp Asp Ser Thr Glu Arg Glu Gln Ser Arg Leu Thr Ser Cys Leu
1               5                   10                  15

Lys Lys Arg Glu Glu Met Lys Leu Lys Glu Cys Val Ser Ile Leu Pro
            20                  25                  30

Arg Lys Glu Ser Pro Ser Val Arg Ser Ser Lys Asp Gly Lys Leu Leu
        35                  40                  45

Ala Ala Thr Leu Leu Leu Ala Leu Leu Ser Cys Cys Leu Thr Val Val
    50                  55                  60

Ser Phe Tyr Gln Val Ala Ala Leu Gln Gly Asp Leu Ala Ser Leu Arg
65                  70                  75                  80

Ala Glu Leu Gln Gly His His Ala Glu Lys Leu Pro Ala Gly Ala Gly
```

```
                85                  90                  95

Ala Pro Lys Ala Gly Leu Glu Glu Ala Pro Ala Val Thr Ala Gly Leu
            100                 105                 110

Lys Ile Phe Glu Pro Pro Ala Pro Gly Glu Gly Asn Ser Ser Gln Asn
        115                 120                 125

Ser Arg Asn Lys Arg Ala Val Gln Gly Pro Glu Glu Thr Val Thr Gln
    130                 135                 140

Asp Cys Leu Gln Leu Ile Ala Asp Ser Glu Thr Pro Thr Ile Gln Lys
145                 150                 155                 160

Gly Ser Tyr Thr Phe Val Pro Trp Leu Leu Ser Phe Lys Arg Gly Ser
                165                 170                 175

Ala Leu Glu Glu Lys Glu Asn Lys Ile Leu Val Lys Glu Thr Gly Tyr
            180                 185                 190

Phe Phe Ile Tyr Gly Gln Val Leu Tyr Thr Asp Lys Thr Tyr Ala Met
        195                 200                 205

Gly His Leu Ile Gln Arg Lys Lys Val His Val Phe Gly Asp Glu Leu
    210                 215                 220

Ser Leu Val Thr Leu Phe Arg Cys Ile Gln Asn Met Pro Glu Thr Leu
225                 230                 235                 240

Pro Asn Asn Ser Cys Tyr Ser Ala Gly Ile Ala Lys Leu Glu Glu Gly
                245                 250                 255

Asp Glu Leu Gln Leu Ala Ile Pro Arg Glu Asn Ala Gln Ile Ser Leu
            260                 265                 270

Asp Gly Asp Val Thr Phe Phe Gly Ala Leu Lys Leu Leu
        275                 280                 285
```

<210> SEQ ID NO 44
<211> LENGTH: 296
<212> TYPE: PRT
<213> ORGANISM: Homo sapiens

<400> SEQUENCE: 44

```
Met Glu Ser Met Ala Val Ala Thr Asp Gly Gly Glu Arg Pro Gly Val
1               5                   10                  15

Pro Ala Gly Ser Gly Leu Ser Ala Ser Gln Arg Arg Ala Glu Leu Arg
            20                  25                  30

Arg Arg Lys Leu Leu Met Asn Ser Glu Gln Arg Ile Asn Arg Ile Met
        35                  40                  45

Gly Phe His Arg Pro Gly Ser Gly Ala Glu Glu Glu Ser Gln Thr Lys
    50                  55                  60

Ser Lys Gln Gln Asp Ser Asp Lys Leu Asn Ser Leu Ser Val Pro Ser
65                  70                  75                  80

Val Ser Lys Arg Val Val Leu Gly Asp Ser Val Ser Thr Gly Thr Thr
                85                  90                  95

Asp Gln Gln Gly Gly Val Ala Glu Val Lys Gly Thr Gln Leu Gly Asp
            100                 105                 110

Lys Leu Asp Ser Phe Ile Lys Pro Pro Glu Cys Ser Ser Asp Val Asn
        115                 120                 125

Leu Glu Leu Arg Gln Arg Asn Arg Gly Asp Leu Thr Ala Asp Ser Val
    130                 135                 140

Gln Arg Gly Ser Arg His Gly Leu Glu Gln Tyr Leu Ser Arg Phe Glu
145                 150                 155                 160

Glu Ala Met Lys Leu Arg Lys Gln Leu Ile Ser Glu Lys Pro Ser Gln
                165                 170                 175
```

```
Glu Asp Gly Asn Thr Thr Glu Glu Phe Asp Ser Phe Arg Ile Phe Arg
            180                 185                 190

Leu Val Gly Cys Ala Leu Leu Ala Leu Gly Val Arg Ala Phe Val Cys
        195                 200                 205

Lys Tyr Leu Ser Ile Phe Ala Pro Phe Leu Thr Leu Gln Leu Ala Tyr
    210                 215                 220

Met Gly Leu Tyr Lys Tyr Phe Pro Lys Ser Glu Lys Lys Ile Lys Thr
225                 230                 235                 240

Thr Val Leu Thr Ala Ala Leu Leu Leu Ser Gly Ile Pro Ala Glu Val
                245                 250                 255

Ile Asn Arg Ser Met Asp Thr Tyr Ser Lys Met Gly Glu Val Phe Thr
            260                 265                 270

Asp Leu Cys Val Tyr Phe Phe Thr Phe Ile Phe Cys His Glu Leu Leu
        275                 280                 285

Asp Tyr Trp Gly Ser Glu Val Pro
    290                 295


<210> SEQ ID NO 45
<211> LENGTH: 241
<212> TYPE: PRT
<213> ORGANISM: Homo sapiens

<400> SEQUENCE: 45

Met Ser Met Leu Phe Tyr Thr Leu Ile Thr Ala Phe Leu Ile Gly Ile
1               5                   10                  15

Gln Ala Glu Pro His Ser Glu Ser Asn Val Pro Ala Gly His Thr Ile
            20                  25                  30

Pro Gln Ala His Trp Thr Lys Leu Gln His Ser Leu Asp Thr Ala Leu
        35                  40                  45

Arg Arg Ala Arg Ser Ala Pro Ala Ala Ala Ile Ala Ala Arg Val Ala
    50                  55                  60

Gly Gln Thr Arg Asn Ile Thr Val Asp Pro Arg Leu Phe Lys Lys Arg
65                  70                  75                  80

Arg Leu Arg Ser Pro Arg Val Leu Phe Ser Thr Gln Pro Pro Arg Glu
                85                  90                  95

Ala Ala Asp Thr Gln Asp Leu Asp Phe Glu Val Gly Gly Ala Ala Pro
            100                 105                 110

Phe Asn Arg Thr His Arg Ser Lys Arg Ser Ser Ser His Pro Ile Phe
        115                 120                 125

His Arg Gly Glu Phe Ser Val Cys Asp Ser Val Ser Val Trp Val Gly
    130                 135                 140

Asp Lys Thr Thr Ala Thr Asp Ile Lys Gly Lys Glu Val Met Val Leu
145                 150                 155                 160

Gly Glu Val Asn Ile Asn Asn Ser Val Phe Lys Gln Tyr Phe Phe Glu
                165                 170                 175

Thr Lys Cys Arg Asp Pro Asn Pro Val Asp Ser Gly Cys Arg Gly Ile
            180                 185                 190

Asp Ser Lys His Trp Asn Ser Tyr Cys Thr Thr Thr His Thr Phe Val
        195                 200                 205

Lys Ala Leu Thr Met Asp Gly Lys Gln Ala Ala Trp Arg Phe Ile Arg
    210                 215                 220

Ile Asp Thr Ala Cys Val Cys Val Leu Ser Arg Lys Ala Val Arg Arg
225                 230                 235                 240

Ala
```

<210> SEQ ID NO 46
<211> LENGTH: 247
<212> TYPE: PRT
<213> ORGANISM: Homo sapiens

<400> SEQUENCE: 46

```
Met Thr Ile Leu Phe Leu Thr Met Val Ile Ser Tyr Phe Gly Cys Met
1               5                   10                  15

Lys Ala Ala Pro Met Lys Glu Ala Asn Ile Arg Gly Gln Gly Gly Leu
            20                  25                  30

Ala Tyr Pro Gly Val Arg Thr His Gly Thr Leu Glu Ser Val Asn Gly
        35                  40                  45

Pro Lys Ala Gly Ser Arg Gly Leu Thr Ser Leu Ala Asp Thr Phe Glu
    50                  55                  60

His Val Ile Glu Glu Leu Leu Asp Glu Asp Gln Lys Val Arg Pro Asn
65                  70                  75                  80

Glu Glu Asn Asn Lys Asp Ala Asp Leu Tyr Thr Ser Arg Val Met Leu
                85                  90                  95

Ser Ser Gln Val Pro Leu Glu Pro Pro Leu Leu Phe Leu Leu Glu Glu
            100                 105                 110

Tyr Lys Asn Tyr Leu Asp Ala Ala Asn Met Ser Met Arg Val Arg Arg
        115                 120                 125

His Ser Asp Pro Ala Arg Arg Gly Glu Leu Ser Val Cys Asp Ser Ile
    130                 135                 140

Ser Glu Trp Val Thr Ala Ala Asp Lys Lys Thr Ala Val Asp Met Ser
145                 150                 155                 160

Gly Gly Thr Val Thr Val Leu Glu Lys Val Pro Val Ser Lys Gly Gln
                165                 170                 175

Leu Lys Gln Tyr Phe Tyr Glu Thr Lys Cys Asn Pro Met Gly Tyr Thr
            180                 185                 190

Lys Glu Gly Cys Arg Gly Ile Asp Lys Arg His Trp Asn Ser Gln Cys
        195                 200                 205

Arg Thr Thr Gln Ser Tyr Val Arg Ala Leu Thr Met Asp Ser Lys Lys
    210                 215                 220

Arg Ile Gly Trp Arg Phe Ile Arg Ile Asp Thr Ser Cys Val Cys Thr
225                 230                 235                 240

Leu Thr Ile Lys Arg Gly Arg
                245
```

<210> SEQ ID NO 47
<211> LENGTH: 257
<212> TYPE: PRT
<213> ORGANISM: Homo sapiens

<400> SEQUENCE: 47

```
Met Ser Ile Leu Phe Tyr Val Ile Phe Leu Ala Tyr Leu Arg Gly Ile
1               5                   10                  15

Gln Gly Asn Asn Met Asp Gln Arg Ser Leu Pro Glu Asp Ser Leu Asn
            20                  25                  30

Ser Leu Ile Ile Lys Leu Ile Gln Ala Asp Ile Leu Lys Asn Lys Leu
        35                  40                  45

Ser Lys Gln Met Val Asp Val Lys Glu Asn Tyr Gln Ser Thr Leu Pro
    50                  55                  60

Lys Ala Glu Ala Pro Arg Glu Pro Glu Arg Gly Gly Pro Ala Lys Ser
65                  70                  75                  80
```

```
Ala Phe Gln Pro Val Ile Ala Met Asp Thr Glu Leu Leu Arg Gln Gln
                85                  90                  95

Arg Arg Tyr Asn Ser Pro Arg Val Leu Leu Ser Asp Ser Thr Pro Leu
            100                 105                 110

Glu Pro Pro Pro Leu Tyr Leu Met Glu Asp Tyr Val Gly Ser Pro Val
        115                 120                 125

Val Ala Asn Arg Thr Ser Arg Arg Lys Arg Tyr Ala Glu His Lys Ser
    130                 135                 140

His Arg Gly Glu Tyr Ser Val Cys Asp Ser Glu Ser Leu Trp Val Thr
145                 150                 155                 160

Asp Lys Ser Ser Ala Ile Asp Ile Arg Gly His Gln Val Thr Val Leu
                165                 170                 175

Gly Glu Ile Lys Thr Gly Asn Ser Pro Val Lys Gln Tyr Phe Tyr Glu
            180                 185                 190

Thr Arg Cys Lys Glu Ala Arg Pro Val Lys Asn Gly Cys Arg Gly Ile
        195                 200                 205

Asp Asp Lys His Trp Asn Ser Gln Cys Lys Thr Ser Gln Thr Tyr Val
    210                 215                 220

Arg Ala Leu Thr Ser Glu Asn Asn Lys Leu Val Gly Trp Arg Trp Ile
225                 230                 235                 240

Arg Ile Asp Thr Ser Cys Val Cys Ala Leu Ser Arg Lys Ile Gly Arg
                245                 250                 255

Thr


<210> SEQ ID NO 48
<211> LENGTH: 210
<212> TYPE: PRT
<213> ORGANISM: Homo sapiens

<400> SEQUENCE: 48

Met Leu Pro Leu Pro Ser Cys Ser Leu Pro Ile Leu Leu Leu Phe Leu
1               5                   10                  15

Leu Pro Ser Val Pro Ile Glu Ser Gln Pro Pro Pro Ser Thr Leu Pro
            20                  25                  30

Pro Phe Leu Ala Pro Glu Trp Asp Leu Leu Ser Pro Arg Val Val Leu
        35                  40                  45

Ser Arg Gly Ala Pro Ala Gly Pro Pro Leu Leu Phe Leu Leu Glu Ala
    50                  55                  60

Gly Ala Phe Arg Glu Ser Ala Gly Ala Pro Ala Asn Arg Ser Arg Arg
65                  70                  75                  80

Gly Val Ser Glu Thr Ala Pro Ala Ser Arg Arg Gly Glu Leu Ala Val
                85                  90                  95

Cys Asp Ala Val Ser Gly Trp Val Thr Asp Arg Arg Thr Ala Val Asp
            100                 105                 110

Leu Arg Gly Arg Glu Val Glu Val Leu Gly Glu Val Pro Ala Ala Gly
        115                 120                 125

Gly Ser Pro Leu Arg Gln Tyr Phe Phe Glu Thr Arg Cys Lys Ala Asp
    130                 135                 140

Asn Ala Glu Glu Gly Gly Pro Gly Ala Gly Gly Gly Gly Cys Arg Gly
145                 150                 155                 160

Val Asp Arg Arg His Trp Val Ser Glu Cys Lys Ala Lys Gln Ser Tyr
                165                 170                 175

Val Arg Ala Leu Thr Ala Asp Ala Gln Gly Arg Val Gly Trp Arg Trp
            180                 185                 190
```

```
Ile Arg Ile Asp Thr Ala Cys Val Cys Thr Leu Leu Ser Arg Thr Gly
        195                 200                 205

Arg Ala
    210


<210> SEQ ID NO 49
<211> LENGTH: 126
<212> TYPE: PRT
<213> ORGANISM: Homo sapiens

<400> SEQUENCE: 49

Gly His Thr Ala Asn Lys Pro Cys Leu Ala Lys Phe Glu Leu Leu Thr
1               5                   10                  15

Ser Lys Trp Gln Met Thr Ser Arg Lys Pro Pro Cys Val Asn Ser Leu
            20                  25                  30

Pro Glu Gly Lys Leu Lys Ile Leu Gln Asp Gly Leu Tyr Leu Ile Tyr
        35                  40                  45

Gly Gln Val Ala Pro Ser Thr Ala Tyr Lys Gly Val Ala Pro Phe Ala
    50                  55                  60

Val Gln Leu Arg Lys Asn Glu Ala Met Leu Gln Thr Leu Thr Ser Asn
65                  70                  75                  80

Ser Thr Ile Tyr Asp Val Gly Gly Thr Tyr Glu Phe His Ala Gly Asp
                85                  90                  95

Ile Ile Asp Leu Ile Phe Asp Asp Glu His Gln Val Leu Lys Asn Asn
            100                 105                 110

Thr Tyr Trp Gly Ile Val Leu Leu Ala Asn Leu Phe Ile Ser
        115                 120                 125


<210> SEQ ID NO 50
<211> LENGTH: 389
<212> TYPE: PRT
<213> ORGANISM: Homo sapiens

<400> SEQUENCE: 50

Met Gly Tyr Pro Glu Val Glu Arg Arg Glu Leu Leu Pro Ala Ala Ala
1               5                   10                  15

Pro Arg Glu Arg Gly Ser Gln Gly Cys Gly Cys Gly Gly Ala Pro Ala
            20                  25                  30

Arg Ala Gly Glu Gly Asn Ser Cys Leu Leu Phe Leu Gly Phe Phe Gly
        35                  40                  45

Leu Ser Leu Ala Leu His Leu Leu Thr Leu Cys Cys Tyr Leu Glu Leu
    50                  55                  60

Arg Ser Glu Leu Arg Arg Glu Arg Gly Ala Glu Ser Arg Leu Gly Gly
65                  70                  75                  80

Ser Gly Thr Pro Gly Thr Ser Gly Thr Leu Ser Ser Leu Gly Gly Leu
                85                  90                  95

Asp Pro Asp Ser Pro Ile Thr Ser His Leu Gly Gln Pro Ser Pro Lys
            100                 105                 110

Gln Gln Pro Leu Glu Pro Gly Glu Ala Ala Leu His Ser Asp Ser Gln
        115                 120                 125

Asp Gly His Gln Met Ala Leu Leu Asn Phe Phe Phe Pro Asp Glu Lys
    130                 135                 140

Pro Tyr Ser Glu Glu Glu Ser Arg Arg Val Arg Arg Asn Lys Arg Ser
145                 150                 155                 160

Lys Ser Asn Glu Gly Ala Asp Gly Pro Val Lys Asn Lys Lys Lys Gly
                165                 170                 175
```

```
Lys Lys Ala Gly Pro Pro Gly Pro Asn Gly Pro Pro Gly Pro Pro Gly
            180                 185                 190

Pro Pro Gly Pro Gln Gly Pro Pro Gly Ile Pro Gly Ile Pro Gly Ile
        195                 200                 205

Pro Gly Thr Thr Val Met Gly Pro Pro Gly Pro Pro Gly Pro Pro Gly
    210                 215                 220

Pro Gln Gly Pro Pro Gly Leu Gln Gly Pro Ser Gly Ala Ala Asp Lys
225                 230                 235                 240

Ala Gly Thr Arg Glu Asn Gln Pro Ala Val Val His Leu Gln Gly Gln
                245                 250                 255

Gly Ser Ala Ile Gln Val Lys Asn Asp Leu Ser Gly Gly Val Leu Asn
            260                 265                 270

Asp Trp Ser Arg Ile Thr Met Asn Pro Lys Val Phe Lys Leu His Pro
        275                 280                 285

Arg Ser Gly Glu Leu Glu Val Leu Val Asp Gly Thr Tyr Phe Ile Tyr
    290                 295                 300

Ser Gln Val Tyr Tyr Ile Asn Phe Thr Asp Phe Ala Ser Tyr Glu Val
305                 310                 315                 320

Val Val Asp Glu Lys Pro Phe Leu Gln Cys Thr Arg Ser Ile Glu Thr
                325                 330                 335

Gly Lys Thr Asn Tyr Asn Thr Cys Tyr Thr Ala Gly Val Cys Leu Leu
            340                 345                 350

Lys Ala Arg Gln Lys Ile Ala Val Lys Met Val His Ala Asp Ile Ser
        355                 360                 365

Ile Asn Met Ser Lys His Thr Thr Phe Phe Gly Ala Ile Arg Leu Gly
    370                 375                 380

Glu Ala Pro Ala Ser
385


<210> SEQ ID NO 51
<211> LENGTH: 121
<212> TYPE: PRT
<213> ORGANISM: Artificial Sequence
<220> FEATURE:
<223> OTHER INFORMATION: VH of antibody SF2

<400> SEQUENCE: 51

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Lys Asp Tyr
            20                  25                  30

Thr Met His Trp Val Arg Gln Ala Pro Gly Gln Gly Leu Glu Trp Ile
        35                  40                  45

Gly Gly Ile Tyr Pro Asn Asn Gly Gly Ser Thr Tyr Asn Gln Asn Phe
    50                  55                  60

Lys Asp Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Met Gly Tyr His Gly Pro His Leu Asp Phe Asp Val Trp Gly
            100                 105                 110

Gln Gly Thr Thr Val Thr Val Ser Ser
        115                 120


<210> SEQ ID NO 52
<211> LENGTH: 107
```

```
<212> TYPE: PRT
<213> ORGANISM: Artificial Sequence
<220> FEATURE:
<223> OTHER INFORMATION: VL of antibody SF2

<400> SEQUENCE: 52

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Gly Ala Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ile Asn Tyr Pro Leu
                85                  90                  95

Thr Phe Gly Gly Gly Thr Lys Val Glu Ile Lys
            100                 105


<210> SEQ ID NO 53
<211> LENGTH: 121
<212> TYPE: PRT
<213> ORGANISM: Artificial Sequence
<220> FEATURE:
<223> OTHER INFORMATION: VH of 12H3VH1VL1

<400> SEQUENCE: 53

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Lys Asp Tyr
            20                  25                  30

Thr Met His Trp Val Arg Gln Ala Pro Gly Gln Gly Leu Glu Trp Met
        35                  40                  45

Gly Gly Ile Tyr Pro Asn Asn Gly Gly Ser Thr Tyr Asn Gln Asn Phe
    50                  55                  60

Lys Asp Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Met Gly Tyr His Gly Pro His Leu Asp Phe Asp Val Trp Gly
            100                 105                 110

Gln Gly Thr Thr Val Thr Val Ser Ser
        115                 120


<210> SEQ ID NO 54
<211> LENGTH: 107
<212> TYPE: PRT
<213> ORGANISM: Artificial Sequence
<220> FEATURE:
<223> OTHER INFORMATION: VL of 12H3VH1VL1

<400> SEQUENCE: 54

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Gly Ala Ala
            20                  25                  30

Val Ala Trp Tyr Gln Gln Lys Pro Gly Lys Ala Pro Lys Leu Leu Ile
```

```
        35                  40                  45

Tyr Trp Ala Ser Thr Arg His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ile Asn Tyr Pro Leu
                85                  90                  95

Thr Phe Gly Gly Gly Thr Lys Val Glu Ile Lys
            100                 105


<210> SEQ ID NO 55
<211> LENGTH: 119
<212> TYPE: PRT
<213> ORGANISM: Artificial Sequence
<220> FEATURE:
<223> OTHER INFORMATION: VH of 20E5VH3VL2

<400> SEQUENCE: 55

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Val Met His Trp Val Arg Gln Ala Pro Gly Gln Arg Leu Glu Trp Ile
        35                  40                  45

Gly Tyr Ile Asn Pro Tyr Asn Asp Gly Thr Lys Tyr Asn Glu Lys Phe
    50                  55                  60

Lys Gly Arg Ala Thr Leu Thr Ser Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Asn Tyr Tyr Gly Ser Ser Leu Ser Met Asp Tyr Trp Gly Gln Gly
            100                 105                 110

Thr Leu Val Thr Val Ser Ser
        115


<210> SEQ ID NO 56
<211> LENGTH: 107
<212> TYPE: PRT
<213> ORGANISM: Artificial Sequence
<220> FEATURE:
<223> OTHER INFORMATION: VL of 20E5VH3VL2

<400> SEQUENCE: 56

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Phe Cys Gln Gln Gly Asn Thr Leu Pro Trp
                85                  90                  95

Thr Phe Gly Gln Gly Thr Lys Val Glu Ile Lys
            100                 105
```

<210> SEQ ID NO 57
<211> LENGTH: 116
<212> TYPE: PRT
<213> ORGANISM: Artificial Sequence
<220> FEATURE:
<223> OTHER INFORMATION: VH of M9

<400> SEQUENCE: 57

```
Gln Leu Gln Leu Gln Glu Ser Gly Pro Gly Leu Val Lys Pro Ser Glu
1               5                   10                  15

Ile Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Asn Ile Tyr Tyr Arg Gly Asp Thr Tyr Tyr Ser Pro Ser
    50                  55                  60

Leu Lys Ser Arg Val Thr Ile Ser Val Asp Thr Ser Lys Asn Gln Phe
65                  70                  75                  80

Ser Leu Lys Leu Asn Ser Val Thr Ala Ala Asp Thr Ala Val Tyr Tyr
                85                  90                  95

Cys Ala Lys Gly Phe Arg Phe Asp Tyr Trp Gly Gln Gly Thr Leu Val
            100                 105                 110

Thr Val Ser Ser
        115
```

<210> SEQ ID NO 58
<211> LENGTH: 110
<212> TYPE: PRT
<213> ORGANISM: Artificial Sequence
<220> FEATURE:
<223> OTHER INFORMATION: VL of M9

<400> SEQUENCE: 58

```
Gln Ser Ala Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Val Ser Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Ala Gly Ser
                85                  90                  95

Asn Asn Leu Val Phe Gly Gly Gly Thr Lys Leu Thr Val Leu
            100                 105                 110
```

<210> SEQ ID NO 59
<211> LENGTH: 374
<212> TYPE: PRT
<213> ORGANISM: Homo sapiens

<400> SEQUENCE: 59

```
Met Trp Phe Leu Thr Thr Leu Leu Leu Trp Val Pro Val Asp Gly Gln
1               5                   10                  15

Val Asp Thr Thr Lys Ala Val Ile Thr Leu Gln Pro Pro Trp Val Ser
            20                  25                  30
```

```
Val Phe Gln Glu Glu Thr Val Thr Leu His Cys Glu Val Leu His Leu
        35                  40                  45

Pro Gly Ser Ser Ser Thr Gln Trp Phe Leu Asn Gly Thr Ala Thr Gln
    50                  55                  60

Thr Ser Thr Pro Ser Tyr Arg Ile Thr Ser Ala Ser Val Asn Asp Ser
65                  70                  75                  80

Gly Glu Tyr Arg Cys Gln Arg Gly Leu Ser Gly Arg Ser Asp Pro Ile
                85                  90                  95

Gln Leu Glu Ile His Arg Gly Trp Leu Leu Leu Gln Val Ser Ser Arg
            100                 105                 110

Val Phe Thr Glu Gly Glu Pro Leu Ala Leu Arg Cys His Ala Trp Lys
        115                 120                 125

Asp Lys Leu Val Tyr Asn Val Leu Tyr Tyr Arg Asn Gly Lys Ala Phe
    130                 135                 140

Lys Phe Phe His Trp Asn Ser Asn Leu Thr Ile Leu Lys Thr Asn Ile
145                 150                 155                 160

Ser His Asn Gly Thr Tyr His Cys Ser Gly Met Gly Lys His Arg Tyr
                165                 170                 175

Thr Ser Ala Gly Ile Ser Val Thr Val Lys Glu Leu Phe Pro Ala Pro
            180                 185                 190

Val Leu Asn Ala Ser Val Thr Ser Pro Leu Leu Glu Gly Asn Leu Val
        195                 200                 205

Thr Leu Ser Cys Glu Thr Lys Leu Leu Leu Gln Arg Pro Gly Leu Gln
    210                 215                 220

Leu Tyr Phe Ser Phe Tyr Met Gly Ser Lys Thr Leu Arg Gly Arg Asn
225                 230                 235                 240

Thr Ser Ser Glu Tyr Gln Ile Leu Thr Ala Arg Arg Glu Asp Ser Gly
                245                 250                 255

Leu Tyr Trp Cys Glu Ala Ala Thr Glu Asp Gly Asn Val Leu Lys Arg
            260                 265                 270

Ser Pro Glu Leu Glu Leu Gln Val Leu Gly Leu Gln Leu Pro Thr Pro
        275                 280                 285

Val Trp Phe His Val Leu Phe Tyr Leu Ala Val Gly Ile Met Phe Leu
    290                 295                 300

Val Asn Thr Val Leu Trp Val Thr Ile Arg Lys Glu Leu Lys Arg Lys
305                 310                 315                 320

Lys Lys Trp Asp Leu Glu Ile Ser Leu Asp Ser Gly His Glu Lys Lys
                325                 330                 335

Val Ile Ser Ser Leu Gln Glu Asp Arg His Leu Glu Glu Glu Leu Lys
            340                 345                 350

Cys Gln Glu Gln Lys Glu Glu Gln Leu Gln Glu Gly Val His Arg Lys
        355                 360                 365

Glu Pro Gln Gly Ala Thr
    370


<210> SEQ ID NO 60
<211> LENGTH: 316
<212> TYPE: PRT
<213> ORGANISM: Homo sapiens

<400> SEQUENCE: 60

Met Thr Met Glu Thr Gln Met Ser Gln Asn Val Cys Pro Arg Asn Leu
1               5                   10                  15

Trp Leu Leu Gln Pro Leu Thr Val Leu Leu Leu Leu Ala Ser Ala Asp
            20                  25                  30
```

```
Ser Gln Ala Ala Pro Pro Lys Ala Val Leu Lys Leu Glu Pro Pro Trp
        35                  40                  45

Ile Asn Val Leu Gln Glu Asp Ser Val Thr Leu Thr Cys Gln Gly Ala
    50                  55                  60

Arg Ser Pro Glu Ser Asp Ser Ile Gln Trp Phe His Asn Gly Asn Leu
65                  70                  75                  80

Ile Pro Thr His Thr Gln Pro Ser Tyr Arg Phe Lys Ala Asn Asn Asn
                85                  90                  95

Asp Ser Gly Glu Tyr Thr Cys Gln Thr Gly Gln Thr Ser Leu Ser Asp
            100                 105                 110

Pro Val His Leu Thr Val Leu Ser Glu Trp Leu Val Leu Gln Thr Pro
        115                 120                 125

His Leu Glu Phe Gln Glu Gly Glu Thr Ile Met Leu Arg Cys His Ser
    130                 135                 140

Trp Lys Asp Lys Pro Leu Val Lys Val Thr Phe Phe Gln Asn Gly Lys
145                 150                 155                 160

Ser Gln Lys Phe Ser His Leu Asp Pro Thr Phe Ser Ile Pro Gln Ala
                165                 170                 175

Asn His Ser His Ser Gly Asp Tyr His Cys Thr Gly Asn Ile Gly Tyr
            180                 185                 190

Thr Leu Phe Ser Ser Lys Pro Val Thr Ile Thr Val Gln Val Pro Ser
        195                 200                 205

Met Gly Ser Ser Ser Pro Met Gly Ile Ile Val Ala Val Val Ile Ala
    210                 215                 220

Thr Ala Val Ala Ala Ile Val Ala Ala Val Val Ala Leu Ile Tyr Cys
225                 230                 235                 240

Arg Lys Lys Arg Ile Ser Ala Asn Ser Thr Asp Pro Val Lys Ala Ala
                245                 250                 255

Gln Phe Glu Pro Pro Gly Arg Gln Met Ile Ala Ile Arg Lys Arg Gln
            260                 265                 270

Leu Glu Glu Thr Asn Asn Asp Tyr Glu Thr Ala Asp Gly Gly Tyr Met
        275                 280                 285

Thr Leu Asn Pro Arg Ala Pro Thr Asp Asp Asp Lys Asn Ile Tyr Leu
    290                 295                 300

Thr Leu Pro Pro Asn Asp His Val Asn Ser Asn Asn
305                 310                 315
```

<210> SEQ ID NO 61
<211> LENGTH: 310
<212> TYPE: PRT
<213> ORGANISM: Homo sapiens

<400> SEQUENCE: 61

```
Met Gly Ile Leu Ser Phe Leu Pro Val Leu Ala Thr Glu Ser Asp Trp
1               5                   10                  15

Ala Asp Cys Lys Ser Pro Gln Pro Trp Gly His Met Leu Leu Trp Thr
            20                  25                  30

Ala Val Leu Phe Leu Ala Pro Val Ala Gly Thr Pro Ala Ala Pro Pro
        35                  40                  45

Lys Ala Val Leu Lys Leu Glu Pro Gln Trp Ile Asn Val Leu Gln Glu
    50                  55                  60

Asp Ser Val Thr Leu Thr Cys Arg Gly Thr His Ser Pro Glu Ser Asp
65                  70                  75                  80

Ser Ile Gln Trp Phe His Asn Gly Asn Leu Ile Pro Thr His Thr Gln
```

```
                85                  90                  95

Pro Ser Tyr Arg Phe Lys Ala Asn Asn Asn Asp Ser Gly Glu Tyr Thr
            100                 105                 110

Cys Gln Thr Gly Gln Thr Ser Leu Ser Asp Pro Val His Leu Thr Val
        115                 120                 125

Leu Ser Glu Trp Leu Val Leu Gln Thr Pro His Leu Glu Phe Gln Glu
    130                 135                 140

Gly Glu Thr Ile Val Leu Arg Cys His Ser Trp Lys Asp Lys Pro Leu
145                 150                 155                 160

Val Lys Val Thr Phe Phe Gln Asn Gly Lys Ser Lys Lys Phe Ser Arg
                165                 170                 175

Ser Asp Pro Asn Phe Ser Ile Pro Gln Ala Asn His Ser His Ser Gly
            180                 185                 190

Asp Tyr His Cys Thr Gly Asn Ile Gly Tyr Thr Leu Tyr Ser Ser Lys
        195                 200                 205

Pro Val Thr Ile Thr Val Gln Ala Pro Ser Ser Ser Pro Met Gly Ile
    210                 215                 220

Ile Val Ala Val Val Thr Gly Ile Ala Val Ala Ala Ile Val Ala Ala
225                 230                 235                 240

Val Val Ala Leu Ile Tyr Cys Arg Lys Lys Arg Ile Ser Ala Leu Pro
                245                 250                 255

Gly Tyr Pro Glu Cys Arg Glu Met Gly Glu Thr Leu Pro Glu Lys Pro
            260                 265                 270

Ala Asn Pro Thr Asn Pro Asp Glu Ala Asp Lys Val Gly Ala Glu Asn
        275                 280                 285

Thr Ile Thr Tyr Ser Leu Leu Met His Pro Asp Ala Leu Glu Glu Pro
    290                 295                 300

Asp Asp Gln Asn Arg Ile
305                 310


<210> SEQ ID NO 62
<211> LENGTH: 359
<212> TYPE: PRT
<213> ORGANISM: Homo sapiens

<400> SEQUENCE: 62

Met Ala Glu Gly Thr Leu Trp Gln Ile Leu Cys Val Ser Ser Asp Ala
1               5                   10                  15

Gln Pro Gln Thr Phe Glu Gly Val Lys Gly Ala Asp Pro Pro Thr Leu
            20                  25                  30

Pro Pro Gly Ser Phe Leu Pro Gly Pro Val Leu Trp Trp Gly Ser Leu
        35                  40                  45

Ala Arg Leu Gln Thr Glu Lys Ser Asp Glu Val Ser Arg Lys Gly Asn
    50                  55                  60

Trp Trp Val Thr Glu Met Gly Gly Gly Ala Gly Glu Arg Leu Phe Thr
65                  70                  75                  80

Ser Ser Cys Leu Val Gly Leu Val Pro Leu Gly Leu Arg Ile Ser Leu
                85                  90                  95

Val Thr Cys Pro Leu Gln Cys Gly Ile Met Trp Gln Leu Leu Leu Pro
            100                 105                 110

Thr Ala Leu Leu Leu Leu Val Ser Ala Gly Met Arg Thr Glu Asp Leu
        115                 120                 125

Pro Lys Ala Val Val Phe Leu Glu Pro Gln Trp Tyr Arg Val Leu Glu
    130                 135                 140
```

```
Lys Asp Ser Val Thr Leu Lys Cys Gln Gly Ala Tyr Ser Pro Glu Asp
145                 150                 155                 160

Asn Ser Thr Gln Trp Phe His Asn Glu Ser Leu Ile Ser Ser Gln Ala
                165                 170                 175

Ser Ser Tyr Phe Ile Asp Ala Ala Thr Val Asp Asp Ser Gly Glu Tyr
            180                 185                 190

Arg Cys Gln Thr Asn Leu Ser Thr Leu Ser Asp Pro Val Gln Leu Glu
        195                 200                 205

Val His Ile Gly Trp Leu Leu Leu Gln Ala Pro Arg Trp Val Phe Lys
    210                 215                 220

Glu Glu Asp Pro Ile His Leu Arg Cys His Ser Trp Lys Asn Thr Ala
225                 230                 235                 240

Leu His Lys Val Thr Tyr Leu Gln Asn Gly Lys Gly Arg Lys Tyr Phe
                245                 250                 255

His His Asn Ser Asp Phe Tyr Ile Pro Lys Ala Thr Leu Lys Asp Ser
            260                 265                 270

Gly Ser Tyr Phe Cys Arg Gly Leu Phe Gly Ser Lys Asn Val Ser Ser
        275                 280                 285

Glu Thr Val Asn Ile Thr Ile Thr Gln Gly Leu Ala Val Ser Thr Ile
    290                 295                 300

Ser Ser Phe Phe Pro Pro Gly Tyr Gln Val Ser Phe Cys Leu Val Met
305                 310                 315                 320

Val Leu Leu Phe Ala Val Asp Thr Gly Leu Tyr Phe Ser Val Lys Thr
                325                 330                 335

Asn Ile Arg Ser Ser Thr Arg Asp Trp Lys Asp His Lys Phe Lys Trp
            340                 345                 350

Arg Lys Asp Pro Gln Asp Lys
        355
```

<210> SEQ ID NO 63
<211> LENGTH: 330
<212> TYPE: PRT
<213> ORGANISM: Artificial Sequence
<220> FEATURE:
<223> OTHER INFORMATION: IgG1 with E345R mutation

<400> SEQUENCE: 63

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140
```

```
Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Arg Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 64
<211> LENGTH: 330
<212> TYPE: PRT
<213> ORGANISM: Artificial Sequence
<220> FEATURE:
<223> OTHER INFORMATION: IgG1 with E430G mutation

<400> SEQUENCE: 64

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175
```

```
Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Gly Ala Leu His Asn His Tyr Thr
305                 310                 315                 320

Gln Lys Ser Leu Ser Leu Ser Pro Gly Lys
                325                 330
```

<210> SEQ ID NO 65
<211> LENGTH: 330
<212> TYPE: PRT
<213> ORGANISM: Artificial Sequence
<220> FEATURE:
<223> OTHER INFORMATION: IgG1 with E345R/E430G mutation

<400> SEQUENCE: 65

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205
```

```
Lys Ala Leu Pro Ala Pro Ile Glu Lys Thr Ile Ser Lys Ala Lys Gly
    210                 215                 220

Gln Pro Arg Arg Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Gly Ala Leu His Asn His Tyr Thr
305                 310                 315                 320

Gln Lys Ser Leu Ser Leu Ser Pro Gly Lys
                325                 330


<210> SEQ ID NO 66
<211> LENGTH: 330
<212> TYPE: PRT
<213> ORGANISM: Artificial Sequence
<220> FEATURE:
<223> OTHER INFORMATION: IgG1 with E345R/E430G/S440Y mutation

<400> SEQUENCE: 66

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Arg Pro Gln Val Tyr Thr Leu Pro Pro Ser Arg Glu Glu
225                 230                 235                 240
```

```
Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Gly Ala Leu His Asn His Tyr Thr
305                 310                 315                 320

Gln Lys Tyr Leu Ser Leu Ser Pro Gly Lys
                325                 330


<210> SEQ ID NO 67
<211> LENGTH: 326
<212> TYPE: PRT
<213> ORGANISM: Artificial Sequence
<220> FEATURE:
<223> OTHER INFORMATION: IgG2sigma with E345R mutation

<400> SEQUENCE: 67

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Ala Ala Ala Ser Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser Ala Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Leu His Gln Asp Trp
            180                 185                 190

Leu Asn Gly Lys Glu Tyr Lys Cys Lys Val Ser Asn Lys Gly Leu Pro
        195                 200                 205

Ser Ser Ile Glu Lys Thr Ile Ser Lys Thr Lys Gly Gln Pro Arg Arg
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270
```

-continued

```
Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325
```

FC ENGINEERED ANTI-TNFR SUPERFAMILY MEMBER ANTIBODIES HAVING ENHANCED AGONISTIC ACTIVITY AND METHODS OF USING THEM

CROSS-REFERENCE TO RELATED APPLICATIONS

This application is a Continuation of U.S. application Ser. No. 15/668,895, filed 4 Aug. 2017, which claims the benefit of U.S. Provisional Application Ser. No. 62/374,347, filed 12 Aug. 2016. The entire contents of the aforementioned applications is incorporated herein by reference in their entireties.

SEQUENCE LISTING

This application contains a Sequence Listing submitted via EFS-Web, the entire content of which incorporated herein by reference in its entirety. The ASCII text file, created on 31 Jul. 2017, is named JBI5095USCNT1Seqlist.txt and is 168 kilobytes in size.

FIELD OF THE INVENTION

The present invention relates to engineered anti-TNFR superfamily member antibodies having enhanced agonistic activity and methods of using them.

BACKGROUND OF THE INVENTION

Monoclonal antibodies that stimulate antitumor immunity effects are emerging as an important class of cancer therapeutics. Many of them are directed against immunostimulatory tumor necrosis factor receptor (TNFR) superfamily members. Recent studies indicated that the agonistic and therapeutic activities of the anti-TNFR superfamily member antibodies depend on crosslinking to Fcγ receptors (FcγR) through the Fc (Li et al. (2011) *Science* 333: 1030-4; White et al. (2013) *Cancer Immunol Immunother* 62: 941-8). Fcγ receptors, particularly FcγRIIB, act as scaffolds to facilitate antibody multimerization that promotes receptor clustering, which is a prerequisite for activating downstream intracellular signaling (Bruhns et al. (2009) *Blood* 113: 3716-25).

An approach to further optimize the antitumor activity of anti-TNFR superfamily member antibodies has been to engineer the Fc region of the antibody to improve its FcγRIIB engagement. Substitutions S267E/L328F and E233D/G237D/P238D/H268D/P271G/A330R have been reported to selectively enhance FcγRIIB engagement (Chu et al. (2008) *Mol Immunol* 45: 3926-33; Mimoto et al. (2013) *Protein Eng Des Sel* 26: 589-98). Although optimizing FcγRIIB engagement is a viable approach, the agonistic activity of such engineered antibodies depends on the density of FcγR expressing cells in the local tumor microenvironment and therefore the efficacy of such antibody may be somewhat limited.

Therefore, there is a need for additional optimized anti-TNFR superfamily member antibodies.

BRIEF SUMMARY OF THE INVENTION

The invention provides for an isolated anti-tumor necrosis factor receptor (TNFR) superfamily member antibody, wherein the antibody comprises an E345R mutation, an E345R/E430G mutation or an E345R/E430G/S440Y mutation, residue numbering according to the EU Index, and has enhanced agonistic activity when compared to a parental antibody without the mutation.

The invention also provides for a pharmaceutical composition comprising the antibody of the invention and a pharmaceutically acceptable carrier.

The invention also provides for a method of enhancing an agonistic activity of an anti-TNFR superfamily member antibody in a subject, comprising introducing an E345R mutation, an E345R/E430G mutation or a E345R/E430G/S440Y mutation into the antibody to generate an engineered antibody specifically binding the TNFR superfamily member, and administering the engineered antibody to the subject.

The invention also provides for a method of treating a cancer in a subject, comprising administering to the subject an anti-TNFR superfamily member antibody comprising an E345R mutation, an E430G mutation, an E345R/E430G mutation or an E345R/E430G/S440Y for a time sufficient to treat the cancer.

The invention also provides an isolated anti-tumor necrosis factor receptor (TNFR) superfamily member antibody comprising an E345R mutation, an E345R/E430G mutation or an E345R/E430G/S440Y mutation, residue numbering according to the EU Index, and has enhanced agonistic activity when compared to a parental antibody without the mutation for use in the treatment of a cancer.

The invention also provides for a use of an isolated anti-tumor necrosis factor receptor (TNFR) superfamily member antibody comprising an E345R mutation, an E345R/E430G mutation or an E345R/E430G/S440Y mutation, residue numbering according to the EU Index, in the manufacture of a medicament for the treatment of cancer.

DETAILED DESCRIPTION OF THE INVENTION

Figure 1A:
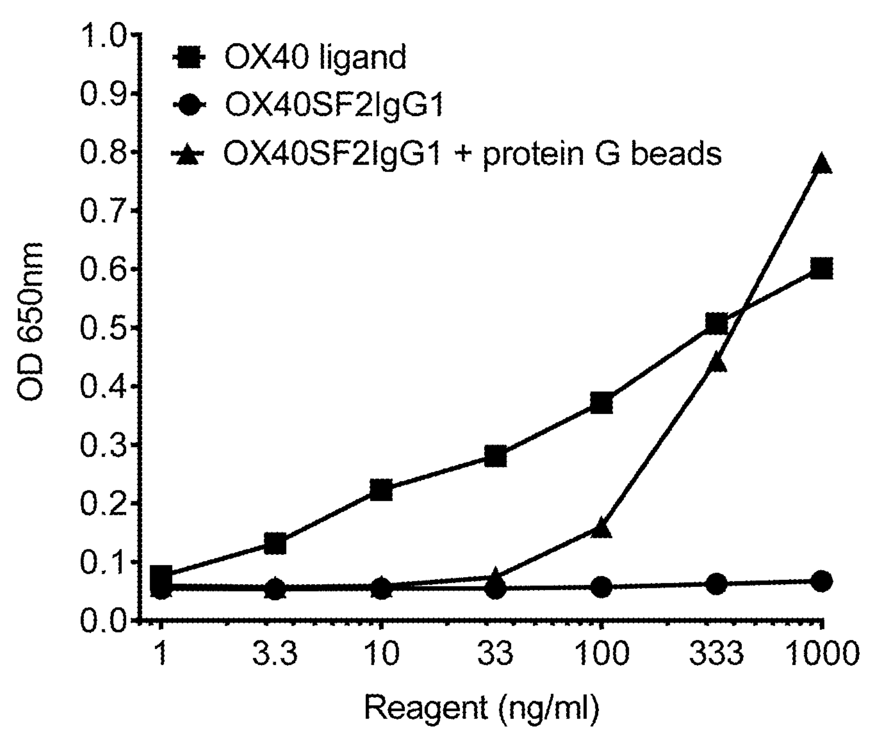
FIG. 1A shows that agonistic activity of anti-OX40 antibody is cross-linking dependent. OX40SF2IgG1 induced signaling only in the presence of cross-linker protein G beads in HEK-Blue™ NFκB reporter assay. Increasing concentrations (1 ng/ml to 1000 ng/ml) of OX40 ligand or OX40SF2IgG1 in the absence or presence of protein G beads were incubated with HEK-Blue™ cells stabely expressing OX40 and a secreted embryonic alkaline phosphatase (SEAP) reporter gene under the control of NFκB-inducible promoter. OD at 650 nm reflecting SEAP reporter gene expression were plotted vs. concentrations of test agents. Data are presented as mean±SEM, n=4.

All publications, including but not limited to patents and patent applications, cited in this specification are herein incorporated by reference as though fully set forth.

It is to be understood that the terminology used herein is for the purpose of describing particular embodiments only and is not intended to be limiting. Unless defined otherwise, all technical and scientific terms used herein have the same meaning as commonly understood by one of ordinary skill in the art to which the invention pertains.

Although any methods and materials similar or equivalent to those described herein may be used in the practice for testing of the present invention, exemplary materials and methods are described herein. In describing and claiming the present invention, the following terminology will be used.

As used in this specification and the appended claims, the singular forms "a," "an," and "the" include plural referents unless the content clearly dictates otherwise. Thus, for example, reference to "a cell" includes a combination of two or more cells, and the like.

"Anti-tumor necrosis factor receptor (TNFR) superfamily member antibody" or "anti-TNFR superfamily member antibody" refers to an antibody that specifically binds a TNFR superfamily member.

"TNFR superfamily member" includes receptors that belong to the TNFR superfamily, including the receptors shown in Table 1, including naturally occurring variants of the TNFRs. The TNFRs are typically expressed as type I transmembrane proteins and contain one to six cysteine-rich domains in their extracellular domain. Signaling occurs as a TNFR trimer. An amino acid sequence for one isoform for each TNFR is shown in Table 1. The ligand(s) of the TNFRs are also indicated in Table 1.

TABLE 1

| TNFR superfamily member | | Ligand(s) of the TNFR superfamily member | |
|---|---|---|---|
| Name | SEQ ID NO: | Name | SEQ ID NO: |
| Tumor necrosis factor receptor 1 (CD120a) | 1 | TNF-alpha (cachectin) | 28 |
| Tumor necrosis factor receptor 2 (CD120b) | 2 | TNF-alpha (cachectin) | 28 |
| Lymphotoxin beta receptor (CD18) | 3 | Lymphotoxin beta (TNF-C) | 29 |
| OX40 (CD134) | 4 | OX40L | 30 |
| CD40 | 5 | CD154 | 31 |
| Fas receptor (CD95) | 6 | FasL | 32 |

TABLE 1-continued

| TNFR superfamily member | | Ligand(s) of the TNFR superfamily member | |
|---|---|---|---|
| Name | SEQ ID NO: | Name | SEQ ID NO: |
| Decoy receptor 3 (TR6) | 7 | FasL, LIGHT, TL1A | 32 (FASL), 33(LIGHT), 34(TL1A) |
| CD27 | 8 | CD70, Siva | 35 (CD70), 36 (Siva) |
| CD30 | 9 | CD153 | 37 |
| 4-1BB (CD137) | 10 | 4-IBB ligand | 38 |
| Death receptor 4 (TRAILR1) | 11 | TRAIL | 39 |
| Death receptor 5 (TRAILR2) | 12 | TRAIL | 39 |
| Decoy receptor 1 (TRAILR3) | 13 | TRAIL | 39 |
| Decoy receptor 2 (TRAILR4) | 14 | TRAIL | 39 |
| RANK (CD265) | 15 | RANKL | 40 |
| Osteoprotegerin | 16 | RANKL | 40 |
| TWEAK receptor | 17 | TWEAK | 41 |
| TACI (CD267) | 18 | APRIL, BAFF, CAMLG | 42 (APRIL, 43 (BAFF), 44 (CAMLG) |
| BAFF receptor (CD268) | 19 | BAFF | 43 |
| Herpesvirus entry mediator (CD270) | 20 | LIGHT | 33 |
| Nerve growth factor receptor (CD271) | 21 | NGF, BDNF, NT-3, NT-4 | 45 (NGF), 46 (BDNF), 47 (NT-3), 48 (NT-4) |
| B-cell maturation antigen (CD269) | 22 | BAFF | 43 |
| Glucocorticoid-induced TNFR-related (CD357) | 23 | GITR ligand | 49 |
| TROY (TRADE) | 24 | unknown | |
| Death receptor 6 (CD358) | 25 | unknown | |
| Death receptor 3 (Apo-3) | 26 | TL1A | 34 |
| Ectodysplasin A2 receptor (XEDAR) | 27 | EDA-A2 | 50 |

"Specific binding" or "specifically binds" or "binds" refers to an anti-TNFR superfamily member antibody binding to a particular TNFR superfamily member or an epitope within the particular TNFR superfamily member with greater affinity than for other antigens. Typically, the antibody "specifically binds" when the equilibrium dissociation constant ($K_D$) for binding is about $1\times10^{-8}$ M or less, for example about $1\times10^{-9}$ M or less, about $1\times10^{-10}$ M or less, about $1\times10^{-11}$ M or less, or about $1\times10^{-12}$ M or less, typically with the $K_D$ that is at least one hundred-fold less than its $K_D$ for binding to a non-specific antigen (e.g., BSA, casein). The dissociation constant may be measured using standard procedures. Anti-TNFR superfamily member antibodies that specifically bind to the particular TNFR superfamily member or an epitope within the particular TNFR superfamily member may, however, have cross-reactivity to other related antigens, for example to the same antigen from other species (homologs), such as human or monkey, for example *Macaca fascicularis* (cynomolgus, cyno), *Pan troglodytes* (chimpanzee, chimp) or *Callithrix jacchus* (common marmoset, marmoset). While a monospecific antibody specifically binds one antigen or one epitope, a bispecific antibody specifically binds two distinct antigens or two distinct epitopes.

"Antibodies" is meant in a broad sense and includes immunoglobulin molecules including monoclonal antibodies including murine, human, humanized and chimeric monoclonal antibodies, antibody fragments, bispecific or multispecific antibodies, dimeric, tetrameric or multimeric antibodies, single chain antibodies, domain antibodies and any other modified configuration of the immunoglobulin molecule that comprises an antigen binding site of the required specificity. "Full-length antibody molecules" are comprised of two heavy chains (HC) and two light chains (LC) inter-connected by disulfide bonds as well as multimers thereof (e.g. IgM). Each heavy chain is comprised of a heavy chain variable region (VH) and a heavy chain constant region (comprised of domains CH1, hinge, CH2 and CH3). Each light chain is comprised of a light chain variable region (VL) and a light chain constant region (CL). The VH and the VL regions may be further subdivided into regions of hypervariability, termed complementarity determining regions (CDR), interspersed with framework regions (FR). Each VH and VL is composed of three CDRs and four FR segments, arranged from amino-to-carboxy-terminus in the following order: FR1, CDR1, FR2, CDR2, FR3, CDR3 and FR4.

"Complementarity determining regions (CDR)" are "antigen binding sites" in an antibody. CDRs may be defined using various terms: (i) Complementarity Determining Regions (CDRs), three in the VH (HCDR1, HCDR2, HCDR3) and three in the VL (LCDR1, LCDR2, LCDR3) are based on sequence variability (Wu et al. (1970) *J Exp Med* 132: 211-50; Kabat et al., Sequences of Proteins of Immunological Interest, 5th Ed. Public Health Service, National Institutes of Health, Bethesda, Md., 1991). (ii) "Hypervariable regions", "HVR", or "HV", three in the VH (H1, H2, H3) and three in the VL (L1, L2, L3) refer to the regions of an antibody variable domains which are hypervariable in structure as defined by Chothia and Lesk (Chothia et al. (1987) *J Mol Biol* 196: 901-17). The International ImMunoGeneTics (IMGT) database (http://www_imgt_org) provides a standardized numbering and definition of antigen-binding sites. The correspondence between CDRs, HVs and IMGT delineations is described in (Lefranc et al. (2003) *Dev Comp Immunol* 27: 55-77. The term "CDR", "HCDR1", "HCDR2", "HCDR3", "LCDR1", "LCDR2" and "LCDR3" as used herein includes CDRs defined by any of the methods described supra, Kabat, Chothia or IMGT, unless otherwise explicitly stated in the specification.

Immunoglobulins may be assigned to five major classes, IgA, IgD, IgE, IgG and IgM, depending on the heavy chain constant domain amino acid sequence. IgA and IgG are further sub-classified as the isotypes IgA1, IgA2, IgG1, IgG2, IgG3 and IgG4. Antibody light chains of any vertebrate species may assigned to one of two clearly distinct types, namely kappa (κ) and lambda (λ), based on the amino acid sequences of their constant domains.

"Antibody fragments" refers to a portion of an immunoglobulin molecule that retains the heavy chain and/or the light chain antigen binding site, such as heavy chain complementarity determining regions (HCDR) 1, 2 and 3, light chain complementarity determining regions (LCDR) 1, 2 and 3, a heavy chain variable region (VH), or a light chain variable region (VL). Antibody fragments include well known Fab, F(ab')2, Fd and Fv fragments as well as domain antibodies (dAb) consisting of one VH domain. VH and VL domains may be linked together via a synthetic linker to form various types of single chain antibody designs where the VH/VL domains may pair intramolecularly, or intermolecularly in those cases when the VH and VL domains are expressed by separate single chain antibody constructs, to form a monovalent antigen binding site, such as single chain Fv (scFv) or diabody; described for example in Int. Patent Publ. Nos. WO1998/44001, WO1988/01649, WO1994/13804 and WO1992/01047.

"Monoclonal antibody" refers to an antibody population with single amino acid composition in each heavy and each light chain, except for possible well known alterations such as removal of C-terminal lysine from the antibody heavy chain or alterations due to post-translational modification(s) of amino acids, such as methionine oxidation or asparagine or glutamine deamidation. Monoclonal antibodies typically bind one antigenic epitope, except that bispecific monoclonal antibodies bind two distinct antigenic epitopes. Monoclonal antibodies may have heterogeneous glycosylation within the antibody population. Monoclonal antibody may be monospecific or multispecific, or monovalent, bivalent or multivalent. A bispecific antibody is included in the term monoclonal antibody.

"Isolated antibody" refers to an antibody or antibody fragment that is substantially free of other antibodies having different antigenic specificities (e.g., an isolated antibody specifically binding for example OX-40 is substantially free of antibodies that specifically bind antigens other than OX-40). "Isolated antibody" encompasses antibodies that are isolated to a higher purity, such as antibodies that are 80%, 81%, 82%, 83%, 84%, 85%, 86%, 87%, 88%, 89%, 90%, 91%, 92%, 93%, 94%, 95%, 96%, 97%, 98%, 99% or 100% pure.

"Humanized antibody" refers to an antibody in which the antigen binding sites are derived from non-human species and the variable region frameworks are derived from human immunoglobulin sequences. Humanized antibody may include substitutions in the framework so that the framework may not be an exact copy of expressed human immunoglobulin or human immunoglobulin germline gene sequences.

"Human antibody" refers to an antibody having heavy and light chain variable regions in which both the framework and the antigen binding site are derived from sequences of human origin and is optimized to have minimal immune response when administered to a human subject. If the antibody contains a constant region or a portion of the constant region, the constant region also is derived from sequences of human origin.

Human antibody comprises heavy or light chain variable regions that are "derived from" sequences of human origin if the variable regions of the antibody are obtained from a system that uses human germline immunoglobulin or rearranged immunoglobulin genes. Such exemplary systems are human immunoglobulin gene libraries displayed on phage, and transgenic non-human animals such as mice or rats carrying human immunoglobulin loci as described herein. "Human antibody" may contain amino acid differences when compared to the human germline immunoglobulin or rearranged immunoglobulin genes due to differences between the systems used to obtain the antibody and human immunoglobulin loci, introduction of somatic mutations or intentional introduction of substitutions into the framework or antigen binding site, or both. Typically, "human antibody" is at least about 80%, 81%, 82%, 83%, 84%, 85%, 86%, 87%, 88%, 89%, 90%, 91%, 92%, 93%, 94%, 95%, 96%, 97%, 98% or 99% identical in amino acid sequence to an amino acid sequence encoded by human germline immunoglobulin or rearranged immunoglobulin genes. In some cases, "human antibody" may contain consensus framework sequences derived from human framework sequence analyses, for example as described in (Knappik et al. (2000) *J Mol Biol* 296: 57-86), or synthetic HCDR3 incorporated into human immunoglobulin gene libraries displayed on phage, for example as described in (Shi et al. (2010) *J Mol Biol* 397: 385-96, and in Int. Patent Publ. No. WO2009/085462.

Human antibodies derived from human immunoglobulin sequences may be generated using systems such as phage display incorporating synthetic CDRs and/or synthetic frameworks, or may be subjected to in vitro mutagenesis to improve antibody properties, resulting in antibodies that are not expressed by the human antibody germline repertoire in vivo.

Antibodies in which antigen binding sites are derived from a non-human species are not included in the definition of "human antibody".

"Recombinant" refers to antibodies and other proteins that are prepared, expressed, created or isolated by recombinant means.

"Epitope" refers to a portion of an antigen to which an antibody specifically binds. Epitopes typically consist of chemically active (such as polar, non-polar or hydrophobic) surface groupings of moieties such as amino acids or polysaccharide side chains and may have specific three-dimensional structural characteristics, as well as specific charge characteristics. An epitope may be composed of contiguous and/or discontiguous amino acids that form a conformational spatial unit. For a discontiguous epitope, amino acids from differing portions of the linear sequence of the antigen come in close proximity in 3-dimensional space through the folding of the protein molecule. Antibody "epitope" depends on the methodology used to identify the epitope.

"Bispecific" refers to an antibody that specifically binds two distinct antigens or two distinct epitopes within the same antigen. The bispecific antibody may have cross-reactivity to other related antigens, for example to the same antigen from other species (homologs), such as human or monkey, for example *Macaca fascicularis* (cynomolgus, cyno), *Pan troglodytes* (chimpanzee, chimp) or *Callithrix jacchus* (common marmoset, marmoset), or may bind an epitope that is shared between two or more distinct antigens.

"Multispecific" refers to an antibody that specifically binds two or more distinct antigens or two or more distinct epitopes within the same antigen.

"Vector" refers to a polynucleotide capable of being duplicated within a biological system or that can be moved between such systems. Vector polynucleotides typically contain elements, such as origins of replication, polyadenylation signal or selection markers, that function to facilitate the duplication or maintenance of these polynucleotides in a biological system, such as a cell, virus, animal, plant, and reconstituted biological systems utilizing biological components capable of duplicating a vector. The vector polynucleotide may be DNA or RNA molecules or a hybrid of these, single stranded or double stranded.

"Expression vector" refers to a vector that can be utilized in a biological system or in a reconstituted biological system to direct the translation of a polypeptide encoded by a polynucleotide sequence present in the expression vector.

"Polynucleotide" refers to a synthetic molecule comprising a chain of nucleotides covalently linked by a sugar-phosphate backbone or other equivalent covalent chemistry. cDNA is a typical example of a synthetic polynucleotide.

"Polypeptide" or "protein" refers to a molecule that comprises at least two amino acid residues linked by a peptide bond to form a polypeptide Small polypeptides of less than 50 amino acids may be referred to as "peptides".

A "cancer cell" or a "tumor cell" as used herein refers to a cancerous, pre-cancerous or transformed cell, either in vivo, ex vivo, or in tissue culture, that has spontaneous or induced phenotypic changes. These changes do not necessarily involve the uptake of new genetic material. Although transformation may arise from infection with a transforming virus and incorporation of new genomic nucleic acid, uptake of exogenous nucleic acid or it can also arise spontaneously or following exposure to a carcinogen, thereby mutating an endogenous gene. Transformation/cancer is exemplified by morphological changes, immortalization of cells, aberrant growth control, foci formation, proliferation, malignancy, modulation of tumor specific marker levels, invasiveness, tumor growth in suitable animal hosts such as nude mice, and the like, in vitro, in vivo, and ex vivo (Freshney, Culture of Animal Cells: A Manual of Basic Technique (3rd ed. 1994)).

"About" means within an acceptable error range for the particular value as determined by one of ordinary skill in the art, which will depend in part on how the value is measured or determined, i.e., the limitations of the measurement system. Unless explicitly stated otherwise within the Examples or elsewhere in the Specification in the context of a particular assay, result or embodiment, "about" means within one standard deviation per the practice in the art, or a range of up to 5%, whichever is larger.

"Valent" refers to the presence of a specified number of binding sites specific for an antigen in a molecule. As such, the terms "monovalent", "bivalent", "tetravalent", and "hexavalent" refer to the presence of one, two, four and six binding sites, respectively, specific for an antigen in a molecule.

"Agonist" refers to an antibody that induces at least one biological activity of the TNFR superfamily member the antibody binds to that is induced by a natural ligand of the TNFR superfamily member. Exemplary agonistic activities include induction of production of a secreted embryonic alkaline phosphatase (SEAP) expressed under the control of NFκB-inducible promoter in an in vitro assay, induction of dendritic cell (DC) differentiation assessed by increased CD80, CD83, CD86 and HLA-DR surface expression on DC, activation of B cells assessed by increased B cell proliferation or increased CD23, CD80, CD83, CD86 and HLA-DR surface expression on B cells, induction of antigen-specific T cell recall responses assessed by production of interferon-γ (IFN-γ) by PBMCs isolated from patients previously exposed to the antigen, and induction of $CD4^+$ or $CD8^+$ T cell proliferation. Agonistic activity (e.g., agonism) may be cross-linking dependent or independent of antibody cross-linking.

"Enhanced agonistic activity" or "enhanced agonism" refers to improvement in agonism of an engineered anti-TNFR superfamily member antibody when compared to the parental wild-type antibody, when agonistic activity is measured by anti-TNFR superfamily member antibody-induced production of secreted embryonic alkaline phosphatase (SEAP) expressed under the control of NFκB-inducible promoter. The engineered antibody has "enhanced agonistic activity" when it induces SEAP production at a level that is at least 20% higher when compared to the wild-type parental antibody at antibody concentration of 1 μg/mL in either cross-linking dependent or cross-linking independent manner.

"Cross-linking" refers to the higher order multimerization of an anti-TNFR superfamily member antibody on cells expressing the TNFR superfamily member, induced by the antibody binding to FcγR, for example FcγRIIb cis or trans, resulting in antibody-induced multimerization of TNFR and induction of TNFR agonistic activity. Cross-linking may be evaluated in vitro by using anti-human F(ab')2 as a cross-linker, or cells expressing FcγRIIb, such as Raji cells as described herein.

"Agonistic activity independent of antibody cross-linking" means that the antibody induces production of SEAP in a HEK-Blue™ reporter assay as described in Example 3 herein in solution in the absence of Raji cells expressing FcγR, for example FcγRIIB.

"Subject" includes any human or nonhuman animal. "Nonhuman animal" includes all vertebrates, e.g., mammals and non-mammals, such as nonhuman primates, sheep, dogs, cats, horses, cows chickens, amphibians, reptiles, etc.

The numbering of amino acid residues in the antibody constant region throughout the specification is according to the EU index as described in Kabat et al., Sequences of Proteins of Immunological Interest, 5th Ed. Public Health Service, National Institutes of Health, Bethesda, Md. (1991), unless otherwise explicitly stated.

Conventional one and three-letter amino acid codes are used herein as shown in Table 2.

TABLE 2

| Amino acid | Three-letter code | One-letter code |
|---|---|---|
| Alanine | Ala | A |
| Arginine | Arg | R |
| Asparagine | Asn | N |
| Aspartate | Asp | D |
| Cysteine | Cys | C |
| Glutamate | Gln | E |
| Glutamine | Glu | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Compositions of Matter

The present invention provides engineered anti-TNFR superfamily member antibodies having improved properties displaying enhanced agonistic activity coupled with isotype-dependent modulation of antibody effector functions. The invention is based, at least in part, on the finding that substitutions that multimerize anti-TNFR superfamily member antibodies on the surface cells enhance agonistic activity of the antibodies independent of cross-linking.

The invention provides for an isolated anti-tumor necrosis factor receptor (TNFR) superfamily member antibody, wherein the antibody comprises an E345R mutation, optionally further comprising an E430G mutation, a S440Y mutation, or an E430G/S440Y mutation, residue numbering according to the EU Index, and has enhanced agonistic activity when compared to a parental antibody without the mutation.

The invention also provides for an isolated anti-tumor necrosis factor receptor (TNFR) superfamily member antibody, wherein the antibody comprises an E345R mutation, an E345R/E430G mutation or a E345R/E430G/S440Y mutation, residue numbering according to the EU Index, and has enhanced agonistic activity when compared to a parental antibody without the mutation.

The E345R substitution was shown herein to enhance agonistic activity of an anti-TNFR superfamily member antibody.

The E430G substitution was shown herein to enhance agonistic activity of an anti-TNFR superfamily member antibody.

The E345R/E430G substitution was shown herein to enhance agonistic activity of an anti-TNFR superfamily member antibody.

The E345R/E430G/S440Y substitution was shown herein to enhance agonistic activity of an anti-TNFR superfamily member antibody.

The invention also provides for an isolated anti-TNFR superfamily member antibody, wherein the antibody comprises an E345R mutation, residue numbering according to the EU Index, and has enhanced agonistic activity when compared to the parental antibody without the E345R mutation.

The invention also provides for an isolated anti-TNFR superfamily member antibody, wherein the antibody comprises an E430G mutation, residue numbering according to the EU Index, and has enhanced agonistic activity when compared to the parental antibody without the E430G mutation.

The invention also provides for an isolated anti-TNFR superfamily member antibody, wherein the antibody comprises an E345R/E430G mutation, residue numbering according to the EU Index, and has enhanced agonistic activity when compared to the parental antibody without the E345R/E430G mutation.

The invention also provides for an isolated anti-TNFR superfamily member antibody, wherein the antibody comprises an E345R/E430G/S440Y mutation, residue numbering according to the EU Index, and has enhanced agonistic activity when compared to the parental antibody without the E345R/E430G/S440Y mutation.

In some embodiments, the anti-TNFR superfamily member antibody of the invention has agonistic activity independent of FcγR antibody cross-linking. Therefore, the antibodies of the invention having agonistic activity independent of FcγR cross-linking are not dependent on the bioavailability and density of cells expressing FcγR in the tumor microenvironment for their agonistic activity and can induce TNFR signaling in environments lacking sufficient FcγR cell infiltration.

The anti-TNFR superfamily member antibodies of the invention may demonstrate level of agonism less than that of the native ligand, and therefore may provide an improved safety profile.

"Parental antibody" refers to the anti-TNFR superfamily member antibody used to produce the engineered antibody of the invention.

In some embodiments, the antibody comprises the E345R mutation.

In some embodiments, the antibody mediates antibody-dependent cellular cytotoxicity (ADCC).

In some embodiments, the antibody mediates antibody-dependent cell phagocytosis (ADCP).

In some embodiments, the antibody mediates CDC.

In some embodiments, the antibody of the invention comprising the E345R mutation may further comprise a second mutation which reduces or abolishes antibody Fc mediated effector functions. The antibodies of the present invention comprising the E435R mutation and a second mutation that reduces or abolishes antibody Fc mediated effector functions may therefore be used in instances in which depletion of the TNFR expressing cells is not desirable. Exemplary such instances are therapeutic treatments with anti-CD40 or anti-CD27 antibodies.

In some embodiments, the antibody comprises the E345R mutation and is an IgG1 isotype, optionally further comprising a L234A/L235A mutation when compared to the wild-type IgG1.

In some embodiments, the antibody comprises the E345R mutation and is an IgG1 isotype, optionally further comprising a L234F/L235E/D265A mutation when compared to the wild-type IgG1.

In some embodiments, the antibody comprises the E345R mutation and is an IgG1 isotype, optionally further comprising a K214T/E233P/L234V/L235A/G236-deleted/A327G/P331A/D365E/L358M mutation when compared to the wild-type IgG1.

In some embodiments, the antibody comprises the E345R mutation and an of IgG1 isotype, optionally further comprising a L234A/L235A/G237A/P238S/H268A/A330S/P331S mutation when compared to the wild-type IgG1.

In some embodiments, the antibody comprises the E345R mutation and is an IgG1 isotype and further comprises a L234A/L235A/G237A/P238S/H268A/A330S/P331S mutation when compared to the wild-type IgG1.

In some embodiments, the antibody comprises the E345R mutation and is an IgG2 isotype, optionally further comprising a V234A/G237A/P238S/H268A/V309L/A330S/P331S mutation when compared to the wild-type IgG2.

In some embodiments, the antibody comprises the E345R mutation and is an IgG2 isotype and further comprises a V234A/G237A/P238S/H268A/V309L/A330S/P331S mutation when compared to the wild-type IgG2.

In some embodiments, the antibody comprises the E345R mutation and is an IgG2 isotype, optionally further comprising a V234A/G237A mutation when compared to the wild-type IgG2.

In some embodiments, the antibody comprises the E345R mutation and is an IgG2 isotype, optionally further comprising a H268Q/V309L/A330S/P331S mutation when compared to the wild-type IgG2.

In some embodiments, the antibody comprises the E345R mutation and is an IgG3 isotype.

In some embodiments, the antibody comprises the E345R mutation and is an IgG4 isotype, optionally further comprising a F234A/L235A mutation when compared to the wild-type IgG4.

In some embodiments, the antibody comprises the E345R mutation and is an IgG4 isotype, optionally further comprising a S228P/F234A/L235A/G237A/P238S mutation when compared to the wild-type IgG4.

In some embodiments, the antibody comprises the E345R mutation and is an IgG4 isotype, optionally further comprising a S228P/F234A/L235A/G236-deleted/G237A/P238S mutation when compared to the wild-type IgG4

In some embodiments, the antibody comprises the E345R mutation and is an IgG4 isotype, optionally further comprising a S228P/F234A/L235A mutation when compared to the wild-type IgG4.

In some embodiments, the antibody comprises the E345R mutation and is an IgG4 isotype and comprises the S228P/F234A/L235A mutation when compared to the wild-type IgG4.

In some embodiments, the antibody comprises the E345R mutation and has agonistic activity independent of antibody cross-linking, wherein agonistic activity is measured by measuring antibody-induced production of secreted embryonic alkaline phosphatase (SEAP) expressed under the control of NFκB-inducible promoter from Hek-293 cells.

In some embodiments, the antibody comprises the E345R mutation and binds TNFR superfamily member tumor necrosis factor receptor 1 (SEQ ID NO: 1), tumor necrosis factor receptor 2 (SEQ ID NO: 2), lymphotoxin beta receptor (SEQ ID NO: 3), OX40 (SEQ ID NO: 4), CD40 (SEQ ID NO: 5), Fas receptor (SEQ ID NO: 6), decoy receptor 3 (SEQ ID NO: 7), CD27 (SEQ ID NO: 8), CD30 (SEQ ID NO: 9), CD137 (SEQ ID NO: 10), death receptor 4 (SEQ ID NO: 11), death receptor 5 (SEQ ID NO: 12), decoy receptor 1 (SEQ ID NO: 13), decoy receptor 2 (SEQ ID NO: 14), RANK (SEQ ID NO: 15), osteoprotegerin (SEQ ID NO: 16), TWEAK receptor (SEQ ID NO: 17), TACI (SEQ ID NO: 18), BAFF receptor (SEQ ID NO: 19), herpesvirus entry mediator (SEQ ID NO: 20), nerve growth factor receptor (SEQ ID NO: 21), B-cell maturation antigen (SEQ ID NO: 22), GITR (SEQ ID NO: 23), TROY (SEQ ID NO: 24), death receptor 6 (SEQ ID NO: 25), death receptor 3 (SEQ ID NO: 26) or ectodysplasin A2 receptor (SEQ ID NO: 27).

In some embodiments, the antibody comprises the E345R mutation and binds TNFR superfamily member OX40 (SEQ ID NO: 4), CD27 (SEQ ID NO: 8), CD40 (SEQ ID NO: 5), CD137 (SEQ ID NO: 10), or GITR (SEQ ID NO: 23).

In some embodiments, the antibody comprises the E345R mutation and binds TNFR superfamily member OX40 (SEQ ID NO: 4).

In some embodiments, the antibody comprises the E345R mutation and binds TNFR superfamily member CD27 (SEQ ID NO: 8).

In some embodiments, the antibody comprises the E345R mutation and binds TNFR superfamily member CD40 (SEQ ID NO: 5).

In some embodiments, the antibody comprises the E345R mutation and binds TNFR superfamily member CD137 (SEQ ID NO: 10).

In some embodiments, the antibody comprises the E345R mutation and binds TNFR superfamily member GITR (SEQ ID NO: 23).

The antibody comprising the E345R mutation is suitable for use in therapy, for example in treating cancer.

The antibody comprising the E345R mutation is suitable for use in therapy, for example in treating a solid tumor.

The antibody comprising the E345R mutation is suitable for use in therapy, for example in treating a melanoma.

The antibody comprising the E345R mutation is suitable for use in therapy, for example in treating a lung cancer.

The antibody comprising the E345R mutation is suitable for use in therapy, for example in treating a squamous non-small cell lung cancer (NSCLC).

The antibody comprising the E345R mutation is suitable for use in therapy, for example in treating a non-squamous NSCLC.

The antibody comprising the E345R mutation is suitable for use in therapy, for example in treating a lung adenocarcinoma.

The antibody comprising the E345R mutation is suitable for use in therapy, for example in treating a renal cell carcinoma (RCC) (e.g., a kidney clear cell carcinoma or a kidney papillary cell carcinoma), or a metastatic lesion thereof.

The antibody comprising the E345R mutation is suitable for use in therapy, for example in treating a mesothelioma.

The antibody comprising the E345R mutation is suitable for use in therapy, for example in treating a nasopharyngeal carcinoma (NPC).

The antibody comprising the E345R mutation is suitable for use in therapy, for example in treating a colorectal cancer.

The antibody comprising the E345R mutation is suitable for use in therapy, for example in treating a prostate cancer or castration-resistant prostate cancer.

The antibody comprising the E345R mutation is suitable for use in therapy, for example in treating a stomach cancer.

The antibody comprising the E345R mutation is suitable for use in therapy, for example in treating an ovarian cancer.

The antibody comprising the E345R mutation is suitable for use in therapy, for example in treating a gastric cancer.

The antibody comprising the E345R mutation is suitable for use in therapy, for example in treating a liver cancer.

The antibody comprising the E345R mutation is suitable for use in therapy, for example in treating pancreatic cancer.

The antibody comprising the E345R mutation is suitable for use in therapy, for example in treating a thyroid cancer.

The antibody comprising the E345R mutation is suitable for use in therapy, for example in treating a squamous cell carcinoma of the head and neck.

The antibody comprising the E345R mutation is suitable for use in therapy, for example in treating a carcinomas of the esophagus or gastrointestinal tract.

The antibody comprising the E345R mutation is suitable for use in therapy, for example in treating a breast cancer.

The antibody comprising the E345R mutation is suitable for use in therapy, for example in treating a fallopian tube cancer.

The antibody comprising the E345R mutation is suitable for use in therapy, for example in treating a brain cancer.

The antibody comprising the E345R mutation is suitable for use in therapy, for example in treating an urethral cancer.

The antibody comprising the E345R mutation is suitable for use in therapy, for example in treating a genitourinary cancer.

The antibody comprising the E345R mutation is suitable for use in therapy, for example in treating an endometriosis.

The antibody comprising the E345R mutation is suitable for use in therapy, for example in treating a cervical cancer.

The antibody comprising the E345R mutation is suitable for use in therapy, for example in treating a metastatic lesion of the cancer.

In some embodiments, the antibody comprises the E430G mutation.

In some embodiments, the antibody mediates antibody-dependent cellular cytotoxicity (ADCC).

In some embodiments, the antibody mediates antibody-dependent cell phagocytosis (ADCP).

In some embodiments, the antibody mediates CDC.

In some embodiments, the antibody of the invention comprising the E430G mutation may further comprise a second mutation which reduces or abolishes antibody Fc mediated effector functions. The antibodies of the present invention comprising the E430G mutation and a second mutation that reduces or abolishes antibody Fc mediated effector functions may therefore be used in instances in which depletion of the TNFR expressing cells is not desirable. Exemplary such instances are therapeutic treatments with anti-CD40 or anti-CD27 antibodies.

In some embodiments, the antibody comprises the E430G mutation and is an IgG1 isotype, optionally further comprising a L234A/L235A mutation when compared to the wild-type IgG1.

In some embodiments, the antibody comprises the E430G mutation and is an IgG1 isotype, optionally further comprising a L234F/L235E/D265A mutation when compared to the wild-type IgG1.

In some embodiments, the antibody comprises the E430G mutation and is an IgG1 isotype, optionally further comprising a K214T/E233P/L234V/L235A/G236-deleted/A327G/P331A/D365E/L358M mutation when compared to the wild-type IgG1.

In some embodiments, the antibody comprises the E430G mutation and is an IgG1 isotype, optionally further comprising a L234A/L235A/G237A/P238S/H268A/A330S/P331S mutation when compared to the wild-type IgG1.

In some embodiments, the antibody comprises the E430G mutation and is an IgG1 isotype and further comprises a L234A/L235A/G237A/P238S/H268A/A330S/P331S mutation when compared to the wild-type IgG1.

In some embodiments, the antibody comprises the E430G mutation and is an IgG2 isotype, optionally further comprising a V234A/G237A/P238S/H268A/V309L/A330S/P331S mutation when compared to the wild-type IgG2.

In some embodiments, the antibody comprises the E430G mutation and is an IgG2 isotype and further comprises a V234A/G237A/P238S/H268A/V309L/A330S/P331S mutation when compared to the wild-type IgG2.

In some embodiments, the antibody comprises the E430G mutation and is of IgG2 isotype, optionally further comprising a V234A/G237A mutation when compared to the wild-type IgG2.

In some embodiments, the antibody comprises the E430G mutation and is an IgG2 isotype, optionally further comprising a H268Q/V309L/A330S/P331S mutation when compared to the wild-type IgG2.

In some embodiments, the antibody comprises the E430G mutation and is an IgG3 isotype.

In some embodiments, the antibody comprises the E430G mutation and is an IgG4 isotype, optionally further comprising a F234A/L235A mutation when compared to the wild-type IgG4.

In some embodiments, the antibody comprises the E430G mutation and is an IgG4 isotype, optionally further comprising a S228P/F234A/L235A/G237A/P238S mutation when compared to the wild-type IgG4.

In some embodiments, the antibody comprises the E430G mutation and is an IgG4 isotype, optionally further comprising a S228P/F234A/L235A/G236-deleted/G237A/P238S mutation when compared to the wild-type IgG4

In some embodiments, the antibody comprises the E430G mutation and is an IgG4 isotype, optionally further comprising a S228P/F234A/L235A mutation when compared to the wild-type IgG4.

In some embodiments, the antibody comprises the E430G mutation and is an IgG4 isotype and comprises the S228P/F234A/L235A mutation when compared to the wild-type IgG4.

In some embodiments, the antibody comprises the E430G mutation and has agonistic activity independent of antibody cross-linking, wherein agonistic activity is measured by measuring antibody-induced production of secreted embryonic alkaline phosphatase (SEAP) expressed under the control of NFκB-inducible promoter from Hek-293 cells.

In some embodiments, the antibody comprises the E430G mutation and binds TNFR superfamily member tumor necrosis factor receptor 1 (SEQ ID NO: 1), tumor necrosis factor receptor 2 (SEQ ID NO: 2), lymphotoxin beta receptor (SEQ ID NO: 3), OX40 (SEQ ID NO: 4), CD40 (SEQ ID NO: 5), Fas receptor (SEQ ID NO: 6), decoy receptor 3 (SEQ ID NO: 7), CD27 (SEQ ID NO: 8), CD30 (SEQ ID NO: 9), CD137 (SEQ ID NO: 10), death receptor 4 (SEQ ID NO: 11), death receptor 5 (SEQ ID NO: 12), decoy receptor 1 (SEQ ID NO: 13), decoy receptor 2 (SEQ ID NO: 14), RANK (SEQ ID NO: 15), osteoprotegerin (SEQ ID NO: 16), TWEAK receptor (SEQ ID NO: 17), TACI (SEQ ID NO: 18), BAFF receptor (SEQ ID NO: 19), herpesvirus entry mediator (SEQ ID NO: 20), nerve growth factor receptor (SEQ ID NO: 21), B-cell maturation antigen (SEQ ID NO: 22), GITR (SEQ ID NO: 23), TROY (SEQ ID NO: 24), death receptor 6 (SEQ ID NO: 25), death receptor 3 (SEQ ID NO: 26) or ectodysplasin A2 receptor (SEQ ID NO: 27).

In some embodiments, the antibody comprises the E430G mutation and binds TNFR superfamily member OX40 (SEQ ID NO: 4), CD27 (SEQ ID NO: 8), CD40 (SEQ ID NO: 5), CD137 (SEQ ID NO: 10), or GITR (SEQ ID NO: 23).

In some embodiments, the antibody comprises the E430G mutation and binds TNFR superfamily member OX40 (SEQ ID NO: 4).

In some embodiments, the antibody comprises the E430G mutation and binds TNFR superfamily member CD27 (SEQ ID NO: 8).

In some embodiments, the antibody comprises the E430G mutation and binds TNFR superfamily member CD40 (SEQ ID NO: 5).

In some embodiments, the antibody comprises the E430G mutation and binds TNFR superfamily member CD137 (SEQ ID NO: 10).

In some embodiments, the antibody comprises the E430G mutation and binds TNFR superfamily member GITR (SEQ ID NO: 23).

The antibody comprising the E430G mutation is suitable for use in therapy, for example in treating cancer.

The antibody comprising the E430G mutation is suitable for use in therapy, for example in treating cancer.

The antibody comprising the E430G mutation is suitable for use in therapy, for example in treating a solid tumor.

The antibody comprising the E430G mutation is suitable for use in therapy, for example in treating a melanoma.

The antibody comprising the E430G mutation is suitable for use in therapy, for example in treating a lung cancer.

The antibody comprising the E430G mutation is suitable for use in therapy, for example in treating a squamous non-small cell lung cancer (NSCLC).

The antibody comprising the E430G mutation is suitable for use in therapy, for example in treating a non-squamous NSCLC.

The antibody comprising the E430G mutation is suitable for use in therapy, for example in treating a lung adenocarcinoma.

The antibody comprising the E430G mutation is suitable for use in therapy, for example in treating a renal cell carcinoma (RCC) (e.g., a kidney clear cell carcinoma or a kidney papillary cell carcinoma), or a metastatic lesion thereof.

The antibody comprising the E430G mutation is suitable for use in therapy, for example in treating a mesothelioma.

The antibody comprising the E430G mutation is suitable for use in therapy, for example in treating a nasopharyngeal carcinoma (NPC).

The antibody comprising the E430G mutation is suitable for use in therapy, for example in treating a colorectal cancer.

The antibody comprising the E430G mutation is suitable for use in therapy, for example in treating a prostate cancer or castration-resistant prostate cancer.

The antibody comprising the E430G mutation is suitable for use in therapy, for example in treating a stomach cancer.

The antibody comprising the E430G mutation is suitable for use in therapy, for example in treating an ovarian cancer.

The antibody comprising the E430G mutation is suitable for use in therapy, for example in treating a gastric cancer.

The antibody comprising the E430G mutation is suitable for use in therapy, for example in treating a liver cancer.

The antibody comprising the E430G mutation is suitable for use in therapy, for example in treating pancreatic cancer.

The antibody comprising the E430G mutation is suitable for use in therapy, for example in treating a thyroid cancer.

The antibody comprising the E430G mutation is suitable for use in therapy, for example in treating a squamous cell carcinoma of the head and neck.

The antibody comprising the E430G mutation is suitable for use in therapy, for example in treating a carcinomas of the esophagus or gastrointestinal tract.

The antibody comprising the E430G mutation is suitable for use in therapy, for example in treating a breast cancer.

The antibody comprising the E430G mutation is suitable for use in therapy, for example in treating a fallopian tube cancer.

The antibody comprising the E430G mutation is suitable for use in therapy, for example in treating a brain cancer.

The antibody comprising the E430G mutation is suitable for use in therapy, for example in treating an urethral cancer.

The antibody comprising the E430G mutation is suitable for use in therapy, for example in treating a genitourinary cancer.

The antibody comprising the E430G mutation is suitable for use in therapy, for example in treating an endometriosis.

The antibody comprising the E430G mutation is suitable for use in therapy, for example in treating a cervical cancer.

The antibody comprising the E430G mutation is suitable for use in therapy, for example in treating a metastatic lesion of the cancer.

In some embodiments, the antibody comprises the E345R/E430G mutation.

In some embodiments, the antibody mediates antibody-dependent cellular cytotoxicity (ADCC).

In some embodiments, the antibody mediates antibody-dependent cell phagocytosis (ADCP).

In some embodiments, the antibody mediates CDC.

In some embodiments, the antibody of the invention comprising the E345R/E430G mutation may further comprise a second mutation which reduces or abolishes antibody Fc mediated effector functions. The antibodies of the present invention comprising the E345R/E430G mutation and a second mutation that reduces or abolishes antibody Fc mediated effector functions may therefore be used in instances in which depletion of the TNFR expressing cells is not desirable. Exemplary such instances are therapeutic treatments with anti-CD40 or anti-CD27 antibodies.

In some embodiments, the antibody comprises the E345R/E430G mutation and is an IgG1 isotype, optionally further comprising a L234A/L235A mutation when compared to the wild-type IgG1.

In some embodiments, the antibody comprises the E345R/E430G mutation and is an IgG1 isotype, optionally further comprising a L234F/L235E/D265A mutation when compared to the wild-type IgG1.

In some embodiments, the antibody comprises the E345R/E430G mutation and is an IgG1 isotype, optionally further comprising a K214T/E233P/L234V/L235A/G236-deleted/A327G/P331A/D365E/L358M mutation when compared to the wild-type IgG1.

In some embodiments, the antibody comprises the E345R/E430G mutation and is an IgG1 isotype, optionally further comprising a L234A/L235A/G237A/P238S/H268A/A330S/P331S mutation when compared to the wild-type IgG1.

In some embodiments, the antibody comprises the E345R/E430G mutation and is an IgG1 isotype and further comprises a L234A/L235A/G237A/P238S/H268A/A330S/P331S mutation when compared to the wild-type IgG1.

In some embodiments, the antibody comprises the E345R/E430G mutation and is an IgG2 isotype, optionally further comprising a V234A/G237A/P238S/H268A/V309L/A330S/P331S mutation when compared to the wild-type IgG2.

In some embodiments, the antibody comprises the E345R/E430G mutation and is an IgG2 isotype and further comprises a V234A/G237A/P238S/H268A/V309L/A330S/P331S mutation when compared to the wild-type IgG2.

In some embodiments, the antibody comprises the E345R/E430G mutation and is an IgG2 isotype, optionally further comprising a V234A/G237A mutation when compared to the wild-type IgG2.

In some embodiments, the antibody comprises the E345R/E430G mutation and is an IgG2 isotype, optionally further comprising a H268Q/V309L/A330S/P331S mutation when compared to the wild-type IgG2.

In some embodiments, the antibody comprises the E345R/E430G mutation and is an IgG3 isotype.

In some embodiments, the antibody comprises the E345R/E430G mutation and is an IgG4 isotype, optionally further comprising a F234A/L235A mutation when compared to the wild-type IgG4.

In some embodiments, the antibody comprises the E345R/E430G mutation and is an IgG4 isotype, optionally further comprising a S228P/F234A/L235A/G237A/P238S mutation when compared to the wild-type IgG4.

In some embodiments, the antibody comprises the E345R/E430G mutation and is an IgG4 isotype, optionally further comprising a S228P/F234A/L235A/G236-deleted/G237A/P238S mutation when compared to the wild-type IgG4

In some embodiments, the antibody comprises the E345R/E430G mutation and is an IgG4 isotype, optionally further comprising a S228P/F234A/L235A mutation when compared to the wild-type IgG4.

In some embodiments, the antibody comprises the E345R/E430G mutation and is an IgG4 isotype and comprises the S228P/F234A/L235A mutation when compared to the wild-type IgG4.

In some embodiments, the antibody comprises the E345R/E430G mutation and has agonistic activity independent of antibody cross-linking, wherein agonistic activity is measured by measuring antibody-induced production of secreted embryonic alkaline phosphatase (SEAP) expressed under the control of NFκB-inducible promoter from Hek-293 cells.

In some embodiments, the antibody comprises the E345R/E430G mutation and binds TNFR superfamily member tumor necrosis factor receptor 1 (SEQ ID NO: 1), Tumor necrosis factor receptor 2 (SEQ ID NO: 2), lymphotoxin beta receptor (SEQ ID NO: 3), OX40 (SEQ ID NO: 4), CD40 (SEQ ID NO: 5), Fas receptor (SEQ ID NO: 6), decoy receptor 3 (SEQ ID NO: 7), CD27 (SEQ ID NO: 8), CD30 (SEQ ID NO: 9), CD137 (SEQ ID NO: 10), death receptor 4 (SEQ ID NO: 11), death receptor 5 (SEQ ID NO: 12), decoy receptor 1 (SEQ ID NO: 13), decoy receptor 2 (SEQ ID NO: 14), RANK (SEQ ID NO: 15), osteoprotegerin (SEQ ID NO: 16), TWEAK receptor (SEQ ID NO: 17), TACI (SEQ ID NO: 18), BAFF receptor (SEQ ID NO: 19), herpesvirus entry mediator (SEQ ID NO: 20), nerve growth factor receptor (SEQ ID NO: 21), B-cell maturation antigen (SEQ ID NO: 22), GITR (SEQ ID NO: 23), TROY (SEQ ID NO: 24), death receptor 6 (SEQ ID NO: 25), death receptor 3 (SEQ ID NO: 26) or ectodysplasin A2 receptor (SEQ ID NO: 27).

In some embodiments, the antibody comprises the E345R/E430G mutation and binds TNFR superfamily member OX40 (SEQ ID NO: 4), CD27 (SEQ ID NO: 8), CD40 (SEQ ID NO: 5), CD137 (SEQ ID NO: 10), or GITR (SEQ ID NO: 23).

In some embodiments, the antibody comprises the E345R/E430G mutation and binds TNFR superfamily member OX40 (SEQ ID NO: 4).

In some embodiments, the antibody comprises the E345R/E430G mutation and binds TNFR superfamily member CD27 (SEQ ID NO: 8).

In some embodiments, the antibody comprises the E345R/E430G mutation and binds TNFR superfamily member CD40 (SEQ ID NO: 5).

In some embodiments, the antibody comprises the E345R/E430G mutation and binds TNFR superfamily member CD137 (SEQ ID NO: 10).

In some embodiments, the antibody comprises the E345R/E430G mutation and binds TNFR superfamily member GITR (SEQ ID NO: 23).

The antibody comprising the E345R/E430G mutation is suitable for use in therapy, for example in treating cancer.

The antibody comprising the E345R/E430G mutation is suitable for use in therapy, for example in treating cancer.

The antibody comprising the E345R/E430G mutation is suitable for use in therapy, for example in treating a solid tumor.

The antibody comprising the E345R/E430G mutation is suitable for use in therapy, for example in treating a melanoma.

The antibody comprising the E345R/E430G mutation is suitable for use in therapy, for example in treating a lung cancer.

The antibody comprising the E345R/E430G mutation is suitable for use in therapy, for example in treating a squamous non-small cell lung cancer (NSCLC).

The antibody comprising the E345R/E430G mutation is suitable for use in therapy, for example in treating a non-squamous NSCLC.

The antibody comprising the E345R/E430G mutation is suitable for use in therapy, for example in treating a lung adenocarcinoma.

The antibody comprising the E345R/E430G mutation is suitable for use in therapy, for example in treating a renal cell carcinoma (RCC) (e.g., a kidney clear cell carcinoma or a kidney papillary cell carcinoma), or a metastatic lesion thereof.

The antibody comprising the E345R/E430G mutation is suitable for use in therapy, for example in treating a mesothelioma.

The antibody comprising the E345R/E430G mutation is suitable for use in therapy, for example in treating a nasopharyngeal carcinoma (NPC).

The antibody comprising the E345R/E430G mutation is suitable for use in therapy, for example in treating a colorectal cancer.

The antibody comprising the E345R/E430G mutation is suitable for use in therapy, for example in treating a prostate cancer or castration-resistant prostate cancer.

The antibody comprising the E345R/E430G mutation is suitable for use in therapy, for example in treating a stomach cancer.

The antibody comprising the E345R/E430G mutation is suitable for use in therapy, for example in treating an ovarian cancer.

The antibody comprising the E345R/E430G mutation is suitable for use in therapy, for example in treating a gastric cancer.

The antibody comprising the E345R/E430G mutation is suitable for use in therapy, for example in treating a liver cancer.

The antibody comprising the E345R/E430G mutation is suitable for use in therapy, for example in treating pancreatic cancer.

The antibody comprising the E345R/E430G mutation is suitable for use in therapy, for example in treating a thyroid cancer.

The antibody comprising the E345R/E430G mutation is suitable for use in therapy, for example in treating a squamous cell carcinoma of the head and neck.

The antibody comprising the E345R/E430G mutation is suitable for use in therapy, for example in treating a carcinomas of the esophagus or gastrointestinal tract.

The antibody comprising the E345R/E430G mutation is suitable for use in therapy, for example in treating a breast cancer.

The antibody comprising the E345R/E430G mutation is suitable for use in therapy, for example in treating a fallopian tube cancer.

The antibody comprising the E345R/E430G mutation is suitable for use in therapy, for example in treating a brain cancer.

The antibody comprising the E345R/E430G mutation is suitable for use in therapy, for example in treating an urethral cancer.

The antibody comprising the E345R/E430G mutation is suitable for use in therapy, for example in treating a genitourinary cancer.

The antibody comprising the E345R/E430G mutation is suitable for use in therapy, for example in treating an endometriosis.

The antibody comprising the E345R/E430G mutation is suitable for use in therapy, for example in treating a cervical cancer.

The antibody comprising the E345R/E430G mutation is suitable for use in therapy, for example in treating a metastatic lesion of the cancer.

In some embodiments, the antibody comprises the E345R/E430G/S440Y mutation.

In some embodiments, the antibody mediates antibody-dependent cellular cytotoxicity (ADCC).

In some embodiments, the antibody mediates antibody-dependent cell phagocytosis (ADCP).

In some embodiments, the antibody mediates CDC.

In some embodiments, the antibody of the invention comprising the E345R/E430G/S440Y mutation may further comprise a second mutation which reduces or abolishes antibody Fc mediated effector functions. The antibodies of the present invention comprising the E345R/E430G/S440Y mutation and a second mutation that reduces or abolishes antibody Fc mediated effector functions may therefore be used in instances in which depletion of the TNFR expressing cells is not desirable. Exemplary such instances are therapeutic treatments with anti-CD40 or anti-CD27 antibodies.

In some embodiments, the antibody comprises the E345R/E430G/S440Y mutation and is an IgG1 isotype, optionally further comprising a L234A/L235A mutation when compared to the wild-type IgG1.

In some embodiments, the antibody comprises the E345R/E430G/S440Y mutation and is an IgG1 isotype, optionally further comprising a L234F/L235E/D265A mutation when compared to the wild-type IgG1.

In some embodiments, the antibody comprises the E345R/E430G/S440Y mutation and is an IgG1 isotype, optionally further comprising a K214T/E233P/L234V/L235A/G236-deleted/A327G/P331A/D365E/L358M mutation when compared to the wild-type IgG1.

In some embodiments, the antibody comprises the E345R/E430G/S440Y mutation and is an IgG1 isotype, optionally further comprising a L234A/L235A/G237A/P238S/H268A/A330S/P331S mutation when compared to the wild-type IgG1.

In some embodiments, the antibody comprises the E345R/E430G/S440Y mutation and is an IgG1 isotype and further comprises a L234A/L235A/G237A/P238S/H268A/A330S/P331S mutation when compared to the wild-type IgG1.

In some embodiments, the antibody comprises the E345R/E430G/S440Y mutation and is an IgG2 isotype, optionally further comprising a V234A/G237A/P238S/H268A/V309L/A330S/P331S mutation when compared to the wild-type IgG2.

In some embodiments, the antibody comprises the E345R/E430G/S440Y mutation and is an IgG2 isotype and further comprises a V234A/G237A/P238S/H268A/V309L/A330S/P331S mutation when compared to the wild-type IgG2.

In some embodiments, the antibody comprises the E345R/E430G/S440Y mutation and is an IgG2 isotype, optionally further comprising a V234A/G237A mutation when compared to the wild-type IgG2.

In some embodiments, the antibody comprises the E345R/E430G/S440Y mutation and is an IgG2 isotype, optionally further comprising a H268Q/V309L/A330S/P331S mutation when compared to the wild-type IgG2.

In some embodiments, the antibody comprises the E345R/E430G/S440Y mutation and is an IgG3 isotype.

In some embodiments, the antibody comprises the E345R/E430G/S440Y mutation and is an IgG4 isotype, optionally further comprising a F234A/L235A mutation when compared to the wild-type IgG4.

In some embodiments, the antibody comprises the E345R/E430G/S440Y mutation and is an IgG4 isotype, optionally further comprising a S228P/F234A/L235A/G237A/P238S mutation when compared to the wild-type IgG4.

In some embodiments, the antibody comprises the E345R/E430G/S440Y mutation and is an IgG4 isotype, optionally further comprising a S228P/F234A/L235A/G236-deleted/G237A/P238S mutation when compared to the wild-type IgG4

In some embodiments, the antibody comprises the E345R/E430G/S440Y mutation and is an IgG4 isotype, optionally further comprising a S228P/F234A/L235A mutation when compared to the wild-type IgG4.

In some embodiments, the antibody comprises the E345R/E430G/S440Y mutation and is an IgG4 isotype and comprises the S228P/F234A/L235A mutation when compared to the wild-type IgG4.

In some embodiments, the antibody comprises the E345R/E430G/S440Y mutation and has agonistic activity independent of antibody cross-linking, wherein agonistic activity is measured by measuring antibody-induced production of secreted embryonic alkaline phosphatase (SEAP) expressed under the control of NFκB-inducible promoter from Hek-293 cells.

In some embodiments, the antibody comprises the E345R/E430G/S440Y mutation and binds TNFR superfamily member tumor necrosis factor receptor 1 (SEQ ID NO: 1), Tumor necrosis factor receptor 2 (SEQ ID NO: 2), lymphotoxin beta receptor (SEQ ID NO: 3), OX40 (SEQ ID NO: 4), CD40 (SEQ ID NO: 5), Fas receptor (SEQ ID NO: 6), decoy receptor 3 (SEQ ID NO: 7), CD27 (SEQ ID NO: 8), CD30 (SEQ ID NO: 9), CD137 (SEQ ID NO: 10), death receptor 4 (SEQ ID NO: 11), death receptor 5 (SEQ ID NO: 12), decoy receptor 1 (SEQ ID NO: 13), decoy receptor 2 (SEQ ID NO: 14), RANK (SEQ ID NO: 15), osteoprotegerin (SEQ ID NO: 16), TWEAK receptor (SEQ ID NO: 17), TACI (SEQ ID NO: 18), BAFF receptor (SEQ ID NO: 19), herpesvirus entry mediator (SEQ ID NO: 20), nerve growth factor receptor (SEQ ID NO: 21), B-cell maturation antigen (SEQ ID NO: 22), GITR (SEQ ID NO: 23), TROY (SEQ ID NO: 24), death receptor 6 (SEQ ID NO: 25), death receptor 3 (SEQ ID NO: 26) or ectodysplasin A2 receptor (SEQ ID NO: 27).

In some embodiments, the antibody comprises the E345R/E430G/S440Y mutation and binds TNFR superfamily member OX40 (SEQ ID NO: 4), CD27 (SEQ ID NO: 8), CD40 (SEQ ID NO: 5), CD137 (SEQ ID NO: 10), or GITR (SEQ ID NO: 23).

In some embodiments, the antibody comprises the E345R/E430G/S440Y mutation and binds TNFR superfamily member OX40 (SEQ ID NO: 4).

In some embodiments, the antibody comprises the E345R/E430G/S440Y mutation and binds TNFR superfamily member CD27 (SEQ ID NO: 8).

In some embodiments, the antibody comprises the E345R/E430G/S440Y mutation and binds TNFR superfamily member CD40 (SEQ ID NO: 5).

In some embodiments, the antibody comprises the E345R/E430G/S440Y mutation and binds TNFR superfamily member CD137 (SEQ ID NO: 10).

In some embodiments, the antibody comprises the E345R/E430G/S440Y mutation and binds TNFR superfamily member GITR (SEQ ID NO: 23).

The antibody comprising the E345R/E430G/S440Y mutation is suitable for use in therapy, for example in treating cancer.

The antibody comprising the E345R/E430G/S440Y mutation is suitable for use in therapy, for example in treating cancer.

The antibody comprising the E345R/E430G/S440Y mutation is suitable for use in therapy, for example in treating a solid tumor.

The antibody comprising the E345R/E430G/S440Y mutation is suitable for use in therapy, for example in treating a melanoma.

The antibody comprising the E345R/E430G/S440Y mutation is suitable for use in therapy, for example in treating a lung cancer.

The antibody comprising the E345R/E430G/S440Y mutation is suitable for use in therapy, for example in treating a squamous non-small cell lung cancer (NSCLC).

The antibody comprising the E345R/E430G/S440Y mutation is suitable for use in therapy, for example in treating a non-squamous NSCLC.

The antibody comprising the E345R/E430G/S440Y mutation is suitable for use in therapy, for example in treating a lung adenocarcinoma.

The antibody comprising the E345R/E430G/S440Y mutation is suitable for use in therapy, for example in treating a renal cell carcinoma (RCC) (e.g., a kidney clear cell carcinoma or a kidney papillary cell carcinoma), or a metastatic lesion thereof.

The antibody comprising the E345R/E430G/S440Y mutation is suitable for use in therapy, for example in treating a mesothelioma.

The antibody comprising the E345R/E430G/S440Y mutation is suitable for use in therapy, for example in treating a nasopharyngeal carcinoma (NPC).

The antibody comprising the E345R/E430G/S440Y mutation is suitable for use in therapy, for example in treating a colorectal cancer.

The antibody comprising the E345R/E430G/S440Y mutation is suitable for use in therapy, for example in treating a prostate cancer or castration-resistant prostate cancer.

The antibody comprising the E345R/E430G/S440Y mutation is suitable for use in therapy, for example in treating a stomach cancer.

The antibody comprising the E345R/E430G/S440Y mutation is suitable for use in therapy, for example in treating an ovarian cancer.

The antibody comprising the E345R/E430G/S440Y mutation is suitable for use in therapy, for example in treating a gastric cancer.

The antibody comprising the E345R/E430G/S440Y mutation is suitable for use in therapy, for example in treating a liver cancer.

The antibody comprising the E345R/E430G/S440Y mutation is suitable for use in therapy, for example in treating pancreatic cancer.

The antibody comprising the E345R/E430G/S440Y mutation is suitable for use in therapy, for example in treating a thyroid cancer.

The antibody comprising the E345R/E430G/S440Y mutation is suitable for use in therapy, for example in treating a squamous cell carcinoma of the head and neck.

The antibody comprising the E345R/E430G/S440Y mutation is suitable for use in therapy, for example in treating a carcinomas of the esophagus or gastrointestinal tract.

The antibody comprising the E345R/E430G/S440Y mutation is suitable for use in therapy, for example in treating a breast cancer.

The antibody comprising the E345R/E430G/S440Y mutation is suitable for use in therapy, for example in treating a fallopian tube cancer.

The antibody comprising the E345R/E430G/S440Y mutation is suitable for use in therapy, for example in treating a brain cancer.

The antibody comprising the E345R/E430G/S440Y mutation is suitable for use in therapy, for example in treating an urethral cancer.

The antibody comprising the E345R/E430G/S440Y mutation is suitable for use in therapy, for example in treating a genitourinary cancer.

The antibody comprising the E345R/E430G/S440Y mutation is suitable for use in therapy, for example in treating an endometriosis.

The antibody comprising the E345R/E430G/S440Y mutation is suitable for use in therapy, for example in treating a cervical cancer.

The antibody comprising the E345R/E430G/S440Y mutation is suitable for use in therapy, for example in treating a metastatic lesion of the cancer.

"Antibody-dependent cellular cytotoxicity", "antibody-dependent cell-mediated cytotoxicity" or "ADCC" is a mechanism for inducing cell death that depends upon the interaction of antibody-coated target cells with effector cells possessing lytic activity, such as natural killer cells, monocytes, macrophages and neutrophils via Fc gamma receptors (FcγR) expressed on effector cells. For example, NK cells express FcγRIIIA, whereas monocytes express FcγRI, FcγRII and FcγRIIIA. Death of the antibody-coated target cell, such as TNFR expressing cells, occurs because of effector cell activity through the secretion of membrane pore-forming proteins and proteases. To assess ADCC activity of the antibodies of the invention, the antibodies may be added to TNFR expressing cells in combination with immune effector cells, which may be activated by the antigen antibody complexes resulting in cytolysis of the target cell. Cytolysis may be detected by the release of label (e.g. radioactive substrates, fluorescent dyes or natural intracellular proteins) from the lysed cells. Exemplary effector cells for such assays include peripheral blood mononuclear cells (PBMC) and NK cells. Exemplary target cells include cells expressing the TNFR either endogenously or recombinantly, such as Tregs. In an exemplary assay, target cells are used with a ratio of 1 target cell to 50 effector cells. Target cells are pre-labeled with BATDA (PerkinElmer) for 20 minutes at 37° C., washed twice and resuspended in DMEM, 10% heat-inactivated FBS, 2 mM L-glutamine (all from Invitrogen). Target ($1\times10^4$ cells) and effector cells ($0.5\times10^6$ cells) are combined and 100 µl of cells are added to the wells of 96-well U-bottom plates. An additional 100 µl is added with or without the test antibodies. The plates are centrifuged at 200 g for 3 minutes, incubated at 37° C. for 2 hours, and then centrifuged again at 200 g for 3 minutes. A total of 20 µl of supernatant is removed per well and cell lysis is measured by the addition of 200 µl of the DELPHIA Europium-based reagent (PerkinElmer). Data is normalized to maximal cytotoxicity with 0.67% Triton X-100 (Sigma Aldrich) and minimal control determined by spontaneous release of BATDA from target cells in the absence of any antibody. Alternatively, ADCC activity may be assessed by evaluating activation of FcγRIIIA in a reporter gene assay in which activation of the receptor leads to expression of a luciferase reporter as described herein.

"Antibody-dependent cellular phagocytosis" ("ADCP") refers to a mechanism of elimination of antibody-coated target cells by internalization by phagocytic cells, such as macrophages or dendritic cells. ADCP may be evaluated by using monocyte-derived macrophages as effector cells and Daudi cells (ATCC® CCL-213™) or B cell leukemia or lymphoma or tumor cells expressing TNFR as target cells engineered to express GFP or another labeled molecule. Effector:target cell ratio may be for example 4:1. Effector cells may be incubated with target cells for 4 hours with or without the antibody of the invention. After incubation, cells may be detached using accutase. Macrophages may be identified with anti-CD11b and anti-CD14 antibodies coupled to a fluorescent label, and percent phagocytosis may be determined based on % GFP fluorescence in the $CD11^+$ $CD14^+$ macrophages using standard methods.

The effector functions, for example ADCC, ADCP and/or CDC of the antibodies of the invention may further be enhanced by introducing additional mutations into the antibody Fc which enhances binding of the antibody to an activating Fcγ receptor (FcγR) or complement.

Fc positions that may be mutated to increase binding of the antibodies of the invention to the activating Fcγ and/or to enhance antibody effector functions are those described for example in U.S. Pat. No. 6,737,056, U.S. Patent Publ. No. 2015/0259434, Shields et al. (2001) *J Biol Chem* 276:

6591-604, Lazar et al. (2006) *Proc Natl Acad Sci USA* 103: 4005-10, Stavenhagen et al. (2007) *Cancer Res* 67: 8882-90, Richards et al. (2008) *Mol Cancer Ther* 7: 2517-27 and Diebolder et al. (2014) *Science* 343: 1260-3 and include positions 236, 239, 243, 256, 290, 292, 298, 300, 305, 312, 326, 330, 332, 333, 334, 360, 339, 378, 396 or 430 (residue numbering according to the EU index). Exemplary mutations that may be made singularly or in combination are G236A, S239D, F243L, T256A, K290A, R292P, S298A, Y300L, V305L, K326A, A330K, I332E, E333A, K334A, A339T and P396L mutations. Exemplary combination mutations that result in antibodies with increased ADCC or ADCP are S239D/I332E, S298A/E333A/K334A, F243L/R292P/Y300L, F243L/R292P/Y300L/P396L, F243L/R292P/Y300L/V305I/P396L and G236A/S239D/I332E mutations on IgG1.

Fc positions that may be mutated to enhance CDC of the antibodies of the invention are those described for example in Int. Patent Appl. WO2014/108198, Idusogie et al. (2001) *J Immunol* 166: 2571-5 and Moore et al. (2010) MAbs 2: 181-9, and include positions 267, 268, 324, 326, 333, 345 and 430. Exemplary mutations that may be made singularly or in combination are S267E, H268F, S324T, K326A, K326W, E333A, E430S, E430F and E430T mutations. Exemplary combination mutations that result in antibodies with increased CDC are K326A/E333A, K326W/E333A, H268F/S324T, S267E/H268F, S267E/S324T and S267E/H268F/S324T mutations on IgG1.

"Complement-dependent cytotoxicity", or "CDC", refers to a mechanism for inducing cell death in which the Fc effector domain of a target-bound antibody binds and activates complement component C1q which in turn activates the complement cascade leading to target cell death. Activation of complement may also result in deposition of complement components on the target cell surface that facilitate ADCC by binding complement receptors (e.g., CR3) on leukocytes. CDC of TNFR expressing cells may be measured for example by plating Daudi cells at $1\times10^5$ cells/well (50 μl/well) in RPMI-B (RPM1 supplemented with 1% BSA), adding 50 μl of test antibodies to the wells at final concentration between 0-100 μg/ml, incubating the reaction for 15 min at room temperature, adding 11 μl of pooled human serum to the wells, and incubation the reaction for 45 min at 37° C. Percentage (%) lysed cells may be detected as % propidium iodide stained cells in FACS assay using standard methods.

The ability of the antibodies of the invention to induce ADCC may also be enhanced by engineering their oligosaccharide component. Human IgG1 or IgG3 are N-glycosylated at Asn297 with most of the glycans in the well-known biantennary G0, G0F, G1, G1F, G2 or G2F forms. Antibodies produced by non-engineered CHO cells typically have a glycan fucose content of about at least 85%. The removal of the core fucose from the biantennary complex-type oligosaccharides attached to the Fc regions enhances the ADCC of antibodies via improved FcγRIIIa binding without altering antigen binding or CDC activity. Such mAbs may be achieved using different methods reported to lead to the successful expression of relatively high defucosylated antibodies bearing the biantennary complex-type of Fc oligosaccharides such as control of culture osmolality (Konno et al. (2012) *Cytotechnology* 64: 249-65), application of a variant CHO line Lec13 as the host cell line (Shields et al. 2002) *J Biol Chem* 277: 26733-40), application of a variant CHO line EB66 as the host cell line (Olivier et al. (2010) MAbs 2: 405-15, application of a rat hybridoma cell line YB2/0 as the host cell line (Shinkawa et al. (2003) *J Biol Chem* 278: 3466-73), introduction of small interfering RNA specifically against the cc 1,6-fucosyltrasferase (FUT8) gene (Mori et al. (2004) *Biotechnol Bioeng* 88: 901-8), or co-expression of β-1,4-N-acetylglucosaminyltransferase III and Golgi α-mannosidase II or a potent alpha-mannosidase I inhibitor, kifunensine (Ferrara et al. (2006) *J Biol Chem* 281: 5032-6; Ferrara et al. (2006) *Biotechnol Bioeng* 93: 851-61; Zhou et al. (2008) *Biotechnol Bioeng* 99: 652-65).

In some embodiments, the anti-TNFR superfamily member antibody of the invention comprises a second mutation that enhances ADCC, ADCP and/or CDC of the antibody.

In some embodiments, the anti-TNFR superfamily member antibody of the invention comprises a second mutation that enhances ADCC, ADCP and/or CDC of the antibody selected from the group consisting of a G236A mutation, a S239D mutation, a F243L mutation, a T256A mutation, a K290A mutation, a R292P mutation, a S298A mutation, a Y300L mutation, a V305L mutation, a K326A mutation, a A330K mutation, a I332E mutation, an E333A mutation, a K334A mutation, an A339T mutation, a P396L mutation, a S267E mutation, a H268F mutation, a S324T mutation, a K326A mutation, a K326W mutation, an E333A mutation, an E430S mutation, an E430F mutation and an E430T mutation.

In some embodiments, the anti-TNFR superfamily member antibody of the invention comprises a second mutation that enhances ADCC, ADCP and/or CDC of the antibody selected from the group consisting of a S239D/I332E mutation, a S298A/E333A/K334A mutation, a F243L/R292P/Y300L mutation, a F243L/R292P/Y300L/P396L mutation, a F243L/R292P/Y300L/V305I/P396L mutation, a G236A/S239D/I332E mutation, a K326A/E333A mutation, a K326W/E333A mutation, a H268F/S324T mutation, a S267E/H268F mutation, a S267E/S324T mutation and a S267E/H268F/S324T mutation.

The ability of antibodies of the invention to induce ADCC may be enhanced by engineering their oligosaccharide component. Human IgG1 or IgG3 are N-glycosylated at Asn297 with most glycans in the well-known biantennary G0, G0F, G1, G1F, G2 or G2F forms. Antibodies produced by non-engineered CHO cells typically have a glycan fucose content of about at least 85%. The removal of the core fucose from the biantennary complex-type oligosaccharides attached to the Fc regions enhances the ADCC of antibodies via improved FcγRIIIa binding without altering antigen binding or CDC activity.

In some embodiments, the anti-TNFR superfamily member antibody of the invention has a biantennary glycan structure with fucose content of about between 0% to about 15%, for example 15%, 14%, 13%, 12%, 11% 10%, 9%, 8%, 7%, 6%, 5%, 4%, 3%, 2%, 1% or 0%.

In some embodiments, the anti-TNFR superfamily member antibody of the invention has a biantennary glycan structure with fucose content of about 50%, 40%, 45%, 40%, 35%, 30%, 25%, 20%, 15%, 14%, 13%, 12%, 11% 10%, 9%, 8%, 7%, 6%, 5%, 4%, 3%, 2%, 1% or 0%.

"Fucose content" means the amount of the fucose monosaccharide within the sugar chain at Asn297. The relative amount of fucose is the percentage of fucose-containing structures related to all glycostructures. These may be characterized and quantified by multiple methods, for example: 1) using MALDI-TOF of N-glycosidase F treated sample (e.g. complex, hybrid and oligo- and high-mannose structures) as described in Intl. Patent Publ. No. WO2008/077546; 2) by enzymatic release of the Asn297 glycans with subsequent derivatization and detection/quantitation by HPLC (UPLC) with fluorescence detection and/or HPLC-MS (UPLC-MS); 3) intact protein analysis of the native or reduced mAb, with or without treatment of the Asn297 glycans with Endo S or other enzyme that cleaves between the first and the second GlcNAc monosaccharides, leaving the fucose attached to the first GlcNAc; 4) digestion of the mAb to constituent peptides by enzymatic digestion (e.g., trypsin or endopeptidase Lys-C), and subsequent separation, detection and quantitation by HPLC-MS (UPLC-MS) or 5) separation of the mAb oligosaccharides from the mAb protein by specific enzymatic deglycosylation with PNGase F at Asn 297. The oligosaccharides released may be labeled with a fluorophore, separated and identified by various complementary techniques which allow fine characterization of the glycan structures by matrix-assisted laser desorption ionization (MALDI) mass spectrometry by comparison of the experimental masses with the theoretical masses, determination of the degree of sialylation by ion exchange HPLC (GlycoSep C), separation and quantification of the oligosaccharide forms according to hydrophilicity criteria by normal-phase HPLC (GlycoSep N), and separation and quantification of the oligosaccharides by high performance capillary electrophoresis-laser induced fluorescence (HPCE-LIF).

"Low fucose" or "low fucose content" refers to antibodies with fucose content of about 0%-15%.

"Normal fucose" or "normal fucose content" refers to antibodies with fucose content of about over 50%, typically about over 60%, 70%, 80% or over 85%.

In instances where effector functionality is not desired, the antibodies of the invention may further be engineered to introduce at least one mutation in the antibody Fc that reduces binding of the antibody to an activating Fcγ receptor (FcγR) and/or reduces Fc effector functions such as C1q binding, complement dependent cytotoxicity (CDC), antibody-dependent cell-mediated cytotoxicity (ADCC) or phagocytosis (ADCP).

Fc positions that may be mutated to reduce binding of the antibody to the activating FcγR and subsequently to reduce effector functions are those described for example in Shields et al. (2001) *J Biol Chem* 276: 6591-604, Intl. Patent Publ. No. WO2011/066501, U.S. Pat. Nos. 6,737,056 and 5,624,821, Xu et al. (2000) *Cell Immunol* 200: 16-26, Alegre et al. (1994) *Transplantation* 57: 1537-43, Bolt et al. (1993) *Eur J Immunol* 23: 403-11, Cole et al. (1999) *Transplantation* 68: 563-71, Rother et al. (2007) *Nat Biotechnol* 25: 1256-64, Ghevaert et al. (2008) *J Clin Invest* 118: 2929-38, An et al. (2009) MAbs 1: 572-9 and include positions 214, 233, 234, 235, 236, 237, 238, 265, 267, 268, 270, 295, 297, 309, 327, 328, 329, 330, 331 and 365. Exemplary mutations that may be made singularly or in combination are K214T, E233P, L234V, L234A, deletion of G236, V234A, F234A, L235A, G237A, P238A, P238S, D265A, S267E, H268A, H268Q, Q268A, N297A, A327Q, P329A, D270A, Q295A, V309L, A327S, L328F, A330S and P331S mutations on IgG1, IgG2, IgG3 or IgG4. Exemplary combination mutations that may be made to reduced ADCC are L234A/L235A on IgG1, V234A/G237A/P238S/H268A/V309L/A330S/P331S on IgG2, F234A/L235A on IgG4, S228P/F234A/L235A on IgG4, N297A on IgG1, IgG2, IgG3 or IgG4, V234A/G237A on IgG2, K214T/E233P/L234V/L235A/G236-deleted/A327G/P331A/D365E/L358M on IgG1, H268Q/V309L/A330S/P331S on IgG2, S267E/L328F on IgG1, L234F/L235E/D265A on IgG1, L234A/L235A/G237A/P238S/H268A/A330S/P331S on IgG1, S228P/F234A/L235A/G237A/P238S on IgG4, and S228P/F234A/L235A/G236-deleted/G237A/P238S on IgG4. Hybrid IgG2/4 Fc domains may also be used, such as Fc with residues 117-260 from IgG2 and residues 261-447 from IgG4.

A S228P mutation may be made into IgG4 antibodies to enhance IgG4 stability. In some embodiments, the antibodies of the invention comprise a second mutation selected from the group consisting of a K214T mutation, a E233P mutation, a L234V mutation, a L234A mutation, deletion of a G236, a V234A mutation, a F234A mutation, a L235A mutation, a G237A mutation, a P238A mutation, a P238S mutation, a D265A mutation, a S267E mutation, a H268A mutation, a H268Q mutation, a Q268A mutation, a N297A mutation, a A327Q mutation, a P329A mutation, a D270A mutation, a Q295A mutation, a V309L mutation, a A327S mutation, a L328F mutation, a A330S mutation and a P331S mutation, wherein residue numbering is according to the EU Index.

The antibodies of the invention may be further engineered to modulate antibody half-life by introducing additional Fc mutations, such as those described for example in Dall'Acqua et al. (2006) *J Biol Chem* 281: 23514-24, Zalevsky et al. (2010) *Nat Biotechnol* 28: 157-9, Hinton et al. (2004) *J Biol Chem* 279: 6213-6, Hinton et al. (2006) *J Immunol* 176: 346-56, Shields et al. (2001) *J Biol Chem* 276: 6591-604, Petkova et al. (2006) *Int Immunol* 18: 1759-69, Datta-Mannan et al. (2007) *Drug Metab Dispos* 35: 86-94, Vaccaro et al. (2005) *Nat Biotechnol* 23: 1283-8, Yeung et al. (2010) *Cancer Res* 70: 3269-77 and Kim et al. (1999) *Eur J Immunol* 29: 2819-25, and include positions 250, 252, 253, 254, 256, 257, 307, 376, 380, 428, 434 and 435. Exemplary mutations that may be made singularly or in combination are T250Q, M252Y, I253A, S254T, T256E, P257I, T307A, D376V, E380A, M428L, H433K, N434S, N434A, N434H, N434F, H435A and H435R mutations. Exemplary singular or combination mutations that may be made to increase the half-life of the antibody are M428L/N434S, M252Y/S254T/T256E, T250Q/M428L, N434A and T307A/E380A/N434A mutations. Exemplary singular or combination mutations that may be made to reduce the half-life of the antibody are H435A, P257I/N434H, D376V/N434H, M252Y/S254T/T256E/H433K/N434F, T308P/N434A and H435R mutations.

Antibodies of the invention further comprising conservative modifications are within the scope of the invention.

"Conservative modifications" refer to amino acid modifications that do not significantly affect or alter the binding characteristics of the antibody containing the amino acid sequences. Conservative modifications include amino acid substitutions, additions and deletions. Conservative substitutions are those in which the amino acid is replaced with an amino acid residue having a similar side chain. The families of amino acid residues having similar side chains are well defined and include amino acids with acidic side chains (e.g., aspartic acid, glutamic acid), basic side chains (e.g., lysine, arginine, histidine), nonpolar side chains (e.g., alanine, valine, leucine, isoleucine, proline, phenylalanine, methionine), uncharged polar side chains (e.g., glycine, asparagine, glutamine, cysteine, serine, threonine, tyrosine, tryptophan), aromatic side chains (e.g., phenylalanine, tryptophan, histidine, tyrosine), aliphatic side chains (e.g., glycine, alanine, valine, leucine, isoleucine, serine, threonine), amide (e.g., asparagine, glutamine), beta-branched side chains (e.g., threonine, valine, isoleucine) and sulfur-containing side chains (cysteine, methionine). Furthermore, any native residue in the polypeptide may also be substituted with alanine, as has been previously described for alanine scanning mutagenesis (MacLennan et al. (1998) *Acta Physiol Scand Suppl* 643: 55-67; Sasaki et al. (1998) *Adv*

*Biophys* 35: 1-24) Amino acid substitutions to the antibodies of the invention may be made by known methods for example by PCR mutagenesis (U.S. Pat. No. 4,683,195). Alternatively, libraries of variants may be generated for example using random (NNK) or non-random codons, for example DVK codons, which encode 11 amino acids (Ala, Cys, Asp, Glu, Gly, Lys, Asn, Arg, Ser, Tyr, Trp). The resulting antibody variants may be tested for their characteristics using assays described herein.

The antibodies of the invention may be post-translationally modified by processes such as glycosylation, isomerization, deglycosylation or non-naturally occurring covalent modification such as the addition of polyethylene glycol moieties (pegylation) and lipidation. Such modifications may occur in vivo or in vitro. For example, the antibodies of the invention may be conjugated to polyethylene glycol (PEGylated) to improve their pharmacokinetic profiles. Conjugation may be carried out by techniques known to those skilled in the art. Conjugation of therapeutic antibodies with PEG has been shown to enhance pharmacodynamics while not interfering with function (Leong et al. (2001) *Cytokine* 16: 106-19; Yang et al. (2003) *Protein Eng* 16: 761-70; Knight et al. (2004) *Platelets* 15: 409-18).

Antibodies of the invention may be modified to improve stability, selectivity, cross-reactivity, affinity, immunogenicity or other desirable biological or biophysical property are within the scope of the invention. Stability of an antibody is influenced by a number of factors, including (1) core packing of individual domains that affects their intrinsic stability, (2) protein/protein interface interactions that have impact upon the HC and LC pairing, (3) burial of polar and charged residues, (4) H-bonding network for polar and charged residues; and (5) surface charge and polar residue distribution among other intra- and inter-molecular forces (Worn et al. (2001) *J Mol Biol* 305: 989-1010). Potential structure destabilizing residues may be identified based upon the crystal structure of the antibody or by molecular modeling in certain cases, and the effect of the residues on antibody stability may be tested by generating and evaluating variants harboring mutations in the identified residues. One of the ways to increase antibody stability is to raise the thermal transition midpoint ($T_m$) as measured by differential scanning calorimetry (DSC). In general, the protein $T_m$ is correlated with its stability and inversely correlated with its susceptibility to unfolding and denaturation in solution and the degradation processes that depend on the tendency of the protein to unfold (Remmele et al. (2000) *Biopharm.* 13: 36-46). A number of studies have found correlation between the ranking of the physical stability of formulations measured as thermal stability by DSC and physical stability measured by other methods (Maa et al. (1996) *Int. J. Pharm.* 140: 155-68; Remmele et al. (1997) *Pharm. Res.* 15: 200-8; Gupta et al. (2003) *AAPS Pharm Sci.* 5E8: 2003; Bedu-Addo et al. (2004) *Pharm. Res.* 21: 1353-61; Zhang et al. (2004) *J. Pharm. Sci.* 93: 3076-89). Formulation studies suggest that a Fab $T_m$ has implication for long-term physical stability of a corresponding mAb.

C-terminal lysine (CTL) may be removed from injected antibodies by endogenous circulating carboxypeptidases in the blood stream (Cai et al. (2011) *Biotechnol Bioeng* 108: 404-12). During manufacturing, CTL removal may be controlled to less than the maximum level by control of concentration of extracellular $Zn^{2+}$, EDTA or EDTA-$Fe^{3+}$ as described in U.S. Patent Publ. No. US20140273092. CTL content in antibodies can be measured using known methods.

In some embodiments, the antibodies of the invention have a C-terminal lysine content of about 10% to about 90%, about 20% to about 80%, about 40% to about 70%, about 55% to about 70%, or about 60%.

In some embodiments, the antibodies of the invention have a C-terminal lysine content of about 0%, 5%, 10%, 20%, 30%, 40%, 50%, 60%, 70%, 80%, 90% or 100%.

Methods of Generating Antibodies of the Invention

The antibodies of the invention with engineered Fc domains may be generated using standard cloning and expression technologies using wild type IgG1, IgG2, IgG3 or IgG4 sequences as templates. For example, site-directed mutagenesis or PCR-mediated mutagenesis may be performed to introduce the mutation(s) in the antibody Fc and the effect on antibody binding to FcγR, agonistic activity or other property of interest, may be evaluated using the methods described herein.

The VH and the VL domains of the anti-TNFR superfamily member antibodies may be generated de novo.

For example, the hybridoma method of Kohler and Milstein, *Nature* 256:495, 1975 may be used to generate monoclonal antibodies. In the hybridoma method, a mouse or other host animal, such as a hamster, rat or monkey, is immunized with human TNFR or an extracellular domain of a TNFR followed by fusion of spleen cells from immunized animals with myeloma cells using standard methods to form hybridoma cells (Goding, Monoclonal Antibodies: Principles and Practice, pp. 59-103, Academic Press, 1986). Colonies arising from single immortalized hybridoma cells are screened for production of antibodies with desired properties, such as specificity of binding, cross-reactivity or lack thereof, and affinity for the antigen.

Various host animals may be used to produce the anti-TNFR superfamily member antibodies of the invention. For example, Balb/c mice may be used to generate mouse anti-human TNFR superfamily member antibodies. The antibodies made in Balb/c mice and other non-human animals may be humanized using various technologies to generate more human-like sequences.

Exemplary humanization techniques including selection of human acceptor frameworks are known and include CDR grafting (U.S. Pat. No. 5,225,539), SDR grafting (U.S. Pat. No. 6,818,749), Resurfacing ((Padlan (1991) *Mol Immunol* 28: 489-98), Specificity Determining Residues Resurfacing (U.S. Patent Publ. No. 2010/0261620), human framework adaptation (U.S. Pat. No. 8,748,356) or superhumanization (U.S. Pat. No. 7,709,226). In these methods, CDRs of parental antibodies are transferred onto human frameworks that may be selected based on their overall homology to the parental frameworks, based on similarity in CDR length, or canonical structure identity, or a combination thereof.

Humanized antibodies may be further optimized to improve their selectivity or affinity to a desired antigen by incorporating altered framework support residues to preserve binding affinity (backmutations) by techniques such as those described in Int. Patent Publ. Nos. WO1090/007861 and WO1992/22653, or by introducing variation at any of the CDRs for example to improve affinity of the antibody.

Transgenic animals, such as mice or rat carrying human immunoglobulin (Ig) loci in their genome may be used to generate human antibodies against a target protein, and are described in for example U.S. Pat. No. 6,150,584, Int. Patent Publ. No. WO99/45962, Int. Patent Publ. Nos. WO2002/066630, WO2002/43478, WO2002/043478 and WO1990/04036, Lonberg et al. (1994) *Nature* 368: 856-9; Green et al. (1994) *Nat Genet* 7: 13-21; Green et al. (1998) *J Exp Med* 188: 483-95; Lonberg et al. (1995) *Int Rev Immunol* 13:

65-93; Bruggemann et al. (1991) *Eur J Immunol* 21: 1323-6; Fishwild et al. (1996) *Nat Biotechnol* 14: 845-51; Mendez et al. (1997) *Nat Genet* 15: 146-56; Green (1999) *J Immunol Methods* 231: 11-23; Yang et al. (1999) *Cancer Res* 59: 1236-43; Bruggemann et al. (1997) *Curr Opin Biotechnol* 8: 455-8. The endogenous immunoglobulin loci in such animal may be disrupted or deleted, and at least one complete or partial human immunoglobulin locus may be inserted into the genome of the animal using homologous or non-homologous recombination, using transchromosomes, or using minigenes. Companies such as Regeneron (http://_www_regeneron_com), Harbour Antibodies (http://_www_harbourantibodies_com), Open Monoclonal Technology, Inc. (OMT) (http://_www_omtinc_net), KyMab (http://_www_kymab_com), Trianni (http://_www.trianni_com) and Ablexis (http://_www_ablexis_com) may be engaged to provide human antibodies directed against a selected antigen using technologies as described above.

Human antibodies may be selected from a phage display library, where the phage is engineered to express human immunoglobulins or portions thereof such as Fabs, single chain antibodies (scFv), or unpaired or paired antibody variable regions (Knappik et al. (2000) *J Mol Biol* 296: 57-86; Krebs et al. (2001) *J Immunol Methods* 254: 67-84; Vaughan et al. (1996) *Nat Biotechnol* 14: 309-14; Sheets et al. (1998) *Proc Natl Acad Sci USA* 95: 6157-62; Clackson et al. (1991) *Nature* 352: 624-8; Marks et al. (1991) *J Mol Biol* 222: 581-97). The antibodies of the invention may be isolated for example from phage display library expressing antibody heavy and light chain variable regions as fusion proteins with bacteriophage pIX coat protein as described in (Shi et al. (2010) *J Mol Biol* 397: 385-96, and Int. Patent Publ. No. WO09/085462). The libraries may be screened for phage binding to human and/or cyno TNFR and the obtained positive clones may be further characterized, the Fabs isolated from the clone lysates, and expressed as full-length IgGs. Such phage display methods for isolating human antibodies are described in for example: U.S. Pat. Nos. 5,223,409, 5,403,484, 5,571,698, 5,427,908, 5,580,717, 5,969,108, 6,172,197, 5,885,793; 6,521,404; 6,544,731; 6,555,313; 6,582,915 and 6,593,081.

Preparation of immunogenic antigens and monoclonal antibody production may be performed using any suitable technique, such as recombinant protein production. The immunogenic antigens may be administered to an animal in the form of purified protein, or protein mixtures including whole cells or cell or tissue extracts, or the antigen may be formed de novo in the animal's body from nucleic acids encoding said antigen or a portion thereof.

The VH/VL regions of the anti-TNFR superfamily member antibodies of the invention may also be obtained from existing anti-TNFR superfamily receptor antibodies.

The VH and the VL regions of anti-OX40 antibodies described in U.S. Pat. Nos. 8,133,983, 7,960,515, U.S. Patent Publ. No. US2013/0280275, Intl. Patent Publ. No. WO2013/028231 and U.S. Patent Publ. No. US2014/0377284 may be used to engineer antibodies of the invention. Further, the VH/VL regions of anti-OX40 antibodies MEDI-6469, BMS-986178, MOXR-0916, MEDI-6383, MEDI-0562, PF-04518600 or GSK-3174998 may be used. Additional exemplary VH and VL regions that may be used to generate engineered anti-OX40 antibodies of the invention are:

```
(VH of antibody SF2 described in US2014/0377284)
                                          SEQ ID NO: 51
QVQLVQSGAEVKKPGSSVKVSCKASGYTFKDYTMHWVRQAPGQGLEWIGG

IYPNNGGSTYNQNFKDRVTLTADKSTSTAYMELSSLRSEDTAVYYCARMG

YHGPHLDFDVWGQGTTVTVSS

(VL of antibody SF2 described in US2014/0377284)
                                          SEQ ID NO: 52
DIQMTQSPSSLSASVGDRVTITCKASQDVGAAVAWYQQKPGKAPKLLIYW

ASTRHTGVPSRFSGSGSGTDFTLTISSLQPEDFATYYCQQYINYPLTFGG

GTKVEIK

(VH of 12H3VH1VL1 described in US2014/0377284)
                                          SEQ ID NO: 53
QVQLVQSGAEVKKPGSSVKVSCKASGYTFKDYTMHWVRQAPGQGLEWMGG

IYPNNGGSTYNQNFKDRVTITADKSTSTAYMELSSLRSEDTAVYYCARMG

YHGPHLDFDVWGQGTTVTVSS

(VL of 12H3VH1VL1 described in US2014/0377284)
                                          SEQ ID NO: 54
DIQMTQSPSSLSASVGDRVTITCKASQDVGAAVAWYQQKPGKAPKLLIYW

ASTRHTGVPSRFSGSGSGTDFTLTISSLQPEDFATYYCQQYINYPLTFGG

GTKVEIK

(VH of 20E5VH3VL2 described in US2014/0377284)
                                          SEQ ID NO: 55
QVQLVQSGAEVKKPGASVKVSCKASGYTFTSYVMHWVRQAPGQRLEWIGY

INPYNDGTKYNEKFKGRATLTSDKSASTAYMELSSLRSEDTAVYYCANYY

GSSLSMDYWGQGTLVTVSS

(VL of 20E5VH3VL2 described in US2014/0377284)
                                          SEQ ID NO: 56
DIQMTQSPSSLSASVGDRVTITCRASQDISNYLNWYQQKPGKAVKLLIYY

TSRLHSGVPSRFSGSGSGTDYTLTISSLQPEDFATYFCQQGNTLPWTFGQ

GTKVEIK
```

The VH and the VL regions of anti-CD40 antibodies that may be used to engineer antibodies of the invention are those of CP-870,893 and humanized S2C6 described in U.S. Pat. No. 7,288,251 (antibody 21.4.1) and U.S. Pat. No. 8,303,955, respectively, and anti-CD40 antibodies described in Int. Patent Publ. Nos. WO2001/056603, WO2001/083755, WO2013/034904 and WO2014/070934. Additional exemplary VH and VL regions that may be used to generate engineered anti-CD40 antibodies of the invention are:

```
(VH of M9 antibody)
                                          SEQ ID NO: 57
QLQLQESGPGLVKPSEILSLTCTVSGGSISSSSYYWGWIRQPPGKGLEWI

GNIYYRGDTYYSPSLKSRVTISVDTSKNQFSLKLNSVTAADTAVYYCAKG

FRFDYWGQGTLVTVSS

(VL of M9 antibody)
                                          SEQ ID NO: 58
QSALTQPPSASGSPGQSVTISCTGTSSDVGGYNYVSWYQQHPGKAPKLMI

YEVSKRPSGVPDRFSGSKSGNTASLTVSGLQAEDEADYYCSSYAGSNNLV

FGGGTKLTVL
```

The VH and the VL regions of anti-GITR antibodies that may be used to engineer antibodies of the invention are those of described in U.S. Pat. Nos. 7,812,135, 8,591,886 and 7,618,632, or in Int. Patent Publ. Nos. WO2011/028683, WO2013/039954, WO2005/007190 and WO2007/133822.

The VH and the VL regions of anti-CD27 antibodies that may be used to engineer antibodies of the invention are those of described in U.S. Pat. No. 9,169,325 and U.S. Pat. Publ. No. US20130183316.

The VH and the VL regions of anti-CD137 antibodies that may be used to engineer antibodies of the invention are those of described in U.S. Pat. Nos. 7,288,638, 8,716,452 and 8,821,867.

Antibodies of the invention engineered into full-length bispecific antibodies are within the scope of the invention.

"Full-length antibody" refers to an antibody having two full-length antibody heavy chains and two full-length antibody light chains A full-length antibody heavy chain (HC) consists of well-known heavy chain variable and constant domains VH, CH1, hinge, CH2, and CH3. A full-length antibody light chain (LC) consists of well-known light chain variable and constant domains VL and CL. The full-length antibody may be lacking the C-terminal lysine (K) in either one or both heavy chains.

Full-length bispecific antibodies may be generated for example using Fab arm exchange (or half molecule exchange) between two monospecific bivalent antibodies by introducing substitutions at the heavy chain CH3 interface in each half molecule to favor heterodimer formation of two antibody half molecules having distinct specificity either in vitro in cell-free environment or using co-expression. "Fab-arm" or "half molecule" refers to one heavy chain-light chain pair that specifically binds an antigen.

The Fab arm exchange reaction is the result of a disulfide-bond isomerization reaction and dissociation-association of CH3 domains. The heavy chain disulfide bonds in the hinge regions of the parental monospecific antibodies are reduced. The resulting free cysteines of one of the parental monospecific antibodies form an inter heavy-chain disulfide bond with cysteine residues of a second parental monospecific antibody molecule and simultaneously CH3 domains of the parental antibodies release and reform by dissociation-association. The CH3 domains of the Fab arms may be engineered to favor heterodimerization over homodimerization. The resulting product is a bispecific antibody having two Fab arms or half molecules which each bind a distinct epitope, i.e. an epitope on TNFR and an epitope on a second antigen.

"Homodimerization" refers to an interaction of two heavy chains having identical CH3 amino acid sequences. "Homodimer" refers to an antibody having two heavy chains with identical CH3 amino acid sequences.

"Heterodimerization" refers to an interaction of two heavy chains having non-identical CH3 amino acid sequences. "Heterodimer" refers to an antibody having two heavy chains with non-identical CH3 amino acid sequences.

The anti-TNFR superfamily member antibodies of the invention may be engineered into bispecific format using Knob-in-Hole (Genentech), CrossMAbs (Roche) and the electrostatically-matched (Chugai, Amgen, NovoNordisk, Oncomed), the LUZ-Y (Genentech), the Strand Exchange Engineered Domain body (SEEDbody) (EMD Serono), the Biclonic (Merus).

In the Knob-in-Hole strategy (see, e.g., Intl. Publ. No. WO 2006/028936), selected amino acids forming the interface of the CH3 domains in human IgG can be mutated at positions affecting CH3 domain interactions to promote heterodimer formation. An amino acid with a small side chain (hole) is introduced into a heavy chain of an antibody specifically binding a first antigen and an amino acid with a large side chain (knob) is introduced into a heavy chain of an antibody specifically binding a second antigen. After co-expression of the two antibodies, a heterodimer is formed because of the preferential interaction of the heavy chain with a "hole" with the heavy chain with a "knob". Exemplary CH3 substitution pairs forming a knob and a hole are (expressed as modified position in the first CH3 domain of the first heavy chain/modified position in the second CH3 domain of the second heavy chain): T366Y/F405A, T366W/F405W, F405W/Y407A, T394W/Y407T, T394S/Y407A, T366W/T394S, F405W/T394S and T366W/T366S_L368A_Y407V.

In the CrossMAb technology, in addition to utilizing the "knob-in-hole" strategy to promoter Fab arm exchange, one of the half arms have the CH1 and the CL domains exchanged to ensure correct light chain pairing of the resulting bispecific antibody (see e.g. U.S. Pat. No. 8,242,247).

Other cross-over strategies may be used to generate full-length bispecific antibodies by exchanging variable or constant, or both domains between the heavy chain and the light chain or within the heavy chain in the bispecific antibodies, either in one or both arms. These exchanges include for example VH-CH1 with VL-CL, VH with VL, CH3 with CL and CH3 with CH1 as described in Int. Patent Publ. Nos. WO2009/080254, WO2009/080251, WO2009/018386 and WO2009/080252.

Other strategies such as promoting heavy chain heterodimerization using electrostatic interactions by substituting positively charged residues at one CH3 surface and negatively charged residues at a second CH3 surface may be used to generate bispecific antibodies, as described in US Patent Publ. No. US2010/0015133; US Patent Publ. No. US2009/0182127; US Patent Publ. No. US2010/028637 or US Patent Publ. No. US2011/0123532. In other strategies, heterodimerization may be promoted by following substitutions (expressed as modified position in the first CH3 domain of the first heavy chain/modified position in the second CH3 domain of the second heavy chain): L351Y_F405A_Y407V/T394W, T366I_K392M_T394W/F405A_Y407V, T366L_K392M_T394W/F405A_Y407V, L351Y_Y407A/T366A_K409F, L351Y_Y407A/T366V_K409F, Y407A/T366A_K409F, or T350V_L351Y_F405A_Y407V/T350V_T366L_K392L_T394W as described in U.S. Patent Publ. No. US2012/0149876 or U.S. Patent Publ. No. US2013/0195849.

LUZ-Y technology may be utilized to generate bispecific antibodies. In this technology, a leucine zipper is added into the C terminus of the CH3 domains to drive the heterodimer assembly from parental mAbs that is removed post-purification as described in (Wranik et al. (2012) *J Biol Chem* 287: 43331-9).

SEEDbody technology may be utilized to generate bispecific antibodies. SEEDbodies have, in their constant domains, select IgG residues substituted with IgA residues to promote heterodimerization as described in U.S. Patent No. US20070287170.

Bispecific antibodies may be generated in vitro in a cell-free environment by introducing asymmetrical mutations in the CH3 regions of two monospecific homodimeric antibodies and forming the bispecific heterodimeric antibody from two parent monospecific homodimeric antibodies in reducing conditions to allow disulfide bond isomerization according to methods described in Int. Patent Publ. No. WO2011/131746 (DuoBody technology). In the methods, the first monospecific bivalent antibody and the second monospecific bivalent antibody are engineered to have certain substitutions at the CH3 domain that promoter heterodimer stability; the antibodies are incubated together under reducing conditions sufficient to allow the cysteines in the hinge region to undergo disulfide bond isomerization; thereby generating the bispecific antibody by Fab arm exchange. The incubation conditions may optimally be restored to non-reducing. Exemplary reducing agents that may be used are 2-mercaptoethylamine (2-MEA), dithiothreitol (DTT), dithioerythritol (DTE), glutathione, tris(2-carboxyethyl) phosphine (TCEP), L-cysteine and beta-mercaptoethanol. For example, incubation for at least 90 min at a temperature of at least 20° C. in the presence of at least 25 mM 2-MEA or in the presence of at least 0.5 mM dithiothreitol at a pH of from 5-8, for example at pH of 7.0 or at pH of 7.4 may be used.

Antibody domains and numbering are well known. "Asymmetrical" refers to non-identical substitutions in the two CH3 domains in two separate heavy chains in an antibody. An IgG1 CH3 region typically consists of residues 341-446 on IgG1 (residue numbering according to the EU index).

The antibodies of the invention may be engineered into various well known antibody forms.

Pharmaceutical Compositions/Administration

The invention provides for pharmaceutical compositions comprising the antibodies of the invention and a pharmaceutically acceptable carrier. For therapeutic use, the antibodies of the invention may be prepared as pharmaceutical compositions containing an effective amount of the antibody as an active ingredient in a pharmaceutically acceptable carrier. "Carrier" refers to a diluent, adjuvant, excipient, or vehicle with which the antibody of the invention is administered. Such vehicles may be liquids, such as water and oils, including those of petroleum, animal, vegetable or synthetic origin, such as peanut oil, soybean oil, mineral oil, sesame oil and the like. For example, 0.4% saline and 0.3% glycine may be used. These solutions are sterile and generally free of particulate matter. They may be sterilized by conventional, well-known sterilization techniques (e.g., filtration). The compositions may contain pharmaceutically acceptable auxiliary substances as required to approximate physiological conditions such as pH adjusting and buffering agents, stabilizing, thickening, lubricating and coloring agents, etc. The concentration of the antibodies of the invention in such pharmaceutical formulation may vary, from less than about 0.5%, usually to at least about 1% to as much as 15 or 20% by weight and may be selected primarily based on required dose, fluid volumes, viscosities, etc., according to the particular mode of administration selected. Suitable vehicles and formulations, inclusive of other human proteins, e.g., human serum albumin, are described, for example, in e.g. Remington: The Science and Practice of Pharmacy, 21st Edition, Troy, D. B. ed., Lipincott Williams and Wilkins, Philadelphia, Pa. 2006, Part 5, Pharmaceutical Manufacturing pp 691-1092, See especially pp. 958-989.

The mode of administration for therapeutic use of the antibodies of the invention may be any suitable route that delivers the antibody to the host, such as parenteral administration, e.g., intradermal, intramuscular, intraperitoneal, intravenous or subcutaneous, pulmonary, transmucosal (oral, intranasal, intravaginal, rectal), using a formulation in a tablet, capsule, solution, powder, gel, particle; and contained in a syringe, an implanted device, osmotic pump, cartridge, micropump; or other means appreciated by the skilled artisan, as well known in the art. Site specific administration may be achieved by for example intratumoral, intrarticular, intrabronchial, intraabdominal, intracapsular, intracartilaginous, intracavitary, intracelial, intracerebellar, intracerebroventricular, intracolic, intracervical, intragastric, intrahepatic, intracardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravascular, intravesical, intralesional, vaginal, rectal, buccal, sublingual, intranasal, or transdermal delivery.

The antibodies of the invention may be administered to a subject by any suitable route, for example parentally by intravenous (i.v.) infusion or bolus injection, intramuscularly or subcutaneously or intraperitoneally. i.v. infusion may be given over for example 15, 30, 60, 90, 120, 180, or 240 minutes, or from 1, 2, 3, 4, 5, 6, 7, 8, 9, 10, 11 or 12 hours.

The dose given to a subject is sufficient to alleviate or at least partially arrest the disease being treated ("therapeutically effective amount") and may be sometimes 0.005 mg to about 100 mg/kg, e.g. about 0.05 mg to about 30 mg/kg or about 5 mg to about 25 mg/kg, or about 4 mg/kg, about 8 mg/kg, about 16 mg/kg or about 24 mg/kg, or for example about 1, 2, 3, 4, 5, 6, 7, 8, 9 or 10 mg/kg, but may even higher, for example about 15, 16, 17, 18, 19, 20, 21, 22, 23, 24, 25, 30, 40, 50, 60, 70, 80, 90 or 100 mg/kg.

A fixed unit dose may also be given, for example, 50, 100, 200, 500 or 1000 mg, or the dose may be based on the patient's surface area, e.g., 500, 400, 300, 250, 200, or 100 mg/m$^2$. Usually between 1 and 8 doses, (e.g., 1, 2, 3, 4, 5, 6, 7 or 8) may be administered to treat the patient, but 9, 10, 11, 12, 13, 14, 15, 16, 17, 18, 19, 20 or more doses may be given.

The administration of the antibodies of the invention may be repeated after one day, two days, three days, four days, five days, six days, one week, two weeks, three weeks, one month, five weeks, six weeks, seven weeks, two months, three months, four months, five months, six months or longer. Repeated courses of treatment are also possible, as is chronic administration. The repeated administration may be at the same dose or at a different dose. For example, the antibodies of the invention described herein may be administered at 8 mg/kg or at 16 mg/kg at weekly interval for 8 weeks, followed by administration at 8 mg/kg or at 16 mg/kg every two weeks for an additional 16 weeks, followed by administration at 8 mg/kg or at 16 mg/kg every four weeks by intravenous infusion.

For example, the antibodies in the methods of the invention may be provided as a daily dosage in an amount of about 0.1-100 mg/kg, such as 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively, at least one of week 1, 2, 3, 4, 5, 6, 7, 8, 9, 10, 11, 12, 13, 14, 15, 16, 17, 18, 19 or 20 after initiation of treatment, or any combination thereof, using single or divided doses of every 24, 12, 8, 6, 4, or 2 hours, or any combination thereof.

The antibodies in the methods of the invention may also be administered prophylactically to reduce the risk of developing cancer, delay the onset of the occurrence of an event in cancer progression, and/or reduce the risk of recurrence when a cancer is in remission.

The antibodies of the invention may be lyophilized for storage and reconstituted in a suitable carrier prior to use. This technique has been shown to be effective with conventional protein preparations and well known lyophilization and reconstitution techniques can be employed.

Methods and Uses

The antibodies of the invention have in vitro and in vivo diagnostic, as well as therapeutic and prophylactic utilities. For example, the antibodies of the invention may be administered to cells in culture, in vitro or ex vivo, or to a subject to treat, prevent, and/or diagnose a variety of disorders, such as cancers and infectious disorders.

The invention also provides for a method of enhancing an agonistic activity of an anti-TNFR superfamily member in a subject, comprising introducing an E345R mutation, an E430G mutation, an E345R/E430G mutation or an E345R/E430G/S440Y mutation into the antibody to generate an engineered antibody specifically binding the receptor of TNFR family, and administering the engineered antibody to the subject for a time sufficient to enhance the agonistic activity.

The invention also provides for a method of enhancing an agonistic activity of an anti-TNFR superfamily member in a subject, comprising introducing an E345R mutation, an E430G mutation, an E345R/E430G mutation or an E345R/E430G/S440Y mutation into the antibody to generate an engineered antibody specifically binding the receptor of TNFR family, and administering the engineered antibody to the subject.

The invention also provides for a method of treating a cancer in a subject, comprising administering to the subject an antibody specifically binding a receptor of TNFR family comprising an E345R mutation, an E430G mutation, an E345R/E430G mutation or an E345R/E430G/S440Y for a time sufficient to treat the cancer.

The invention also provides for a method of treating a cancer in a subject, comprising administering to the subject an anti-TNFR superfamily antibody comprising an E345R mutation, an E345R/E430G mutation or an E345R/E430G/S440Y for a time sufficient to treat the cancer.

In the methods of the invention, the antibody mediates ADCC.

In the methods of the invention, the antibody mediates ADCP.

In the methods of the invention, the antibody enhances the agonistic activity of an anti-TNFR superfamily member independent of antibody cross-linking.

In the methods of the invention, the antibody optionally further comprises a second mutation (s) that reduces ADCC.

In the methods of the invention, the subject has a viral infection.

In the method of the invention, the subject has a cancer.

In the methods of the invention, the cancer is a solid tumor.

In the methods of the invention, the solid tumor is a melanoma, a lung cancer, a squamous non-small cell lung cancer (NSCLC), a non-squamous NSCLC, a colorectal cancer, a prostate cancer, a castration-resistant prostate cancer, a stomach cancer, an ovarian cancer, a gastric cancer, a liver cancer, a pancreatic cancer, a thyroid cancer, a squamous cell carcinoma of the head and neck, a carcinoma of the esophagus or gastrointestinal tract, a breast cancer, a fallopian tube cancer, a brain cancer, an urethral cancer, a genitourinary cancer, an endometriosis, a cervical cancer or a metastatic lesion of the cancer.

In the methods of the invention, the TNFR is tumor necrosis factor receptor 1 (SEQ ID NO: 1), tumor necrosis factor receptor 2 (SEQ ID NO: 2), lymphotoxin beta receptor (SEQ ID NO: 3), OX40 (SEQ ID NO: 4), CD40 (SEQ ID NO: 5), Fas receptor (SEQ ID NO: 6), decoy receptor 3 (SEQ ID NO: 7), CD27 (SEQ ID NO: 8), CD30 (SEQ ID NO: 9), CD137 (SEQ ID NO: 10), death receptor 4 (SEQ ID NO: 11), death receptor 5 (SEQ ID NO: 12), decoy receptor 1 (SEQ ID NO: 13), decoy receptor 2 (SEQ ID NO: 14), RANK (SEQ ID NO: 15), osteoprotegerin (SEQ ID NO: 16), TWEAK receptor (SEQ ID NO: 17), TACI (SEQ ID NO: 18), BAFF receptor (SEQ ID NO: 19), herpesvirus entry mediator (SEQ ID NO: 20), nerve growth factor receptor (SEQ ID NO: 21), B-cell maturation antigen (SEQ ID NO: 22), GITR (SEQ ID NO: 23), TROY (SEQ ID NO: 24), death receptor 6 (SEQ ID NO: 25), death receptor 3 (SEQ ID NO: 26) or ectodysplasin A2 receptor (SEQ ID NO: 27).

In the methods of the invention, the TNFR is OX40 (SEQ ID NO: 4), CD27 (SEQ ID NO: 8), CD40 (SEQ ID NO: 5), CD137 (SEQ ID NO: 10), or GITR (SEQ ID NO: 23).

In the methods of the invention, the TNFR is OX40 (SEQ ID NO: 4).

In the methods of the invention, the TNFR is CD27 (SEQ ID NO: 8).

In the methods of the invention, the TNFR is CD40 (SEQ ID NO: 5).

In the methods of the invention, the TNFR is CD137 (SEQ ID NO: 10).

In the methods of the invention, the TNFR is GITR (SEQ ID NO: 23).

Many of the TNFR superfamily members and their ligands have been implicated as targets for cancer therapy, including TNFR1/2/TNF-α, CD70/CD27/CD27, CD137/4-1BB, OX40/OX40L, CD40/CD40L, GITR/GITRL (Bremer, Hindawi Publishin Corporation ISRN oncology Volume 2013, Article ID 371854, 25 pages; Sanmamed et al), and several agonistic antibodies targeting the TNFR superfamily members, such as anti-CD40, anti-OX-40, anti-GITR, anti-CD27, anti-CD137 antibodies are in clinical development for various solid tumors as well as heme malignancies such as non-Hodking's lymphoma and B-cell malignancies. It can be expected that anti-CD40, anti-OX40, anti-GITR, anti-CD27, anti-CD137 and other anti-TNFR superfamily member antibodies of the invention with improved properties in terms of their enhanced agonistic activity optionally coupled with effector functionality will be therapeutically effective in the treatment of various cancers, including solid tumors.

While having described the invention in general terms, the embodiments of the invention will be further disclosed in the following examples that should not be construed as limiting the scope of the claims.

Example 1. Fc Engineering Approach to Improve Agonistic Activity Anti-TNFR Superfamily Member Antibodies Agonistic antibodies directed against immunostimulatory receptors belonging to the tumor necrosis factor receptor (TNFR) superfamily are emerging as promising drug candidates for cancer immunotherapies. Several Fc engineering approaches were discovered recently that can augment the anti-tumor activities of anti-TNFR antibodies by enhancing their agonistic activities and/or effector functions.

Monoclonal antibodies that stimulate antitumor immunity are emerging as an important class of cancer therapeutics (Mellman et al. (2011) *Nature* 480: 480-9; Chen et al. (2013) *Nat Rev Immunol* 13: 227-42). The antibodies targeting the immune checkpoint receptors CTLA-4 and PD-1 have been approved as monotherapies for advanced melanoma, lung cancer and evaluated for the treatment of other types of human cancer. Besides targeting the inhibitory pathways, agonist antibodies directed against the immunostimulatory receptors on T cells and antigen presenting cells also can stimulate antitumor immunity and are emerging as a promising area of clinical development for cancer immunotherapies (Schaer et al. (2014) *J Immunother Cancer* 2: 7).

Many immunostimulatory receptors belong to the tumor necrosis factor (TNF) receptor superfamily. Of them, OX40, CD27, 4-1BB and GITR are expressed on effector T cells and their ligands and agonist antibodies can activate these receptors to stimulate the proliferation and activation of T cells (Kanamaru et al. (2004) *J Immunol* 172: 7306-14; Gramaglia et al. (1998) *J Immunol* 161: 6510-7; Pollok et al. (1993) *J Immunol* 150: 771-81; Ramakrishna et al. (2015) *J Immunother Cancer* 3: 37). CD40 is expressed on antigen presenting cells and the activation of this receptor facilitates more efficacious presentation of tumor antigens to activated T cells (Mangsbo et al. (2015) *Clin Cancer Res* 21: 1115-26). Many evidences indicated that the agonistic activities of therapeutic antibodies to these TNF receptors are important for their anti-tumor activities (Mangsbo et al. (2015) *Clin Cancer Res* 21: 1115-26; He et al. (2013) *J Immunol* 191: 4174-83; Wilson et al. (2011) *Cancer Cell* 19: 101-13). On the other hand, several TNFR superfamily members, such as OX40 and GITR, have elevated expression on regulatory T cells ($T_{reg}$) which negatively modulate tumor immunity. Several studies have revealed that the anti-OX40 and anti-GITR antibodies may facilitate the selective elimination of regulatory T cells in tumor microenvironment by the effector functions of the antibody (Bulliard et al. (2013) *J Exp Med* 210: 1685-93; Bulliard et al. (2014) *Immunol Cell Biol* 92: 475-80). Such antibody-mediated killing of regulatory T cells may be more important than the antibody-mediated activation of effector T cells for the anti-tumor activities of therapeutic anti-OX40 and anti-GITR antibodies.

Accumulating evidences indicated that immunomodulatory antibodies engage different types of Fc receptors for their agonistic activities and effector functions. To activate downstream signaling pathways, TNFR trimerization is required. However, one antibody molecule commonly is not enough to cluster enough TNF receptors; instead, antibody crosslinking is necessary for receptor activation in in vitro assays (Morris et al. (2007) *Mol Immunol* 44: 3112-21. Recent studies in mice indicated that the engagement to the inhibitory FcγRIIB receptor is critical for the agonistic activity of antibodies to a number of TNFR targets, including CD40 (Li et al. (2011) *Science* 333: 1030-4; White et al. (2013) *Cancer Immunol Immunother* 62: 941-8), death receptor 5 (DRS) (Wilson et al. (2011) *Cancer Cell* 19: 101-13; Li et al. (2012) *Proc Natl Acad Sci USA* 109: 10966-71) and CD95 (Xu et al. (2003) *J Immunol* 171: 562-8). The crosslinking of IgG Fc to FcγRIIB receptors can multimerize more than one antibody molecule, which in turn can facilitate the clustering of enough TNFR for signaling pathway activation. On the other hand, the antibody effector functions, such as ADCC and ADCP, depend on the interactions with various activating Fcγ receptors. Studies in mice revealed that activating Fcγ receptors contribute to the antitumor activities of immunomodulatory anti-OX40 and anti-GITR antibodies by selectively eliminating intratumoral regulatory T cells (Bulliard et al. (2013) *J Exp Med* 210: 1685-93; (Bulliard et al. (2014) *Immunol Cell Biol* 92: 475-80).

Human IgG antibodies have poor binding affinities to the majority of human Fc receptors except FcγRI (Guilliams et al. (2014) *Nat Rev Immunol* 14: 94-108). To optimize the antitumor activity of agonist antibodies for immunostimulatory TNF receptors, one approach is to engineer the Fc region of the IgG antibody to improve its Fcγ receptor engagement, particularly the engagement with FcγRIIB receptor which mediates the agonism of TNF receptor antibodies. In this regard, Chu et al. described S267E/L328F mutations in IgG1 Fc with enhanced FcγRIIB binding affinity (Chu et al. (2008) *Mol Immunol* 45: 3926-33. Anti-CD19 antibody engineered with such mutations showed improved inhibition of B cell receptor-mediated activation of primary human B cells. However, further study revealed that such Fc variant also has enhanced binding to R131 allotype of the activating FcγRIIA receptor (Mimoto et al. (2013) *Protein Eng Des Sel* 26: 589-98. Recently, Mimoto et al. reported a set of six mutations in IgG1 Fc, collectively named as V12 mutations, with selectively enhanced FcγRIIB engagement without associated increased binding to either H131 or R131 allotype of FcγRIIA receptor (Mimoto et al. (2013) *Protein Eng Des Sel* 26: 589-98. Anti-CD137 agonistic antibody with the engineered V12 mutation showed much enhanced agonistic activity dependent on FcγRIIB engagement.

Although optimizing FcγRIIB engagement is a viable approach, the agonistic activity of such engineered antibody depends heavily on the Fcγ receptor expression in the local microenvironment and the efficacy of such antibody may be limited to the anatomical site of action. In an effort to augment the agonism of immunostimulatory antibodies independent of Fcγ receptor engagement, White et al. recently reported that human IgG2 can impart superagonistic activity to immunostimulatory antibodies for CD40, 4-1BB and CD28 receptors (White et al. (2015) *Cancer Cell* 27: 138-48). This activity is conferred by a unique configuration of disulfide bonds in the hinge region of the IgG2 subtype and is not dependent on FcγRIIB engagement. On the other hand, if the purpose of crosslinking to FcγRIIB is solely to increase the clustering of agonistic antibodies for receptor activation, then we hypothesized those Fc mutations that can promote antibody multimerization may enhance the agonism of antibodies to TNF receptors without the need of FcγRIIB crosslinking. Diebolder et al. reported that selective Fc mutations can facilitate IgG antibody into the formation of a hexamer upon binding targets on cell surface (Diebolder et al. (2014) *Science* 343: 1260-3). While it was reported that such IgG hexamer can greatly activate complement-dependent cytotoxicity (CDC), we present claims for another application that oligomerized antibodies that recognize TNF receptors may activate such receptors by promoting receptor clustering.

This work describes evaluation of different Fc engineering approaches on the enhancement of the agonism of an anti-OX40 antibody. Besides, the effects of Fc mutations on the ADCC and ADCP effector functions of the engineered antibodies were also evaluated. Such study may help to guide the design of engineered antibodies to OX40 and other TNF receptors with improved anti-tumor activity.

Example 2. Materials and Methods

Fc Engineering of Anti-OX40 Antibody

The VH and the VL regions of an anti-OX40 antibody SF2 (VH: SEQ ID NO: 51, VL: SEQ ID NO: 52) was cloned onto human wild type IgG1 or IgG2 and select substitutions were engineered onto the Fc to evaluate the effect of the substitutions on agonistic activity of the antibody and effector functions. The names of the generated antibodies and their Fc substitutions are shown in Table 3.

TABLE 3

| Antibody name | Isotype | Fc mutations (residue numbering according to the EU Index) |
|---|---|---|
| OX40SF2IgG1 | IgG1 | Wild-type |
| OX40SF2IgG2 | IgG2 | Wild-type |
| OX40SF2IgG2sigma | IgG2 | V234A, G237A, P238S, H268A, V309L, A330S, P331S |
| OX40SF2IgG1S267E/L328F | IgG1 | S267E and L328F |
| OX40SF2IgG1V12 | IgG1 | E233D, G237D, P238D, H268D, P271G, A330R |
| OX40SF2IgG1E345R | IgG1 | E345R |
| OX40SF2IgG1E430G | IgG1 | E430G |
| OX40SF2IgG1E345R/E430G | IgG1 | E345R and E430G |
| OX40SF2IgG1E345R/E430G/S440Y | IgG1 | E345R, E430G and S440Y |
| OX40SF2IgG2sigmaE345R | IgG2 | V234A, G237A, P238S, H268A, V309L, A330S, P331S, E345R |

IgG1 with E345R mutation

SEQ ID NO: 63

```
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPRRPQVYTLPPSREEMTKNQVSLTC

LVKGFYPSDIAVEWESNGQPENNYKTTPPVLDSDGSFFLYSKLTVDKSRW

QQGNVFSCSVMHEALHNHYTQKSLSLSPGK
```

IgG1 with E430G mutation

SEQ ID NO: 64

```
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSREEMTKNQVSLTC

LVKGFYPSDIAVEWESNGQPENNYKTTPPVLDSDGSFFLYSKLTVDKSRW

QQGNVFSCSVMHGALHNHYTQKSLSLSPGK
```

IgG1 with E345R/E430G mutation

SEQ ID NO: 65

```
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPRRPQVYTLPPSREEMTKNQVSLTC

LVKGFYPSDIAVEWESNGQPENNYKTTPPVLDSDGSFFLYSKLTVDKSRW

QQGNVFSCSVMHGALHNHYTQKSLSLSPGK
```

IgG1 with E345R/E430G/S440Y mutation

SEQ ID NO: 66

```
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPELLGGPSVFLFPPKPKDTLMISRTPEVTCVVVDVS
```

-continued

```
HEDPEVKFNWYVDGVEVHNAKTKPREEQYNSTYRVVSVLTVLHQDWLNGK

EYKCKVSNKALPAPIEKTISKAKGQPRRPQVYTLPPSREEMTKNQVSLTC

LVKGFYPSDIAVEWESNGQPENNYKTTPPVLDSDGSFFLYSKLTVDKSRW

QQGNVFSCSVMHGALHNHYTQKYLSLSPGK
```

IgG2sigma with E345R mutation

SEQ ID NO: 67

```
ASTKGPSVFPLAPCSRSTSESTAALGCLVKDYFPEPVTVSWNSGALTSGV

HTFPAVLQSSGLYSLSSVVTVPSSNFGTQTYTCNVDHKPSNTKVDKTVER

KCCVECPPCPAPPAAASSVFLFPPKPKDTLMISRTPEVTCVVVDVSAEDP

EVQFNWYVDGVEVHNAKTKPREEQFNSTFRVVSVLTVLHQDWLNGKEYKC

KVSNKGLPSSIEKTISKTKGQPRRPQVYTLPPSREEMTKNQVSLTCLVKG

FYPSDIAVEWESNGQPENNYKTTPPMLDSDGSFFLYSKLTVDKSRWQQGN

VFSCSVMHEALHNHYTQKSLSLSPGK
```

Antibody Expression and Purification

Plasmids encoding antibody heavy chains (HC) and light chains (LC) were co-transfected at a 1:3 (HC: LC) molar ratio into Expi293F cells following the transfection kit instructions (Life Technologies). Cells were spun down five days post transfection and the supernatant were passed through a 0.2 μm filter. The titer of antibody expression was quantified using Octet (ForteBio). Antibody purification was carried out using prepacked Protein A spin columns following the kit instruction (GE Healthcare Life Sciences). The purified antibody was buffer-exchanged into DPBS, pH7.2 by dialysis and protein concentration was determined by UV absorbance at 280 nm. Quality and integrity of the molecules was assessed by high-performance size-exclusion chromatography (HP-SEC) and SDS-PAGE of reduced and non-reduced samples.

NanoBRET Protein-Protein Interaction Assay

The coding sequence for the light chain of anti-OX40 SF2 antibody was cloned into pNLF-C and pHTC halotag vectors (Promega, Madison, Wis.) in frame with C-terminal Nanoluc and Halotag sequences respectively. These light chains were paired with the heavy chains for OX40SF2IgG1, OX40SF2IgG1E345R, OX40SF2IgG1E345R/E430G, and OX40SF2IgG1E345R/E430G/S440Y antibodies to express Fc engineered SF2 antibodies with either Nanoluc or Halotag attached at the C-termini of the light chains Standard Protein A spin column were employed to purify these modified antibodies.

To study antibody multimerization on the cell surface by the NanoBRET protein-protein interaction assay (Promega, Madison, Wis.), $0.25\times10^5$ HEK-Blue: OX40 cells were seeded in each well of the 96-well assay plate and cultured at 37° C. overnight. The next day, equal concentrations of Nanoluc-tagged antibody (donor) and Halotag-tagged antibody (acceptor) in 50 μl assay medium (Opti-MEM I reduced serum medium, no phenol red plus 4% FBS) were applied to the cells. Halotag 618 ligand diluted 1:1000 in 50 μl assay medium were added in experimental well, and a no ligand control well was also set up by diluting DMSO 1:1000 in assay medium. After incubation at 37° C. for 30 min, the cells were washed twice with assay medium and resuspended in 100 μl assay medium. 25 μl Nano-Glo substrate, diluted 1:200 in assay medium without FBS, was added to each well. After shaking for 30 seconds, the donor emission (460 nm) and acceptor emission (618 nm) were measured by Envision. Raw NanoBRET ratio values with milliBRET units (mBU) were calculated as RawBRET=618 $nm_{Em}$/460 $nm_{Em}$*1000. To factor in donor-contributed background or bleed through, Corrected NanoBRET ratio values with milliBRET units was calculated as CorrectedBRET=$RawBRET_{experimental\ sample}$−$RawBRET_{no\text{-}ligand\ control\ sample}$, which reflects energy transfer from a bioluminescent protein donor to a fluorescent protein acceptor due to protein-protein interactions.

Flow Cytometry Staining

Plasmids expressing cDNAs encoding human FcγRI (NM_000566) (SEQ ID NO: 59), FcγRIIA (NM_021642) (SEQ ID NO: 60), FcγRIIB (NM_004001) (SEQ ID NO: 61), and FcγRIIIA (NM_000569) (SEQ ID NO: 62) (Origene) were transiently transfected into Expi293F cells by Expifectmine293 transfection kit (Life Technologies). Flow cytometry assays were performed 48 h after transfection. To confirm the expression of transfected Fc receptors, their specific antibodies, 10.1 (BD Pharmingen) for FcγRI, IV.3 (StemCell Technologies) for FcγRIIA, 2B6 (in house preparation) for FcγRIIB (Veri et al. (2007) *Immunology* 121: 392-404, and 3G8 (BD Pharmingen) for FcγRIIIA, were employed in flow cytometry staining as positive controls. Raji cells (ATCC: CCL-86) were also employed to test the binding of anti-OX40 antibody to FcγRIIB receptor.

$2\times10^5$ cells per well were seeded in 96-well plate and blocked in BSA Stain Buffer (BD Biosciences, San Jose, USA) for 30 min at 4° C. Cells were incubated with test antibody on ice for 1.5 hour at 4° C. After being washed twice with BSA stain buffer, the cells were incubated with R-PE labeled anti-human or anti-mouse IgG secondary antibody (Jackson Immunoresearch Laboratories) for 45 min at 4° C. The cells were washed twice in stain buffer and then resuspended in 150 μL of Stain Buffer containing 1:200 diluted DRAQ7 live/dead stain (Cell Signaling Technology, Danvers, USA). PE and DRAQ7 signals of the stained cells were detected by Miltenyi MACSQuant flow cytometer (Miltenyi Biotec, Auburn, USA) using B2 and B4 channel respectively. Live cells were gated on DRAQ7 exclusion and the geometric mean fluorescence signals were determined for at least 10,000 live events collected. FlowJo software (Tree Star) was used for analysis. Data was plotted as the logarithm of antibody concentration versus mean fluorescence signals. Nonlinear regression analysis was performed by GraphPad Prism 6 (GraphPad Software, Inc.) and $EC_{50}$ values were calculated.

SEQ ID NO: 59

```
MWFLTTLLLWVPVDGQVDTTKAVITLQPPWVSVFQEETVTLHCEVLHLPG
SSSTQWFLNGTATQTSTPSYRITSASVNDSGEYRCQRGLSGRSDPIQLEI
HRGWLLLQVSSRVFTEGEPLALRCHAWKDKLVYNVLYYRNGKAFKFFHWN
SNLTILKTNISHNGTYHCSGMGKHRYTSAGISVTVKELFPAPVLNASVTS
PLLEGNLVTLSCETKLLLQRPGLQLYFSFYMGSKTLRGRNTSSEYQILTA
RREDSGLYWCEAATEDGNVLKRSPELELQVLGLQLPTPVWFHVLFYLAVG
IMFLVNTVLWVTIRKELKRKKKWDLEISLDSGHEKKVISSLQEDRHLEEE
LKCQEQKEEQLQEGVHRKEPQGAT
```

SEQ ID NO: 60

```
MTMETQMSQNVCPRNLWLLQPLTVLLLLASADSQAAPPKAVLKLEPPWIN
VLQEDSVTLTCQGARSPESDSIQWFHNGNLIPTHTQPSYRFKANNNDSGE
YTCQTGQTSLSDPVHLTVLSEWLVLQTPHLEFQEGETIMLRCHSWKDKPL
```

-continued

```
VKVTFFQNGKSQKFSHLDPTFSIPQANHSHSGDYHCTGNIGYTLFSSKPV
TITVQVPSMGSSSPMGIIVAVVIATAVAAIVAAVVALIYCRKKRISANST
DPVKAAQFEPPGRQMIAIRKRQLEETNNDYETADGGYMTLNPRAPTDDDK
NIYLTLPPNDHVNSNN
```

SEQ ID NO: 61

```
MGILSFLPVLATESDWADCKSPQPWGHMLLWTAVLFLAPVAGTPAAPPKA
VLKLEPQWINVLQEDSVTLTCRGTHSPESDSIQWFHNGNLIPTHTQPSYR
FKANNNDSGEYTCQTGQTSLSDPVHLTVLSEWLVLQTPHLEFQEGETIVL
RCHSWKDKPLVKVTFFQNGKSKKFSRSDPNFSIPQANHSHSGDYHCTGNI
GYTLYSSKPVTITVQAPSSSPMGIIVAVVTGIAVAAIVAAVVALIYCRKK
RISALPGYPECREMGETLPEKPANPTNPDEADKVGAENTITYSLLMHPDA
LEEPDDQNRI
```

SEQ ID NO: 62

```
MAEGTLWQILCVSSDAQPQTFEGVKGADPPTLPPGSFLPGPVLWWGSLAR
LQTEKSDEVSRKGNWWVTEMGGGAGERLFTSSCLVGLVPLGLRISLVTCP
LQCGIMWQLLLPTALLLLVSAGMRTEDLPKAVVFLEPQWYRVLEKDSVTL
KCQGAYSPEDNSTQWFHNESLISSQASSYFIDAATVDDSGEYRCQTNLST
LSDPVQLEVHIGWLLLQAPRWVFKEEDPIHLRCHSWKNTALHKVTYLQNG
KGRKYFHHNSDFYIPKATLKDSGSYFCRGLFGSKNVSSETVNITITQGLA
VSTISSFFPPGYQVSFCLVMVLLFAVDTGLYFSVKTNIRSSTRDWKDHKF
KWRKDPQDK
```

HEK-Blue NFkB Reporter Assay

A stable HEK-Blue reporter cell line expressing human OX40 (HEK-Blue: OX40) was established by transfection OX40 expression plasmid (pUNO1-hOX40) into HEK-Blue™ Null 1 cells engineered to express a secreted embryonic alkaline phosphatase (SEAP) reporter gene under the control of NF-κB-inducible promoter (IFN-β minimal promoter). For the reporter assay, $1\times10^5$ HEK-Blue: OX40 cells resuspended in 200 μl culture media were aliquoted in each well of the 96-well assay plate and the OX40 ligand or anti-OX40 antibodies were added. To test the crosslinking effect, either 1 μl of protein G magnetic beads (Pierce) or $1\times10^5$ Raji cell was added in the same assay well. After incubation at 37° C. overnight, the agonistic activities of the antibodies were evaluated by the quantification of the induced secreted alkaline phosphatase (SEAP) reporter gene expression using Quanti-Blue detection kit (Invivogen). Briefly, 40 μl cell culture supernatant was mixed with 160 μl Quanti-Blue reagent and incubated at 37° C. until appropriate blue color developed. The OD at 650 nm was measured using a SpectraMax microplate reader (Molecular Devices, Sunnyvale, Calif.). The agonistic activity of anti-OX40 antibody was normalized as percent activity relative to that induced by 1 μg/ml OX40 ligand.

ADCC Assay

The ADCC activities of anti-OX40 antibodies were evaluated by an ADCC reporter bioassay as instructed by the manufacturer (Promega). Briefly, 25,000 HEK-Blue: OX40 cells per well plated in 96-well plate overnight were mixed with the engineered effector cells in which the activation of FcγRIIIA receptor leads to the expression of a luciferase reporter. Anti-OX40 antibodies were added to the cells and incubated at 37° C. for 6 h. Then Bio-Glo luciferase reagent was added and the luciferase signals were quantitated by Envision. The ADCC activities of anti-OX40 antibody were expressed as fold of activation of luciferase signals over that without testing antibody added.

ADCP Assay

An OX40 target cell line expressing GFP was established by infection HEK-Blue: OX40 cells with a Turbo GFP transduction particle (Sigma Aldrich). Stable GFP-expressing cells were selected with puromycin. The human $CD14^+$ $CD16^+$ monocytes were isolated from PBMCs (Biologics Specialty) using a negative human monocyte enrichment kit without CD16 depletion (StemCell Technologies). Isolated monocytes were plated in X-VIVO-10 medium (Lonza) containing 10% FBS and macrophages were differentiated from monocytes by the addition of 25 ng/ml macrophage colony-stimulating factor (R&D Systems) for 7 days. IFNγ (50 ng/ml; R&D Systems) was added for the final 24 h of differentiation. For the ADCP assay, $1\times10^5$ cells/well differentiated macrophages were mixed with $0.25\times10^5$ cells/well GFP-expressing HEK-Blue: OX40 cells (4:1 ratio) in 200 μl medium (DMEM+10% FBS) in 96-well U-bottom plates. The test antibodies were added and the plate was incubated in a 37° C. incubator for 24 h. Then the cells were detached using Accutase (Sigma) and resuspended in BSA Stain Buffer. Macrophages were stained with anti-CD11b and anti-CD14 antibodies (BD Biosciences) coupled to Alexa Fluor 647 (Invitrogen). GFP positive HEK-Blue: OX40 target cells and Alexa647 positive macrophages were identified by flow cytometry using Miltenyi MACSQuant flow cytometer (Miltenyi Biotec, Auburn, USA). The data were analyzed using FlowJo software (Tree Star) and ADCP-mediated cell killing was determined by measuring the reduction in GFP fluorescence using the following equation: Percentage of target cells killed=((Percentage of $GFP^+$, $CD11b^-$, $CD14^-$ cells with the lowest concentration of antibody)−(Percentage of $GFP^+$, $CD11b^-$, $CD14^-$ cells with the test concentration of antibody))/(Percentage of $GFP^+$, $CD11b^-$, $CD14^-$ cells with the lowest concentration of antibody)×100.

CDC Assay

The CDC activities of anti-OX40 antibodies were evaluated by a complement-mediated cell killing assay. Briefly, $1\times10^5$ HEK-Blue:OX40 cells were incubated with 6.7% (v/v) rabbit complement (Cedar Lane Labs, Burlington, Canada) and testing antibodies for 1 h. The lactate dehydrogenase activity released from the cytosol of lysed HEK-Blue:OX40 cells into the supernatant were measured by a Cytotoxicity Detection Kit according to manufacturer's instructions (Roche Diagnostics, Indianapolis, Ind.). The complement-mediated cytotoxicity was expressed as percent cytotoxicity relative to that lysed by 0.67% (v/v) Triton X-100.

Example 3. Establishment of an NFκB Reporter Assay for the Assessment of the Agonism of Anti-OX40 Antibody OX40, a member of TNF receptor superfamily, activates nuclear factor kappaB (NFkB) signaling pathway by binding to TNF receptor-associated factors (TRAF). To study the contributions of Fc engineering on the agonistic activity of OX40 antibodies, a HEK-Blue™ reporter cell line stably expressing human OX40 and SEAP under NFκB inducible promoter was established. OX40 ligand dose-dependently activated the transfected OX40 receptor that leads to SEAP reporter gene expression (FIG. 1A). OX40SF2IgG1 antibody was then evaluated for its agonistic activity by this reporter assay. While the antibody alone showed little agonistic activity, OX40SF2IgG1 antibody immobilized on protein G beads can stimulated reporter gene expression in a dose-dependent manner and to a level better than OX40 ligand at 1000 ng/ml (FIG. 1A), indicating that antibody crosslinking is needed for the agonistic activity.

Figure 1B:
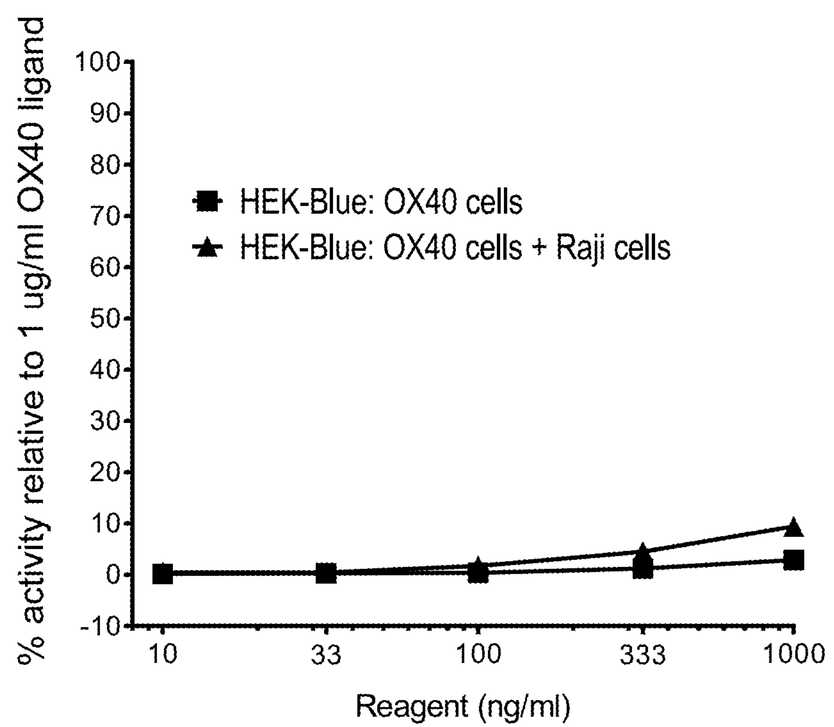
FIG. 1B shows that co-culturing with Raji cells fails to significantly enhance the agonistic activity of SF2 antibody with native human IgG1 Fc. Increasing concentrations (10 to 1000 ng/mL) of OX40SF2IgG1 antibody were incubated with HEK-Blue: OX40 cells with or without co-culturing with Raji cells and their agonistic activities were assessed by HEK-Blue NF-κB reporter assay. The agonistic activities of anti-OX40 antibodies, normalized as percent activity relative to that driven by 1 μg/mL OX40 ligand, were plotted against the concentrations of test antibodies (Data were presented as mean±SEM, n=14).

Recent studies revealed that FcγRIIB can provide the crosslinking activity and facilitate the agonistic activity of TNF receptor antibodies (Li et al. (2012) *Cell Cycle* 11: 3343-4). The FcγRIIB crosslinking effect was assessed in the reporter assay by co-culturing HEK-Blue: OX40 cells with human B lymphoblastoid Raji cells, on which FcγRIIB is predominantly expressed (Rankin et al. (2006) *Blood* 108: 2384-91). However, co-culturing with Raji cells failed to significantly enhance the agonistic activity of SF2 antibody with native IgG1 (FIG. 1B).

Example 4. Characterization of Anti-OX40 Antibodies with S267E/L328F and V12 Mutations S267E/L328F mutations and E233D/G237D/P238D/H268D/P271G/A330R mutations (referred to as V12 mutations herein) in antibody Fc have been identified to enhanced binding of the antibodies to FcγRIIB receptor. To evaluate the effects of such mutations on anti-OX40 antibody, an anti-OX-40 antibody SF2 was cloned as IgG1 with S267E/L328F double mutations (OX40SF2IgG1S267E/L328F) and the V12 mutations (OX40SF2IgG1V12).

Binding to FcγR

Figure 2A:
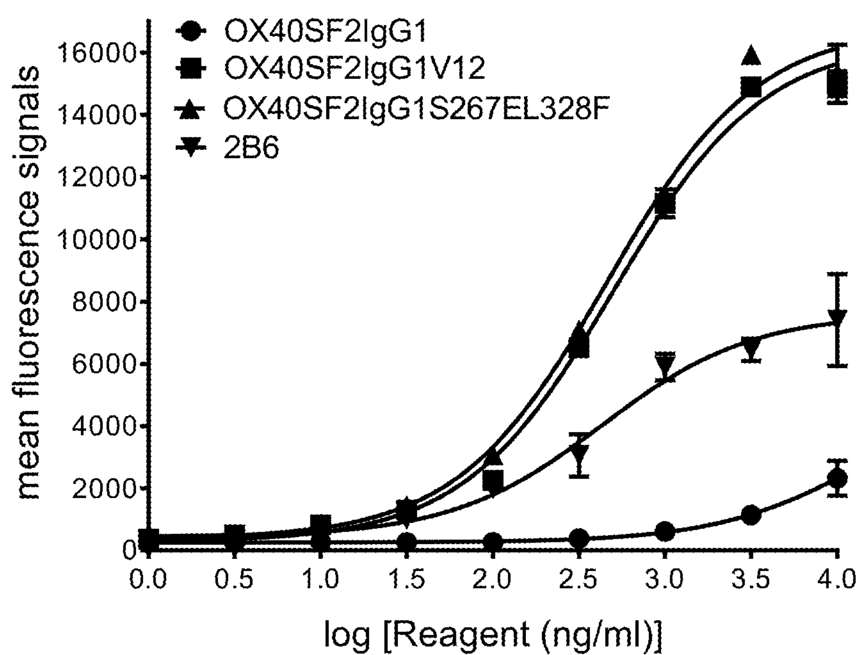
FIG. 2A shows that OX40SF2IgG1S267E/L328F and OX40SF2IgG1V12 have enhanced binding to FcγRIIB when compared to the wild-type IgG1 (OX40SF2IgG1). Expi293F cells expressing FcγRIIB were incubated with increasing concentrations (1 ng/ml to 10000 ng/ml) of OX40SF2IgG1, OX40SF2IgG1S267E/L328F and OX40SF2IgG1V12, and binding of the antibodies were assessed using flow cytometry. Mean fluorescence signals were plotted vs. concentrations of test antibodies. Data are presented as mean±SEM, n=2
Figure 2B:
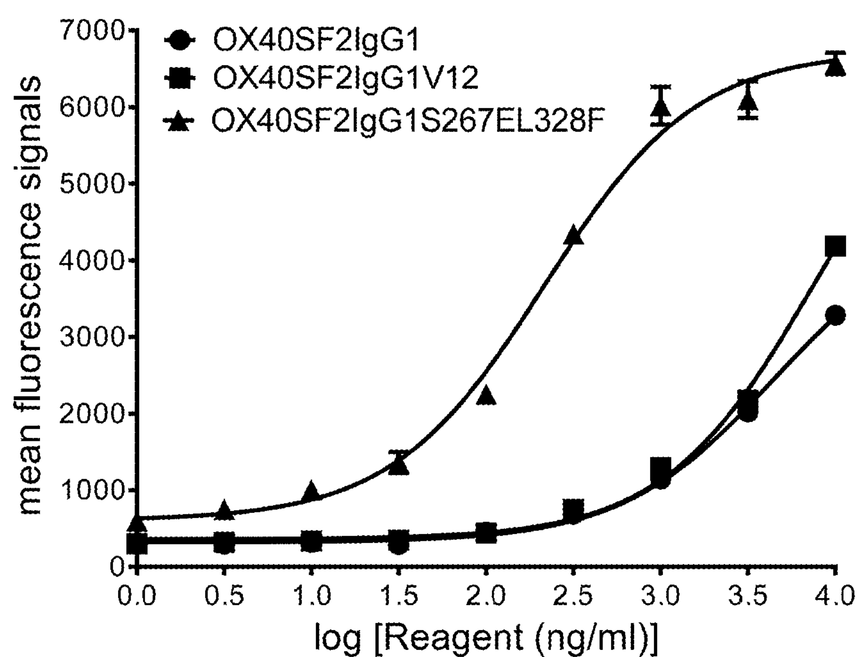
FIG. 2B shows that OX40SF2IgG1S267E/L328F has enhanced binding to FcγRIIA when compared to the wild-type IgG1 (OX40SF2IgG1), whereas OX40SF2IgG1V12 had comparable binding. Expi293F cells expressing FcγRIIA were incubated with increasing concentrations (1 ng/ml to 10000 ng/ml) of OX40SF2IgG1, OX40SF2IgG1S267E/L328F and OX40SF2IgG1V12, and binding of the antibodies were assessed using flow cytometry. Mean fluorescence signals were plotted vs. concentrations of test antibodies. Data are presented as mean±SEM, n=2

The binding of engineered antibodies to various FcγR expressed on transiently-transfected Expi293F cells were assessed by flow cytometry. For FcγRIIB, while OX40SF2 antibody with native IgG1 has poor binding, the engineered Fc mutations potently facilitate anti-OX40 antibody with increased binding affinity to FcγRIIB with $EC_{50}$ (459 ng/ml for OX40SF2IgG1S267E/L328F and 502 ng/ml for OX40SF2IgG1V12) comparable to 2B6 (431 ng/ml), an antibody preferentially recognizes FcγRIIB, and much better than that of OX40SF2IgG1 (FIG. 2A). Similar flow cytometry assays were performed to assess the binding of engineered anti-OX40 antibodies to R131 allotype of FcγRIIA expressed on transiently-transfected Expi293F cells. While OX40SF2IgG1V12 showed poor binding to FcγRIIA similarly as OX40SF2IgG1, the S267E/L328F mutations facilitate more potent binding to $FcγRIIA^{R131}$ ($EC_{50}$: 216 ng/ml) with 20-fold better potency (FIG. 2B). This data is consistent to previous finding that both S267E/L328F and V12 mutations facilitate enhanced FcγRIIB binding while the effect of V12 mutations is more specific.

Figure 2C:
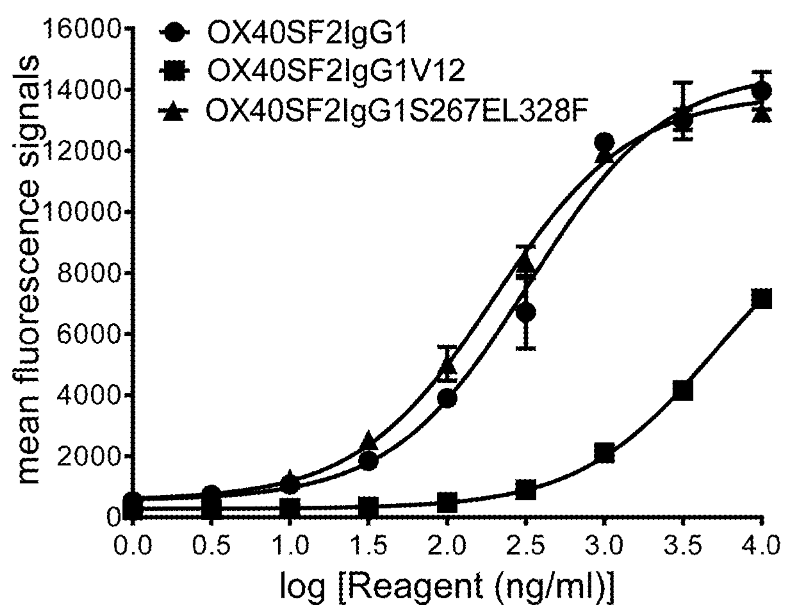
FIG. 2C shows that OX40SF2IgG1V12 has reduced binding to FcγRI when compared to the wild-type IgG1 (OX40SF2IgG1), whereas OX40SF2IgG1S267E/L328F had comparable binding. Expi293F cells expressing FcγRI were incubated with increasing concentrations (1 ng/ml to 10000 ng/ml) of OX40SF2IgG1, OX40SF2IgG1S267E/L328F and OX40SF2IgG1V12, and binding of the antibodies were assessed using flow cytometry. Mean fluorescence signals were plotted vs. concentrations of test antibodies. Data are presented as mean±SEM, n=2
Figure 2D:
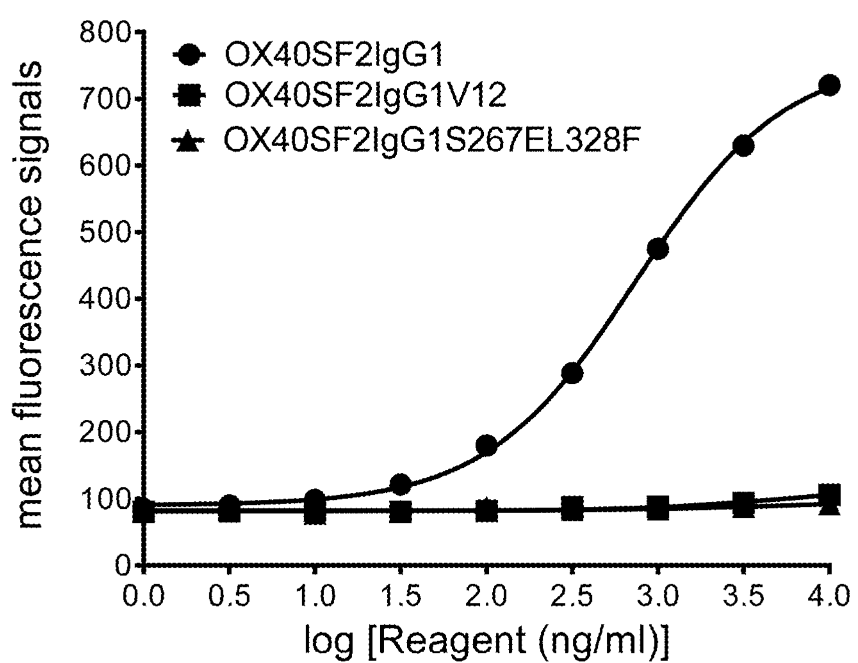
FIG. 2D shows that OX40SF2IgG1S267E/L328F and OX40SF2IgG1V12 have abolished binding to FcγRIIIA. Expi293F cells expressing FcγRIIIA were incubated with increasing concentrations (1 ng/ml to 10000 ng/ml) of OX40SF2IgG1, OX40SF2IgG1S267E/L328F and OX40SF2IgG1V12, and binding of the antibodies were assessed using flow cytometry. Mean fluorescence signals were plotted vs. concentrations of test antibodies. Data are presented as mean±SEM, n=2

For FcγRI, OX40SF2IgG1 showed high affinity with an $EC_{50}$ at 326 ng/ml (FIG. 2C). The OX40SF2IgG1S267E/L328F antibody showed similar binding property as OX40SF2IgG1, however, the V12 mutations significantly abrogate the binding of OX40SF2IgG1V12 antibody to FcγRI. The binding of the engineered anti-OX40 antibodies to FcγRIIIA receptor were also evaluated by flow cytometry assay. While OX40SF2IgG1 antibody showed binding to FcγRIIIA with an $EC_{50}$ of 744 ng/ml, OX40SF2IgG1S267E/L328F and OX40SF2IgG1V12 showed no binding activities to FcγRIIIA (FIG. 2D).

Agonism

Figure 3A:
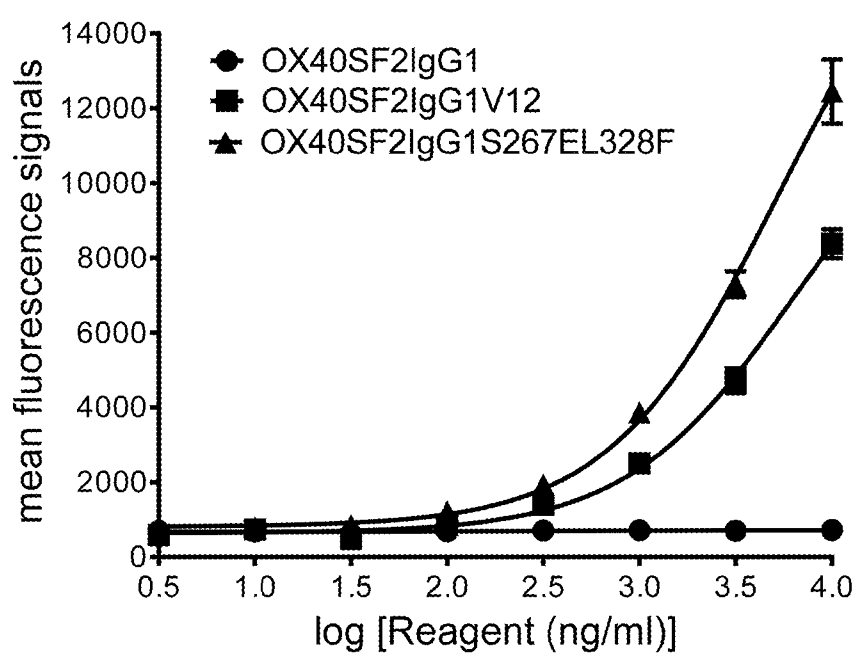
FIG. 3A shows that OX40SF2IgG1S267E/L328F and OX40SF2IgG1V12 have enhanced binding to Raji cells expressing FcγRIIB receptors when compared to the wild-type IgG1 (OX40SF2IgG1). Increasing concentrations (3 ng/ml to 10000 ng/ml) of OX40SF2IgG1, OX40SF2IgG1S267E/L328F and OX40SF2IgG1V12 were assessed for their binding to Raji cells by flow cytometry assay. Mean fluorescence signals were plotted vs. concentrations of test antibodies. Data are presented as mean±SEM, n–3.
Figure 3B:
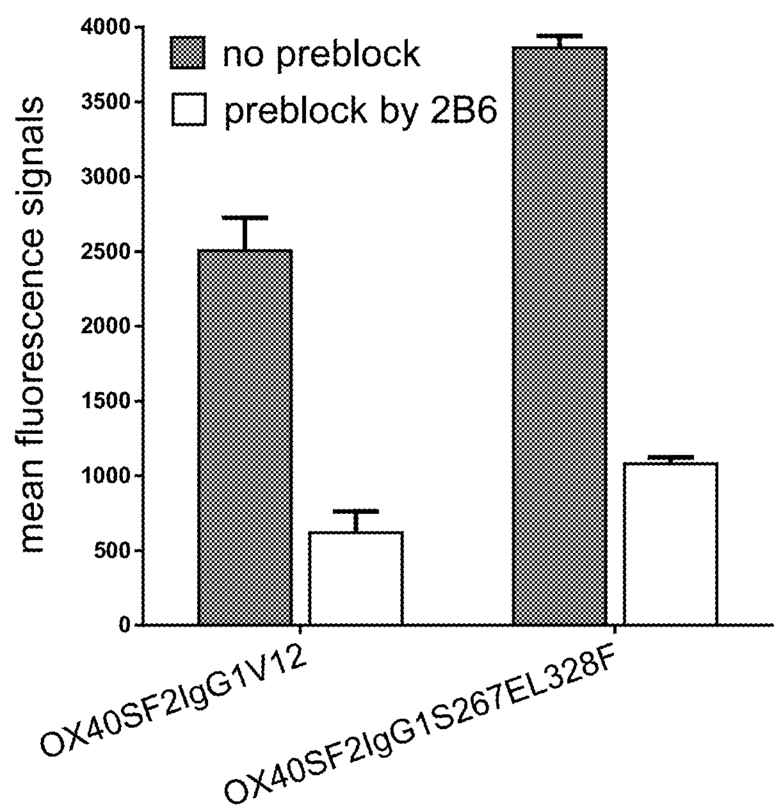
FIG. 3B shows that binding of OX40SF2IgG1S267E/L328F and OX40SF2IgG1V12 to Raji cells is FcγRIIB dependent. Raji cells were pretreated with 5 μg/ml of anti-FcγRIIB antibody 2B6 and the binding of 1 μg/ml of antibodies to Raji cells were assessed by flow cytometry. Mean fluorescence signals of binding with or without preblock by the 2B6 antibody as indicated are presented in the bar graphs as mean±SEM, n=3.

Since S267E/L328F and V12 mutations facilitate OX40SF2IgG1 antibody with increased binding affinity to FcγRIIB, it was assessed whether these enhanced binding may lead to increased agonism of anti-OX40 antibody by the HEK-Blue NFκB reporter assay. First, the binding of engineered anti-OX40 antibodies to Raji cells were assessed by flow cytometry assay. OX40SF2IgG1S267E/L328F and OX40SF2IgG1V12, but not OX40SF2IgG1, showed dose-dependent binding to Raji cells (FIG. 3A), albeit with less potency compared to Expi293F cells transfected with FcγRIIB receptor (FIG. 2A). To confirm the binding to Raji cells are mediated by FcγRIIB, Raji cells were pre-treated with 5 μg/ml of 2B6 antibody before assessing the binding of engineered anti-OX40 antibody to Raji cells. It was observed that pre-block of FcγRIIB on Raji cells by 2B6 antibody significantly abrogated the binding of OX40SF2IgG1S267E/L328F and OX40SF2IgG1V12 to Raji cells (FIG. 3B).

Figure 3C:
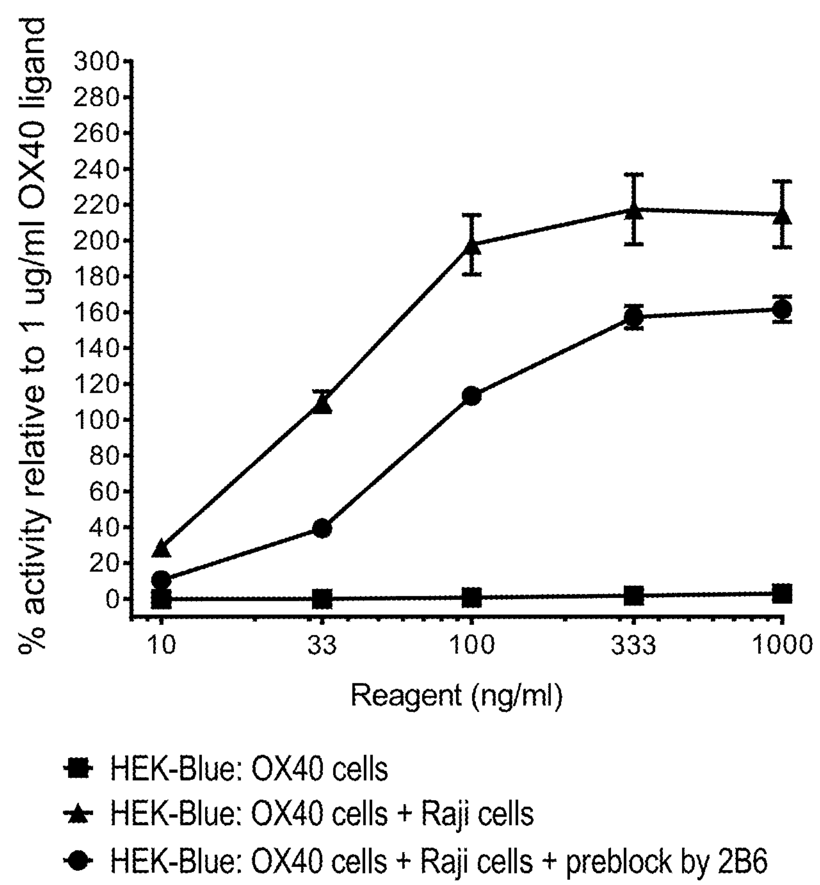
FIG. 3C shows that the agonistic activity of OX40SF2IgG1S267E/L328F is dependent on antibody cross-linking by FcγRIIB on Raji cells. Increasing concentrations (10 ng/ml to 1000 ng/ml) of OX40SF2IgG1S267E/L328F were incubated with HEK-Blue™ cells stably expressing OX40 with or without co-culture with Raji cells which were in some assays pre-incubated with 5 μg/ml of the anti-FcγRIIB antibody 2B6 antibody before initiation of the co-cultures. The y axis shows the agonistic activity of anti-OX40 antibodies normalized as percent activity mediated by 1 m/ml OX40 ligand. Data are presented as mean±SEM, n≥6.
Figure 3D:
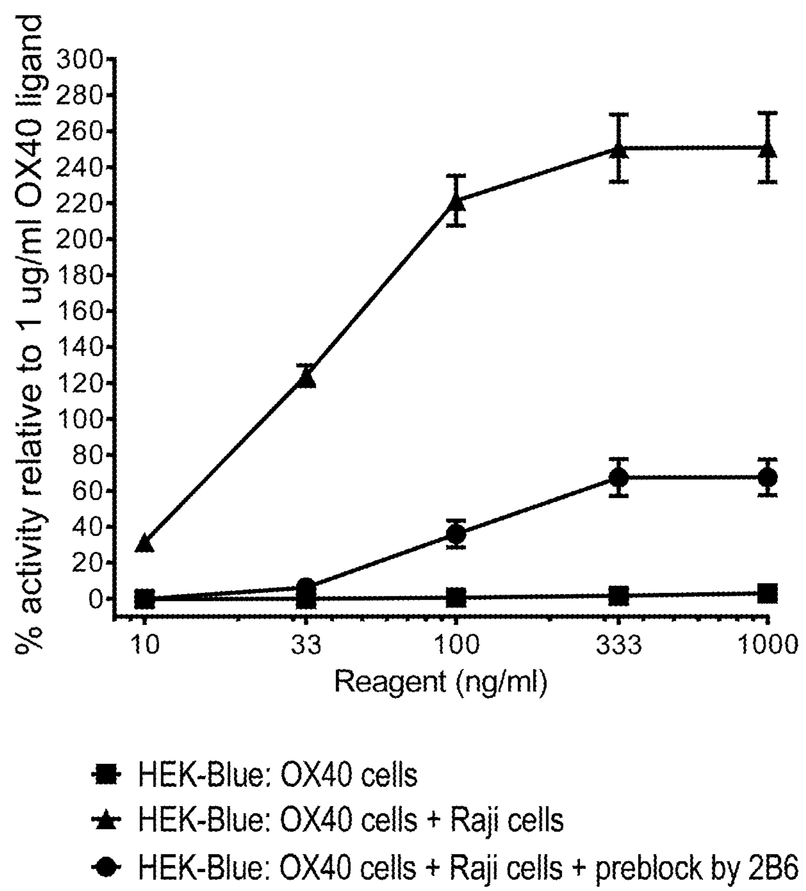
FIG. 3D shows that the agonistic activity of OX40SF2IgG1V12 is dependent on antibody cross-linking by FcγRIIB on Raji cells. Increasing concentrations (10 ng/ml to 1000 ng/ml) of OX40SF2IgG1V12 were incubated with HEK-Blue™ cells stably expressing OX40 with or without co-culture with Raji cells which were in some assays pre-incubated with 5 μg/ml of the anti-FcγRIIB (2B6) antibody before initiation of the co-cultures. The y axis shows the agonistic activity of anti-OX40 antibodies normalized as percent activity mediated by 1 m/ml OX40 ligand. Data are presented as mean±SEM, n≥6.

In HEK-Blue™ NFκB reporter assay, neither OX40SF2IgG1S267E/L328F nor OX40SF2IgG1V12 showed significant agonistic activity in the absence of Raji cells. However, with Raji cells and HEK-Blue: OX40 cells co-cultured, these engineered anti-OX40 antibodies showed dramatically increased agonism, with over two-fold better efficacy at 1000 ng/ml compared to OX40 ligand at the same concentration (FIG. 3C and FIG. 3D). Besides, when 2B6 antibody was added to pre-block FcγRIIB on Raji cells, the Raji cell-dependent enhancement of agonism for OX40SF2IgG1S267E/L328F and OX40SF2IgG1V12 antibodies were significantly abrogated (FIG. 3C and FIG. 3D), implying that the agonistic activities of the engineered antibody were mediated by FcγRIIB crosslinking.

Fc Effector Functions

Figure 4A:
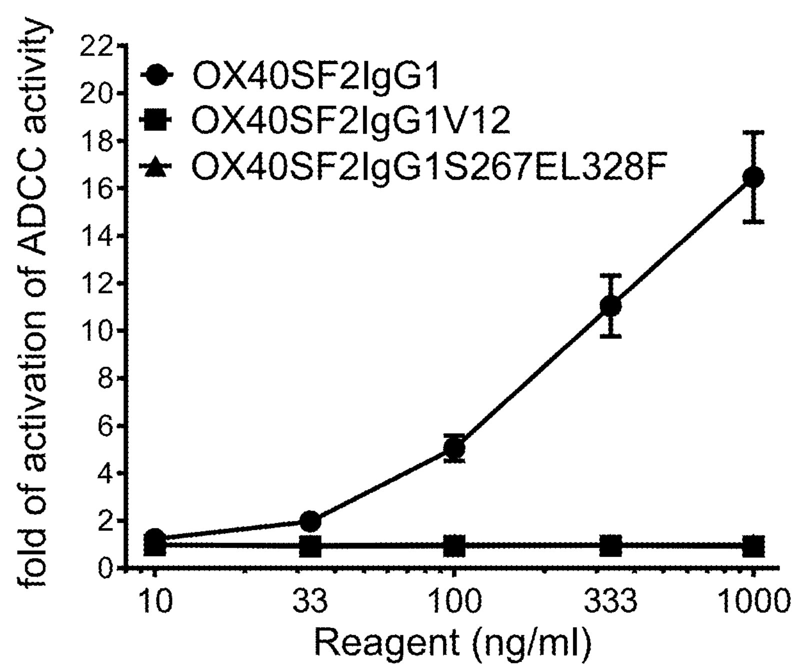
FIG. 4A shows that OX40SF2IgG1V12 and OX40SF2IgG1S267E/L328F have abolished ADCC. Increasing concentrations (10 ng/ml to 1000 ng/ml) of OX40SF2IgG1S267E/L328F, OX40SF2IgG1V12 and OX40SF2IgG1 were incubated with HEK-Blue™ cells stably expressing OX40 co-cultured with effectors cells and ADCC reporter bioassays were performed. The fold activation (over the control sample without an antibody added) of ADCC activities were plotted vs. concentrations of test antibodies. Data are presented as mean±SEM, n≥6.

The ADCC activities of the anti-OX40 antibodies with S267E/L328F and V12 mutations were studied by a reporter bioassay, in which the bioluminescent reporter gene expression in effector cells reflects FcγRIIIA-mediated ADCC activation. When HEK-Blue: OX40 target cells were co-cultured with effector cells expressing FcγRIIIA, OX40SF2IgG1 dose-dependently activated reporter gene expression. However, neither OX40SF2IgG1S267E/L328F nor OX40SF2IgG1V12 induced reporter gene expression (FIG. 4A), indicating that the S267E/L328F and V12 mutations abrogated the ADCC activity of OX40SF2IgG1 antibody. This result is consistent with the loss of binding activities to FcγRIIIA for the engineered antibodies (FIG. 2D).

Figure 4B:
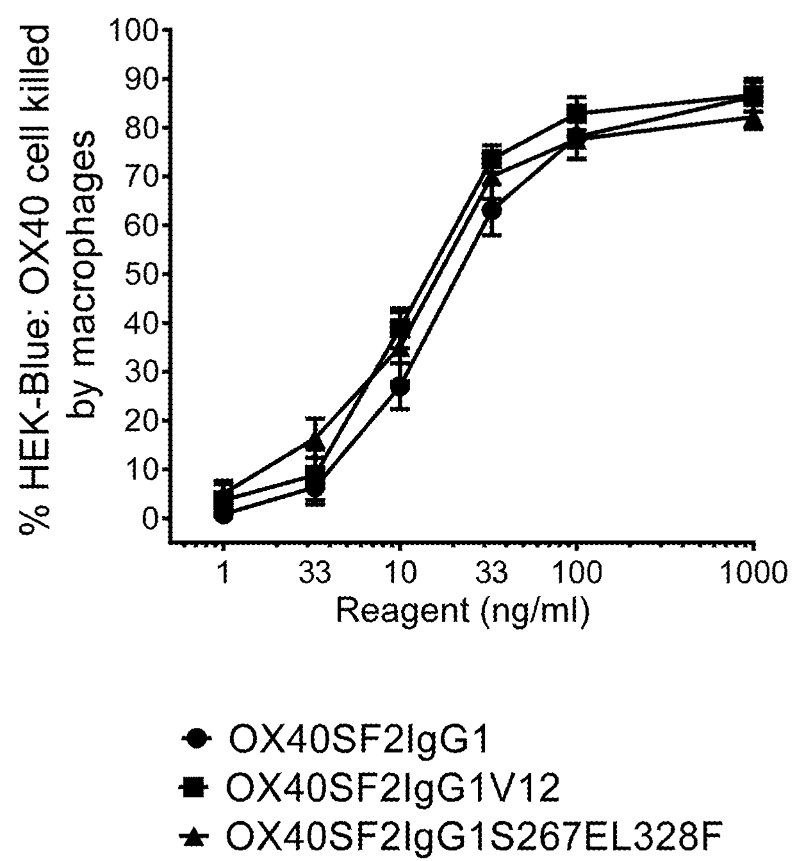
FIG. 4B shows that OX40SF2IgG1V12 and OX40SF2IgG1S267E/L328F retain their ADCP activity. Increasing concentrations (1 ng/ml to 1000 ng/ml) of OX40SF2IgG1S267E/L328F, OX40SF2IgG1V12 and OX40SF2IgG1 were incubated with GFP positive HEK-Blue™ cells stably expressing OX40 co-cultured with differentiated macrophages and the phagocytosis of GFP positive target cells were evaluated by flow cytometry assay. The percentages of GFP positive cells eliminated, which reflect the ADCP activities, were plotted vs. concentrations of test antibodies. Data are presented as mean±SEM, n≥6.
Figure 4C:
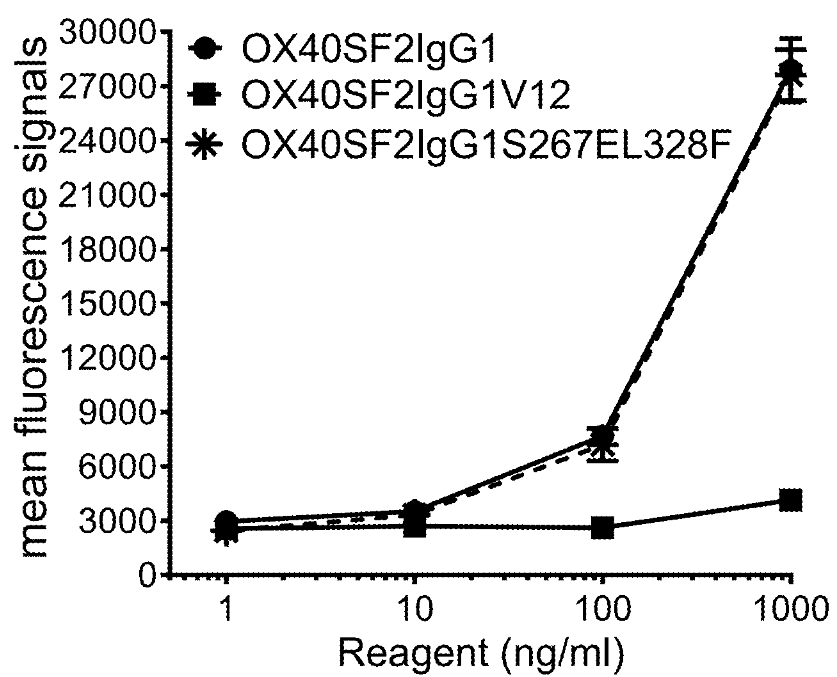
FIG. 4C shows that OX40SF2IgG1V12 has reduced binding to differentiated macrophages whereas OX40SF2IgG1S267E/L328F binds to macrophages at similar levels as the wild-type antibody (OX40SF2IgG1). Increasing concentrations (1 ng/ml to 1000 ng/ml) of OX40SF2IgG1, OX40SF2IgG1S267E/L328F and OX40SF2IgG1V12 antibodies were incubated with differentiated macrophages and their binding was assessed using flow cytometry assays. Mean fluorescence signals were plotted vs. concentrations of test antibodies. Data are presented as mean±SEM, n=2.

The antibody dependent cellular phagocytosis (ADCP) activities of the anti-OX40 antibodies with S267E/L328F and V12 mutations were also studied in an assay evaluating phagocytosis of GFP-expressed HEK-Blue: OX40 cells by macrophages differentiated from isolated monocytes. OX40SF2IgG1 antibody dose-dependently mediated killing of HEK-Blue: OX40 target cells by the macrophages. Neither the S267E/L328F nor the V12 mutation significantly altered the ADCP activity of OX40SF2IgG1 antibody (FIG. 4B). The binding of engineered anti-OX40 antibodies to differentiated macrophages were assessed by flow cytometry assay. While OX40SF2IgG1S267E/L328F antibody had similar binding affinity to macrophage with the OX40SF2IgG1 antibody, the OX40SF2IgG1V12 antibody, although active in ADCP assay, had significantly reduced binding to macrophage (FIG. 4C).

Figure 4D:
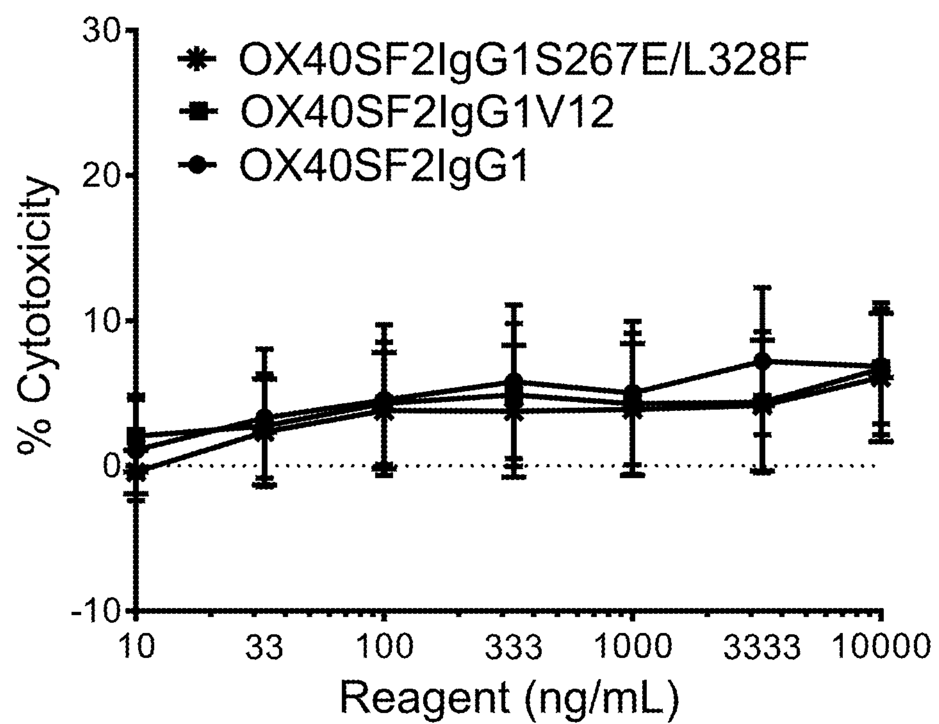
FIG. 4D shows that OX40SF2IgG1V12 and OX40SF2IgG1S267E/L328F do not mediate CDC. Increasing concentrations (10 to 10,000 ng/ml) of OX40SF2IgG1, OX40SF2IgG1S267E/L328F and OX40SF2IgG1V12 antibodies were incubated with HEK-Blue™ cells stably expressing OX40 in the presence of rabbit complement. The CDC activities were quantitated by measuring lactate dehydrogenase (LDH) activity released from the cytosol of lysed cells and expressed as percent cytotoxicity relative to that lysed by Triton X-100 (data were presented as mean±S.E., n=7).

Antibody-mediated CDC were studied in an assay evaluating lysis HEK-Blue: OX40 cells in the presence of rabbit complement. The OX40SF2IgG1 antibody did not lead to significant CDC activity toward HEK-Blue:OX40 target cells up to 10,000 ng/ml. Likewise, neither the V12 nor S267E/L328F mutations facilitated higher CDC activities relative to the antibody with the native human IgG1 Fc domain (FIG. 4D).

Example 5. Characterization of Anti-OX40 Antibodies with Singular or Combination E345R, E430G, and S440Y Mutations Diebolder et al. identified a set of Fc mutations (E345R, E430G, and S440Y) which induced hexamerization of IgG1 antibody when bound to cell surface antigen, and enhanced antibody effector functions ADCC and CDC (Diebolder et al. (2014) Science 343: 1260-3). It was hypothesized that such multimerized antibody may enhance the agonism of anti-TNFR superfamily antibody by facilitating the aggregation of TNFR superfamily member, which is a prerequisite for receptor activation.

To test the hypothesis, single E345R, E430G and S440Y mutations or the mutations in combination were engineered on anti-OX40 antibody SF2 on IgG1, and the resulting antibodies OX40SF2IgG1E345R, OX40SF2IgG1E430G, OX40SF2IgG1 E345R/E430G and OX40SF2IgG1 E345R/E430G/S440Y as shown in Table 3 were characterized.

Antibody Multimerization

SEC analysis revealed that OX40SF2IgG1E345R, OX40SF2IgG1E430G and OX40SF2IgG1E345R/E430G antibodies exist as monomers in solution, just as OX40SF2IgG1. However, SEC analyses revealed a ~900 kDa peak for the triple mutated antibody OX40SF2IgG1E345R/E430G/S440Y, indicating the presence of a hexamer for that antibody. This observation is consistent with the reported finding that E345R/E430G/S440Y mutations promote hexamer formation readily in solution phase (Diebolder et al. (2014) *Science* 343: 1260-3.

Figure 5:
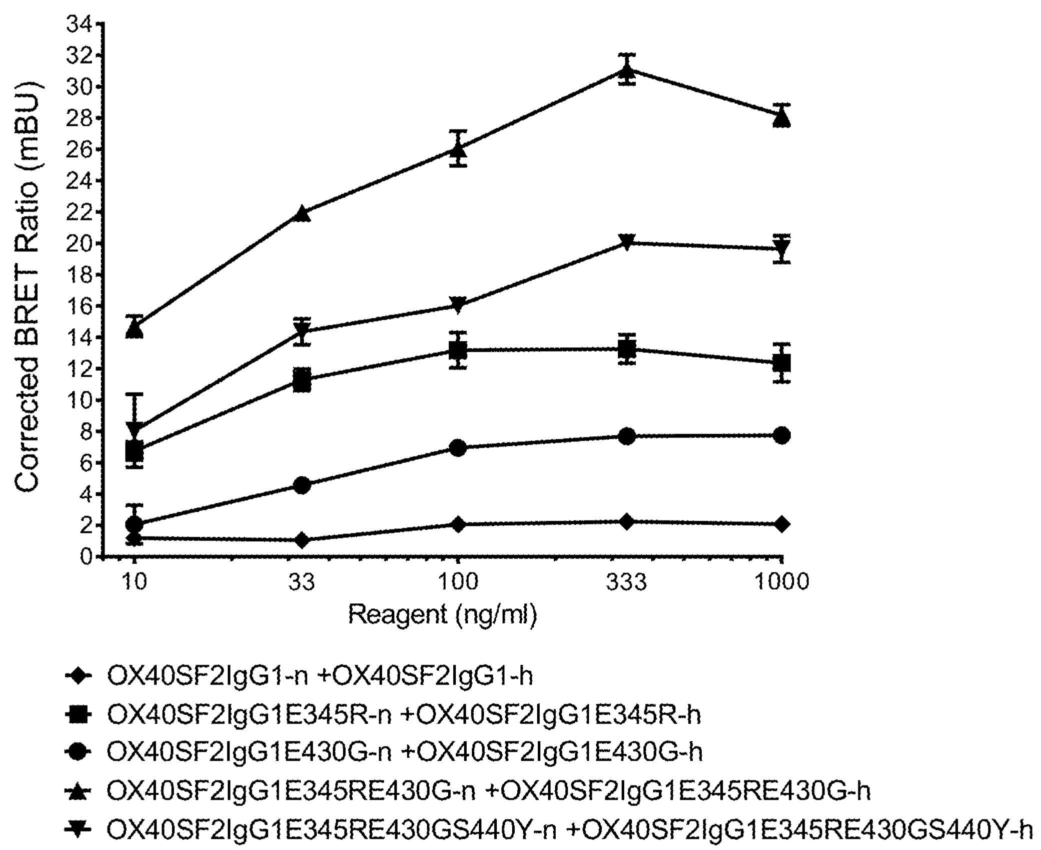
FIG. 5 shows the corrected bioluminescence resonance energy transfer (BRET) ratios obtained from the NanoBRET™ PPI assay for OX40SF2IgG1, OX40SF2IgG1E345R, OX40SF2IgG1E430G, OX40SF2IgG1E345R/E430G and OX40SF2IgG1E345R/E430G/S440Y, indicative of degree of antibody multimerization on the surface of OX40-expressing cell. OX40SF2IgG1-n, OX40SF2IgG1E345R-n, OX40SF2IgG1E430G-n, OX40SF2IgG1E345R/E430G-n, and OX40SF2IgG1E345R/E430G/S440Y-n are constructs that are in-frame with C-terminal Nanoluc sequences. OX40SF2IgG1-h, OX40SF2IgG1E345R-h, OX40SF2IgG1E430G-h, OX40SF2IgG1E345R/E430G-h, and OX40SF2IgG1E345R/E430G/S440Y-h are constructs that are in-frame with C-terminal Halotag sequences. Increasing concentrations (from 10 ng/ml to 1000 ng/ml) of both Nanoluc® donor antibody and Halo Tag® acceptor antibody were applied to HEK-Blue™ cells stabely expressing OX40 cells and NanoBRET PPI assays were conducted. The Mean Corrected BRET ratio were plotted vs. concentrations of test antibodies. Data are presented as mean±SEM, n≥2.

To evaluate whether the engineered antibodies multimerize upon binding antigens at the cell surface a NanoBRET™ protein-protein interaction (PPI) assay was conducted. This assay is a proximity-based assay that detects protein-protein interactions by measuring energy transfer from a bioluminescent protein donor to a fluorescent protein acceptor. The generated antibodies OX40SF2IgG1E345R, OX40SF2IgG1E430G, OX40SF2IgG1E345R/E430G and OX40SF2IgG1E345R/E430G/S440Y were further engineered to have either the Nanoluc® luciferase or the fluorescently labeled Halo Tag® attached to the C-terminus of antibody light chain as the donor and acceptor, respectively. The tagged antibodies showed comparable functional activities in HEK-Blue NFκB reporter assay as corresponding un-tagged antibodies (data not shown). NanoBRET PPI assays were performed by applying the donor and acceptor antibodies to HEK-Blue: OX40 cells and the calculated corrected NanoBRET ratios reflect the association of multimerized antibody. While OX40SF2IgG1 antibody demonstrated a background corrected NanoBRET ratio, SF2 antibodies with mutations that promote IgG hexamerization showed much higher corrected NanoBRET ratio across concentrations from 10 to 1000 ng/ml (FIG. 5). The degree of antibody association at the cell surface, reflected by the Corrected NanoBRET ratio value, was in the following order: OX40SF2IgG1E345R/E430G>OX40SF2IgG1E345R/E430G/S440Y>OX40SF2IgG1E345R>OX40SF2IgG1E430G>OX40SF2IgG1. The results indicated that all antibodies except wild-type IgG1 multimerized on the cell surface, albeit at different degree in association.

Improved Agonism of Engineered Anti-OX40 Antibodies is Independent of FcγRIIB Crosslinking The engineered antibodies were characterized in HEK-Blue™ NFκB reporter assay to evaluate the effect of E345R, E430G and S440Y substitutions on agonistic activity of the antibodies. All generated antibodies demonstrated agonistic activity. OX40SF2IgG1E345R demonstrated the most improved agonistic activity when compared to the activity of OX40 ligand (FIG. 6A) albeit that the antibody did not have the highest degree of multimerization (FIG. 5).

Figure 6A:
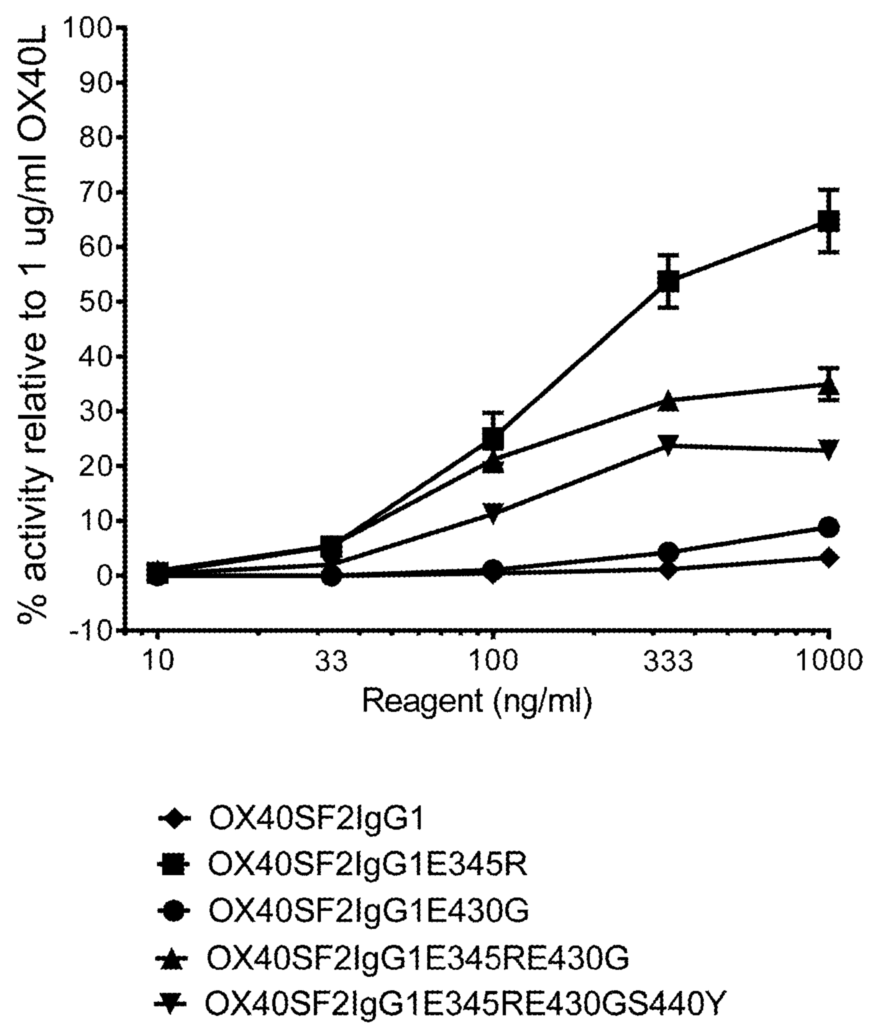
FIG. 6A shows enhanced agonistic activity of OX40SF2IgG1E345R, OX40SF2IgG1E430G, OX40SF2IgG1E345R/E430G and OX40SF2IgG1E345R/E430G/S440Y when compared to OX40SF2IgG1 in a HEK-Blue™ NFκB reporter assay. Increasing concentrations (10 ng/ml to 1000 ng/ml) of OX40SF2IgG1, OX40SF2IgG1E345R, OX40SF2IgG1E430G, OX40SF2IgG1E345R/E430G and OX40SF2IgG1E345R/E430G/S440Y antibodies were applied to HEK-Blue™ cells stably expressing OX40, and SEAP secretion was measured. The agonistic activity was normalized as percent activity relative to that driven by 1 μg/ml OX40 ligand and plotted vs. concentrations of test antibodies. Data are presented as mean±SEM, n≥9.

OX40SF2IgG1E430G demonstrated the least improved agonistic activity while OX40SF2IgG1 E345R/E430G and OX40SF2IgG1E345R/E430G/S440Y demonstrated degree of agonism between OX40SF2IgG1E345R and OX40SF2IgG1E430G (FIG. 6A).

Figure 6B:
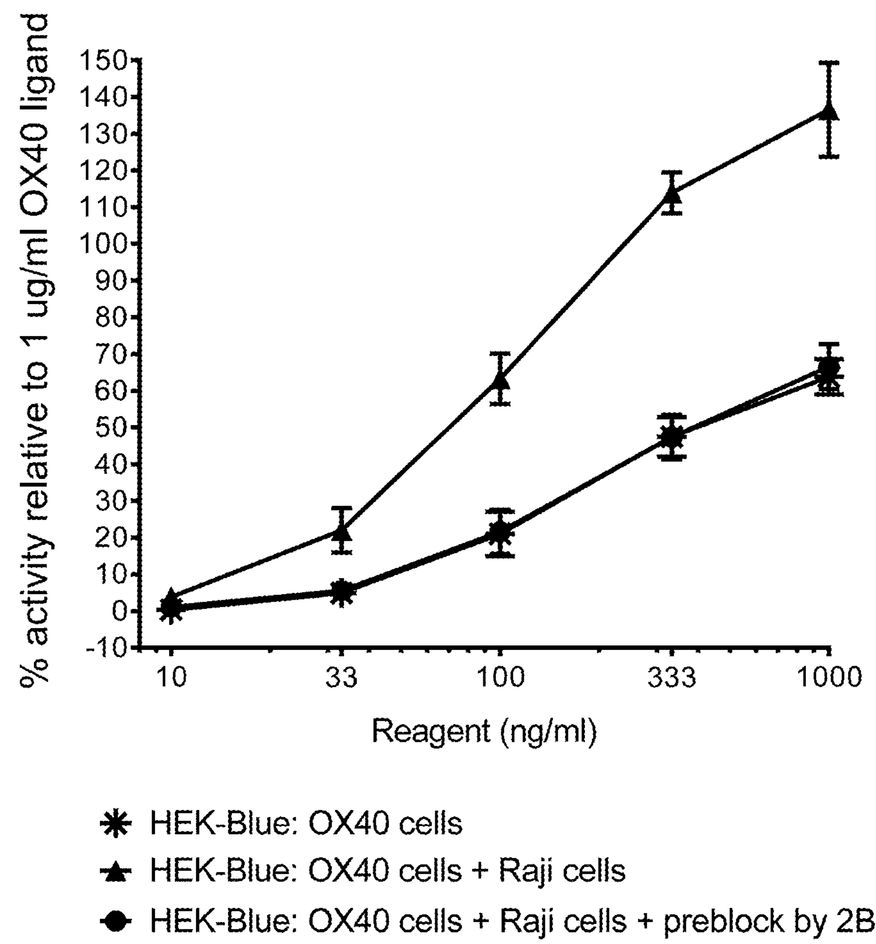
FIG. 6B shows that cross-linking of OX40SF2IgG1E345R with Raji cells further boosts the agonistic activity of the antibody in a HEK-Blue™ NFκB reporter assay. Pre-block of FcγRIIB on Raji cells by anti-FcγRIIB antibody 2B6 abrogated the boost. The agonistic activity was normalized as percent activity relative to that driven by 1 μg/ml OX40 ligand and plotted vs. concentrations of test antibodies. Data are presented as mean±SEM, n=3.
Figure 6C:
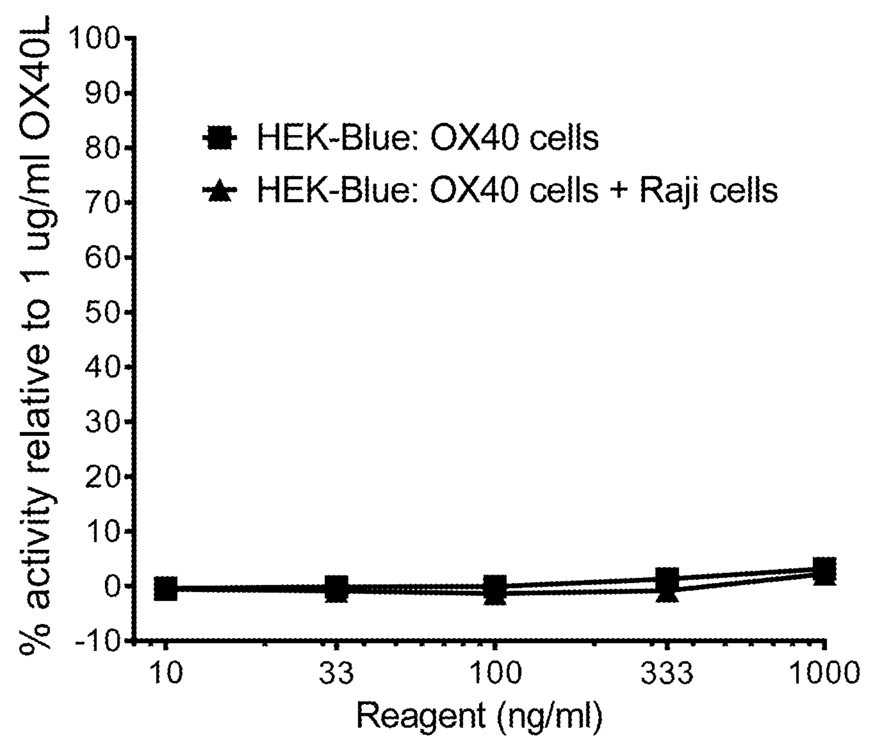
FIG. 6C shows that OX40SF2IgG2sigma antibody, which is silent in binding to Fc receptors, either alone or cross-linked in the presence of Raji cells has no agonistic activity in a HEK-Blue™ NFκB reporter assay. The agonistic activity was normalized as percent activity relative to that driven by 1 μg/ml OX40 ligand and plotted vs. concentrations of test antibodies. Data are presented as mean±SEM, n=8.
Figure 6D:
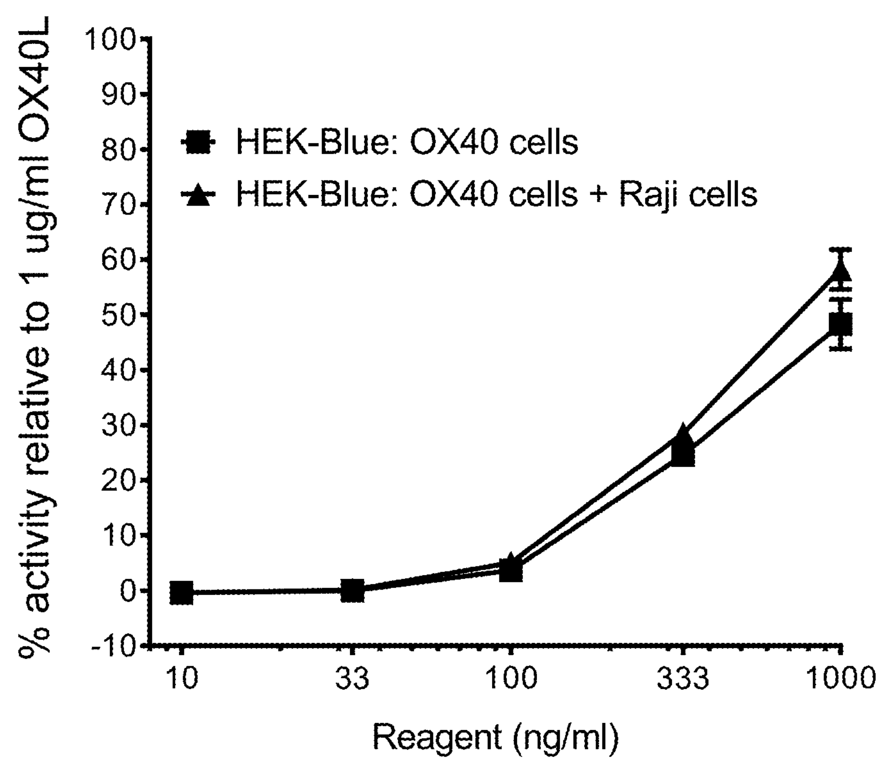
FIG. 6D shows that E345R mutation rescued agonistic activity of OX40SF2IgG2sigma in a HEK-Blue™ NFκB reporter assay. However, cross-linking with Raji cells failed to further boost its agonistic activity. The agonistic activity was normalized as percent activity relative to that driven by 1 μg/ml OX40 ligand and plotted vs. concentrations of test antibodies. Data are presented as mean±SEM, n=8.

E345 is a conserved residue among IgG subtypes. E345R mutation was also engineered on anti-OX40 antibody with the silent IgG2sigma Fc, resulting in antibody OX40SF2IgG2sigmaE345R. HEK-Blue™ NFκB reporter assay revealed that while OX40SF2IgG2sigma has little agonistic activity (FIG. 6C), the OX40SF2IgG2sigmaE345R showed agonism in a dose-dependent manner (FIG. 6D). This indicated that E345R mutation can facilitate agonism enhancement across multiple IgG subtypes.

FcγRIIB Crosslinking Further Boost the Agonism of Anti-OX40 Antibody with E345R Mutation Depending on IgG Subtype Although E345R mutation can facilitate the agonism of anti-OX40 antibody with either IgG1 or IgG2sigma Fc independent of FcγRIIB crosslinking, the effect of FcγRIIB crosslinking was nonetheless studied by HEK-Blue™ NFκB reporter assay in which the engineered antibodies were applied to HEK-Blue: OX40 cells co-cultured with Raji cells. It was observed that the presence of Raji cells can further boost the agonism of OX40SF2IgG1E345R antibody, with over two-fold increases in activity across test concentrations compared to the case without Raji cell co-culturing (FIG. 6B). When 2B6 antibody was added to pre-block FcγRIIB receptor on Raji cells, the Raji cell-mediated boost of agonism for OX40SF2IgG1E345R was completely abrogated, with agonistic activity reduced to a level similar to the case without Raji cell co-culturing, implying that the boost of agonism is driven by FcγRIIB crosslinking.

Similar assays were set up to evaluate FcγRIIB crosslinking on the agonism of OX40SF2IgG2sigma antibody with or without E345R mutation. It was found that the presence of Raji cells failed to boost the agonistic activity of either OX40SF2IgG2sigma or OX40SF2IgG2sigmaE345R antibody (FIG. 6C and FIG. 6D). This data indicated that Raji cell mediated boost of agonism for anti-OX40 antibody with E345R mutation depended on the IgG subtype, with effect on IgG1 Fc but no effect on the silent IgG2sigma Fc.

Effector Functions of Engineered Anti-OX40 Antibodies with E345R Mutation

Figure 7A:
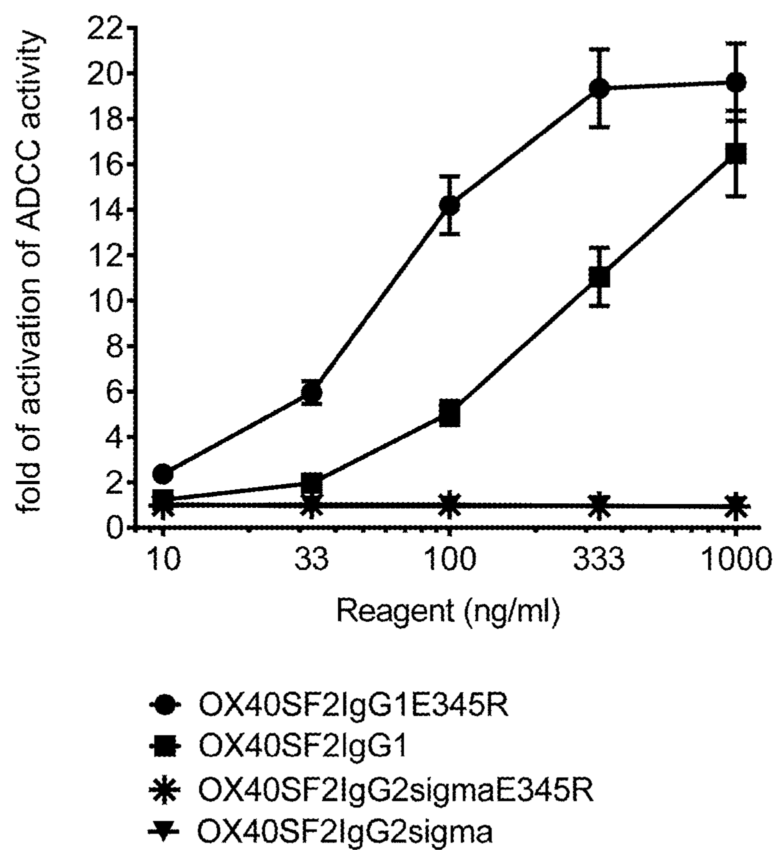
FIG. 7A shows that OX40SF2IgG1E345R has enhanced ADCC when compared to the wild-type antibody (OX40SF2IgG1), and that Fc silent OX40SF2IgG2sigma and OX40SF2IgG2sigmaE345R antibodies have abrogated ADCC. Increasing concentrations (10 ng/ml to 1000 ng/ml) of OX40SF2IgG1, OX40SF2IgG1E345R, OX40SF2IgG2sigma and OX40SF2IgG2sigmaE345R were incubated with HEK-Blue™ cells stably expressing OX40 co-cultured with effectors cells and the ADCC reporter bioassays were performed. The fold of activation of ADCC when compared to a sample without antibody were plotted vs. concentrations of test antibodies. Data are presented as mean±SEM, n≥4.

The ADCC activities of the anti-OX40 antibodies with E345R mutation were studied by the FcγRIIIA-mediated ADCC reporter bioassay. E345R mutation improved ADCC of the anti-OX40 antibody. OX40SF2IgG1E345R had improved ADCC when compared to OX40SF2IgG1 (FIG. 7A). In contrast, OX40SF2IgG2sigma demonstrated no ADCC activity, and introduction of E345R mutation onto OX40SF2IgG2sigma had no effect on ADCC.

Figure 7B:
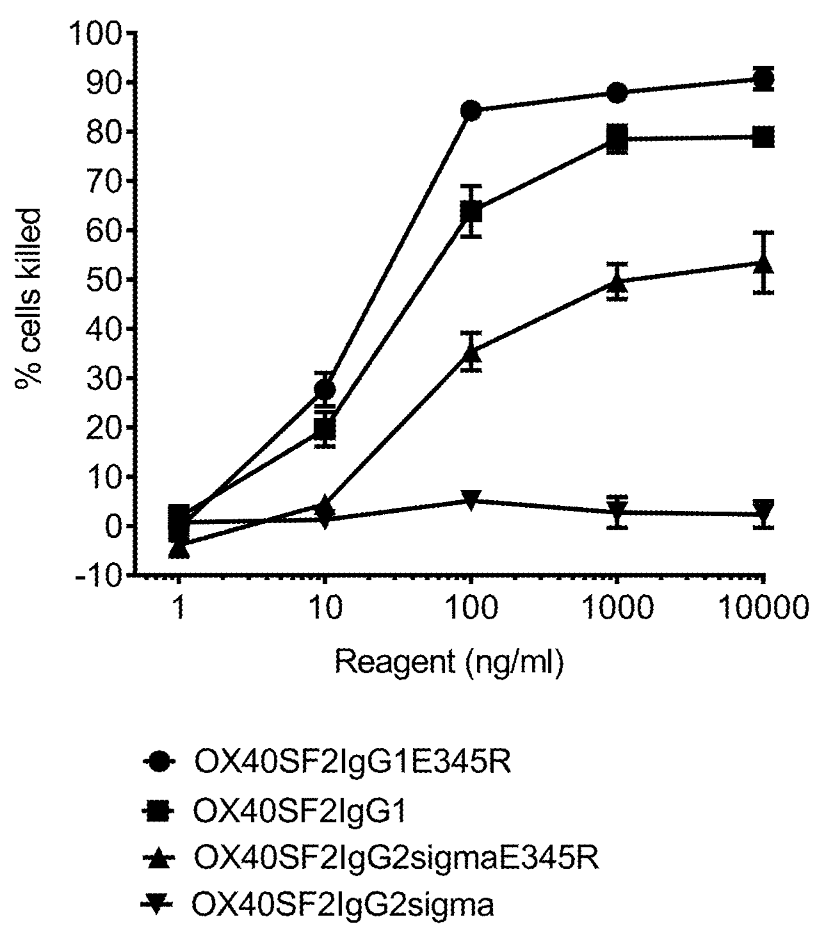
FIG. 7B shows that OX40SF2IgG1E345R has comparable ADCP to that of the wild-type IgG1 (OX40SF2IgG1), and that E345R rescues ADCP in effector silent antibody (OX40SF2IgG2sigmaE345R). Increasing concentrations (1 ng/ml to 10000 ng/ml) of OX40SF2IgG1, OX40SF2IgG1E345R, OX40SF2IgG2sigma and OX40SF2IgG2sigmaE345R antibodies were incubated with GFP positive HEK-Blue™ cells stably expressing OX40 with differentiated macrophages and the phagocytosis of GFP positive target cells were evaluated by flow cytometry assay. The percentages of GFP positive cells eliminated, which reflect the ADCP activities, were plotted vs. concentrations of test antibodies. Data are presented as mean±SEM, n≥9.

The ADCP activities of the anti-OX40 antibodies with E345R mutation were also studied by the phagocytosis of GFP-expressed HEK-Blue: OX40 cells by differentiated macrophages. OX40SF2IgG1 antibody dose-dependently mediated killing of HEK-Blue: OX40 target cells by the macrophages, while introduction of the E345R mutation only marginally enhanced the ADCP activity of OX40SF2IgG1 antibody (FIG. 7B). In contrast, while OX40SF2IgG2sigma had no ADCP activity, introduction of the E345R mutation onto OX40SF2IgG2sigma improved ADCP (FIG. 7B).

Figure 7C:
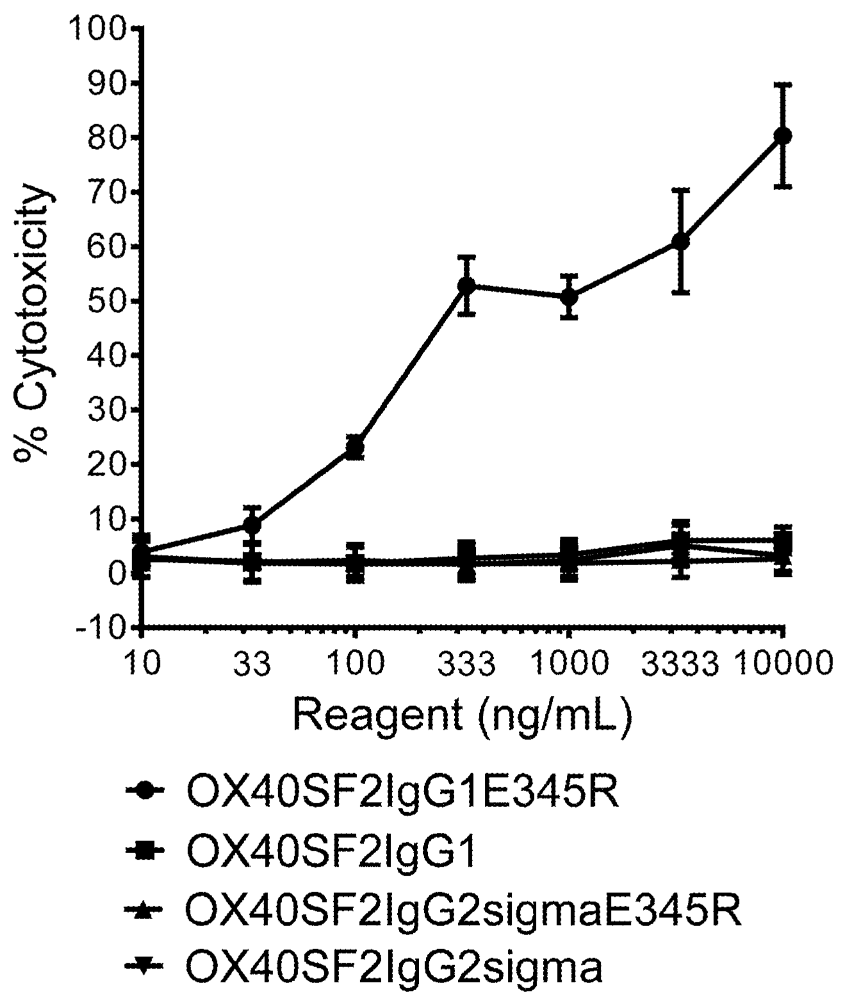
FIG. 7C shows that E345R mutation resulted in enhanced CDC activity of OX20SF2IgG1E345R but had no effect on effector silent OX40SF2IgG2sigmaE345R. Increasing concentrations (10 to 10,000 ng/ml) of OX40SF2IgG1, OX40SF2IgG1E345R, OX40SF2IgG2sigma, and OX40SF2IgG2sigmaE345R antibodies were incubated with HEK-Blue™ cells stably expressing OX40 in the presence of rabbit complement. The CDC activities were quantitated by measuring LDH activity released from the cytosol of lysed cells and expressed as percent cytotoxicity relative to that lysed by Triton X-100 (data were presented as mean±S.E., n=6).

Antibody-mediated CDC were studied in an assay evaluating lysis HEK-Blue: OX40 cells in the presence of rabbit complement. Although OX40SF2IgG1 antibody did not mediate significant CDC activity toward HEK-Blue:OX40 target cells, the E345R mutation dose-dependently facilitated OX40SF2IgG1 antibody with higher CDC activity. In contrast, the OX40SF2IgG2sigma antibody did not have CDC activity in this assay, and the E345R mutation on OX40SF2IgG2sigma antibody did not change its silencing in CDC activity (FIG. 7C).

Discussion

Agonistic antibodies directed against immunostimulatory TNFR superfamily members are emerging as promising drugs for cancer therapy. Recent Fc engineering efforts have been directed towards optimizing anti-TNFR superfamily antibodies for their antitumor immunity by enhancing their agonistic activity via optimizing their engagement with FcγRIIB by introducing substitutions S267E/L328F and V12 into the Fc (Chu et al. (2008) *Mol Immunol* 45: 3926-33; Mimoto et al. (2013) *Protein Eng Des Sel* 26: 589-98).

When applied herein to the anti-OX40 antibodies, the reported S267E/L328F and V12 mutations enhanced the binding of engineered anti-OX40 antibodies to FcγRIIB expressed in either transfected Expi293F cells or Raji cells and enhanced their agonistic activity in cross-linking dependent manner. The degree of agonism was comparable for both S267E/L328F and V12 mutations. S267E/L328F and V12 mutations in the OX40 antibodies disrupted antibody binding to FcγRIIIA while enhancing binding to FcγRIIB, which is consistent with that reported by Mimoto (Mimoto et al. (2013) *Protein Eng Des Sel* 26: 589-98. As a consequence, S267E/L328F and V12 mutations completely abrogated ADCC of the engineered anti-OX40 antibodies, which is largely mediated by FcγRIIIA expressed on NK cells.

It was also discovered herein that mutations that induce hexamerization of antibodies against tumor associated antigens such as CD20 (Diebolder et al. (2014) *Science* 343: 1260-3 (E345R, E430G, S440Y) induced agonistic activity of anti-OX40 antibodies. However, contrary to what is reported for S267E/L328F and V12 mutations, the improved agonistic activity was independent on FcγRIIB crosslinking Although anti-OX40 antibodies with E345R, E430G and E345R/E430G double mutations exist as monomers in solution, they became multimerized upon binding to OX40 on cell surface. The multimerized antibodies showed enhanced agonistic activity in the absence of FcγRIIB-expressing cells, presumably due to the facilitation of increased clustering of OX40 on cells. Although the double E345R/E430G and triple E345R/E430G/S440Y mutations resulted in higher antibody multimerization when compared to the singular mutation alone, the single E345R mutation resulted in antibodies with the highest agonistic activity. While not wishing to be bound by any particular theory, it is thought that the oligomerized antibody with E345R mutation has a more favorable configuration in promoting the clustering of OX40 receptors than the antibody with E430G mutation.

Although E345R mutation enhanced agonism independent of FcγRIIB crosslinking, it was found that the presence of FcγRIIB-expressing cells further enhanced agonism of antibodies with E345R mutation. This further boost of agonism depended on the interaction of the engineered antibody with FcγRIIB expressed on Raji cells as the boost of agonism was not observed on IgGsigma antibody silent in binding FcγR and the agonism was abrogated by pre-blocking FcγRIIB expressed on Raji cells. It has been reported that the multimerized antibody has higher affinity to Fcγ receptors compared to antibody in monomer (Luo et al. (2009) *MAbs* 1: 491-504). Indeed, the results presented herein demonstrate that OX40SF2E345R/E430G/S440Y, which is partially a hexamer form in solution, has much potent binding to FcγRIIB expressed on transfected Expi293F cells, compared to OX40SF2IgG1 and OX40SF2IgG1E345R antibodies, which exist as monomers in solution (data not shown). It is hypothesized that the oligomerized OX40SF2IgG1E345R bound to OX40 on the cell surface may have increased binding to FcγRIIB on Raji cells, which in turn further stabilize antibody multimerization and facilitate receptor clustering that lead to the boost of agonism.

The E345R mutation introduced into the anti-OX40 antibodies enhanced the potency of ADCC activity of the antibodies. The effect was specific for engineered antibody on IgG1, which is capable of binding to FcγRIIIA, but not for antibody on IgG2sigma, which does not bind FcγRIIIA. These observations suggested that the E345R-mediated enhancement of ADCC activity for IgG1 antibody was likely through increased binding of FcγRIIIA with oligomerized antibodies upon recognizing OX40 on the cell surface.

Relative to anti-OX40 antibodies with native IgG1 Fc, neither the S267E/L328F nor the V12 mutations significantly affected ADCP. This might be unexpected for the S267E/L328F mutations, which were reported to have enhanced binding to FcγRIIA (Mimoto et al. (2013) *Protein Eng Des Sel* 26: 589-98), a major Fc receptor expressed on macrophages mediating phagocytosis. However, besides FcγRIIA, several Fc receptors, including FcγRI and FcγRIIIA contribute to IgG antibody mediated phagocytosis of target cells (Indik et al. (1995) *Blood* 86: 4389-99). The OX40SF2IgG1S267E/L328F antibody demonstrated similar binding potency to FcγRI as OX40SF2IgG1 but abrogated binding to FcγRIIIA. Besides, the degree of enhanced FcγRIIA binding was just to a level comparable to its binding to the high affinity FcγRI receptor. As a result, OX40SF2IgG1S267E/L328F antibody showed similar binding potency to macrophage as OX40SF2IgG1 and it did not show enhanced ADCP activity relative to OX40SF2IgG1. In contrast, the OX40SF2IgG1V12 antibody has reduced binding to FcγRI and FcγRIIIA, and unchanged binding potency to FcγRIIA, which might explain its significantly reduced binding to macrophages. Nonetheless, the OX40SF2IgG1V12 antibody showed a similar ADCP activity as OX40SF2IgG1. The reason for this discrepancy is unknown. Similarly, no significant increase in ADCP activity was observed for OX40SF2IgG1 antibody with E345R mutation, although such mutation significantly enhanced the ADCC activity of the engineered antibody. Interestingly, although OX40SF2IgG2sigma did not have ADCP activity, the E345R mutation conferred significant ADCP activity to this antibody with silent Fc.

Each of the several Fc engineering approaches evaluated in this study offer a unique property in simultaneously enhancing the agonistic activity and modulating effect functions of the engineered antibodies. Depending on the requirement for ADCC, various engineering approaches can be envisioned for therapeutic antibodies binding TNFR superfamily members. For example, antibodies binding CD40 and CD27 may benefit from improved agonistic activity but minimal ADCC to minimize risk of cell depletion. Therefore, S267E/L328F or V12 on IgG1 or E345R on IgG2sigma could be used to generate improved CD40 and CD27 antibodies. In contrast, when ADCC activity is desired for example to eliminate regulatory T cells, E345R mutation on IgG1 can be used. For example, antibodies binding to OX40 or GITR may benefit from improved agonistic activity and enhanced ADCC.

Another consideration is whether the dependency on FcγRIIB crosslinking is desired or not for agonism enhancement. The E345R mutation can facilitate higher agonism independent of FcγRIIB crosslinking, which may equip antibody with defined therapeutic activity regardless of FcγR expression levels in the local microenvironment, particularly an advantage for those cancer types with low FcγR expressing cells infiltrated. However, the non-dependency on FcγRIIB crosslinking may stimulate agonism non-specifically, which may lead to undesired off-target effects. In such case, the S267E/L328F or V12 mutations could be used. Other factors, including the altered binding activities to different Fc receptors, the immunogenicity, PK profile and developability of the engineered antibody should also be considered in the choice of the optimal engineering approach.

We claim:

1. An isolated anti-tumor necrosis factor receptor (TNFR) superfamily member antibody, wherein the antibody comprises an amino acid sequence of SEQ ID NOs: 63, 64, 65, 66 or 67 having an E345R mutation, an E345R/E430G mutation or a E345R/E430G/S440Y mutation, residue numbering according to the EU Index, and has enhanced agonistic activity when compared to a parental antibody without the mutation.

2. The antibody of claim 1, comprising the E345R mutation.

3. The antibody of claim 1, comprising the E345R/E430G mutation.

4. The antibody of claim 1, comprising the E345R/E430G/S440Y mutation.

5. The antibody of claim 1, wherein the antibody has agonistic activity independent of antibody cross-linking.

6. The antibody of claim 5, wherein the antibody is an IgG1, IgG2, IgG3 or IgG4 isotype.

7. The antibody of claim 6, further comprising a second mutation.

8. The antibody of claim 7, wherein the second mutation is a L234A/L235A mutation on IgG1, a V234A/G237A/P238S/H268A/V309L/A330S/P331S mutation on IgG2, a F234A/L235A mutation on IgG4, a S228P/F234A/L235A mutation on IgG4, a N297A mutation on all Ig isotypes, a V234A/G237A mutation on IgG2, a K214T/E233P/L234V/L235A/G236-deleted/A327G/P331A/D365E/L358M mutation on IgG1, a H268Q/V309L/A330S/P331S mutation on IgG2, a L234F/L235E/D265A mutation on IgG1, a L234A/L235A/G237A/P238S/H268A/A330S/P331S mutation on IgG1, a S228P/F234A/L235A/G237A/P238S mutation on IgG4, or a S228P/F234A/L235A/G236-deleted/G237A/P238S mutation on IgG4.

9. The antibody of claim 8, wherein the second mutation is the V234A/G237A/P238S/H268A/V309L/A330S/P331S mutation on IgG2.

10. The antibody of claim 8, wherein the second mutation is the L234A/L235A/G237A/P238S/H268A/A330S/P331S mutation on IgG1.

11. The antibody of claim 8, wherein the second mutation is the S228P/F234A/L235A mutation on IgG4.

12. The antibody of claim 1, wherein the receptor of the TNFR family is OX40 (SEQ ID NO: 4).

13. A pharmaceutical composition comprising the antibody of claim 1 and a pharmaceutically acceptable carrier.

* * * * *